(12) United States Patent
van Hemert et al.

(10) Patent No.: US 11,540,712 B2
(45) Date of Patent: Jan. 3, 2023

(54) FUNCTIONAL OCT DATA PROCESSING

(71) Applicant: Optos Plc, Dunfermline (GB)

(72) Inventors: Jano van Hemert, Dunfermline (GB); Michael Verhoek, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 288 days.

(21) Appl. No.: 16/930,465

(22) Filed: Jul. 16, 2020

(65) Prior Publication Data
US 2021/0022601 A1 Jan. 28, 2021

(30) Foreign Application Priority Data

Jul. 26, 2019 (NL) ..................................... 2023578

(51) Int. Cl.
| | |
|---|---|
| G06T 7/11 | (2017.01) |
| A61B 3/00 | (2006.01) |
| A61B 3/10 | (2006.01) |
| G06T 7/00 | (2017.01) |

(52) U.S. Cl.
CPC ............ *A61B 3/102* (2013.01); *A61B 3/0008* (2013.01); *A61B 3/0025* (2013.01); *G06T 7/0012* (2013.01); *G06T 7/11* (2017.01); *G06T 2207/30041* (2013.01)

(58) Field of Classification Search
None
See application file for complete search history.

(56) References Cited

U.S. PATENT DOCUMENTS

| | | |
|---|---|---|
| 7,980,694 B2 | 7/2011 | Keating et al. |
| 2009/0128776 A1 | 5/2009 | Keating |
| | (Continued) | |

FOREIGN PATENT DOCUMENTS

| | | | |
|---|---|---|---|
| GB | WO 2007 148073 A1 | 12/2007 | |
| JP | 2012 161382 A | 8/2012 | |
| JP | 2017 213062 A | 12/2017 | |
| | (Continued) | | |

OTHER PUBLICATIONS

Examination Report dated Mar. 5, 2021 (pp. 1-5), relating to Australian application 2020205235.

(Continued)

*Primary Examiner* — Idowu O Osifade
(74) *Attorney, Agent, or Firm* — DeLucia, Mlynar & Associates LLP

(57) ABSTRACT

A method of processing functional OCT image data, acquired by an OCT scanner scanning a retina that is being repeatedly stimulated by a light stimulus, to obtain a response of the retina to the light stimulus, comprising: receiving OCT image data generated by the OCT scanner repeatedly scanning the retina over a time period, and a sequence of stimulus indicators each indicative of a stimulation of the retina by the light stimulus in a respective time interval of a sequence of time intervals spanning the time period; calculating, for each stimulus indicator, a product of the stimulus indicator and a respective windowed portion of the sequence of B-scans comprising a B-scan based on a portion of the OCT image data generated while the retina was being stimulated in accordance with the stimulus indicator; and combining the calculated products to generate the indication of the response.

18 Claims, 31 Drawing Sheets

(56) References Cited

U.S. PATENT DOCUMENTS

2017/0032502 A1* 2/2017 van Hemert ............ G06T 5/006
2018/0008144 A1 1/2018 Kobayashi

FOREIGN PATENT DOCUMENTS

| WO | WO 2009 089509 A1 | 7/2009 |
| WO | WO2010009447 A2 | 1/2010 |
| WO | WO 2016/136926 A1 | 9/2016 |
| WO | WO 2018/183304 A1 | 10/2018 |

OTHER PUBLICATIONS

Hillmann D et al., "In vivo optical imaging of physiological response to photostimulation in human photoreceptors", Proceedings of the National Academy of Sciences, vol. 113, No. 46, pp. 13138 to 13143, (2016).

Tumlinson, A. et al., "Techinques for extraction of depth-resolved in vivo human retinal intrinsic optical signals with optical coherence tomography", Japanese Journal of Ophthalmology, vol. 53, pp. 315 to 326, (2009).

Suzuki W., et al., "Stimulus-induced changes of reflectivity detected by optical coherence tomography in macaque retina", Investigative Ophthalmology & Visual Science, vol. 54, No. 9, pp. 6345 to 6354, (2013).

Search Report dated Mar. 19, 2019, relating to NL2023578 (9 sheets).

Lewis, J. P., "Fast Normalized Cross-Correlation," Industrial Light & Magic, expanded version of a paper from Vision Interface, 1995 (reference [10]) (7 sheets).

Haralick, Robert M., and Linda G. Shapiro, "Computer and Robot Vision", vol. II, Addison-Wesley, 1992, pp. (9 sheets including cover page for vol. II, Table of contents pp. iii. to x., and pp. 1 and 316-321).

Taeyoon Son et al., Optical coherence tomography angiography of stimulus evoked hemodynamic responses in individual retinal layers, Biomedical Optics Express, Aug. 1, 2016, vol. 7, No. 8, pp. 3151-3162.

P. L. Muller et al., M-sequences in ophthalmic electrophysiology, Journal of Vision, Jan. 31, 2016, vol. 1, No. 15, pp. 1-19.

Office Action dated Feb. 21, 2022 in Korean Patent Application 10-2020-0092426 (12 sheets); English translation attached (8 sheets).

Notice of Reasons for Rejection dated Jul. 13, 2021 in Japanese application 2020-126722 (2 sheets) (English translation attached; 3 sheets).

Christine Haselier et al., Correlations between specific patterns of spontaneous activity and stimulation efficiency in degnerated retine, PLOS ONE, Dec. 17, 2017, vol. 12, No. 12, pp. 1-16.

B. Sander et al., Br. J. Ophthalmol., Jan. 21, 2005, vol. 89, No. 2, pp. 207-212.

Alireza Akhlagh Moayed et al., Correlation of visually evoked intrinsic optical signals and electroretinograms recorded from chicken retina with a combined functional optical coherence tomography and electrolinography system, J. of Biomedical Optics, Feb. 8, 2012, vol. 17, No. 1, pp. 1-6.

Notice of Allowance dated Sep. 29, 2022 in Korean patent application No. 10-2020-0092426 (English translation included on first page of original).

* cited by examiner

Functional OCT report:
Retinal Nerve Fibre Layer

OD OS

| OD | Eye | OS |
|---|---|---|
| RNFL | Layer | RNFL |
| 177 ms | First peak | 150 ms |
| 351 ms | Second peak | 312 ms |
| 4.5 | Amplitude | 8.7 |

FUNCTIONAL OCT DATA PROCESSING

This application claims the benefit of priority of Netherlands Patent Application No. NL 2023578, filed Jul. 26, 2019, the contents of which are incorporated by reference herein in their entirety, as if set forth fully herein.

FIELD

Example aspects herein generally relate to the field of optical coherence tomography (OCT) data processing and, more particularly, to the processing of functional OCT image data, which has been acquired by an OCT imaging device scanning a retina of a subject while the retina is being repeatedly stimulated by a light stimulus, to generate an indication of a response of the retina to the light stimulus.

BACKGROUND

Functional OCT provides an indication of how well a retina of an eye responds to light stimulation, and can provide a powerful tool for assessing the health of the eye. However, the amount of tomographic data acquired in a typical functional OCT measurement, in which OCT data may be acquired at a high data rate while the retina is being stimulated by hundreds or thousands of light flashes over a period of 20-30 seconds, for example, is usually very large (typically over 100 GB), and needs to be correlated with information defining the timing of applied light stimuli, making the processing of functional OCT data a complex task that can be very demanding on computer resources.

SUMMARY

To address at least some of the drawbacks of prior methods of processing functional OCT image data, there is provided, in accordance with a first example aspect herein, a computer-implemented method of processing functional OCT image data, which has been acquired by an OCT imaging device scanning a retina of a subject while the retina is being repeatedly stimulated by a light stimulus, to generate an indication of a response of the retina to the light stimulus. The method comprises receiving, as the functional OCT image data: OCT image data that has been generated by the OCT imaging device repeatedly scanning a scanned region of the retina over a time period; and stimulus data defining a sequence of stimulus indicators each being indicative of a stimulation of the retina by the light stimulus in a respective time interval of a sequence of time intervals that spans the time period. The method further comprises calculating a rolling window correlation between a sequence of B-scans that is based on the OCT image data and stimulus indicators in the sequence of stimulus indicators by: calculating, for each stimulus indicator, a product of the stimulus indicator and a respective windowed portion of the sequence of B-scans comprising a B-scan which is based on a portion of the OCT image data generated while the retina was being stimulated in accordance with the stimulus indicator; and combining the calculated products to generate the indication of the response of the retina to the light stimulus.

There is also provided, in accordance with a second example aspect herein, a computer-implemented method of processing functional OCT image data, which has been acquired by an OCT imaging device scanning a retina of a subject while the retina is being repeatedly stimulated by a light stimulus, to generate an indication of a response of the retina to the light stimulus. The method comprises receiving, as the functional OCT image data: OCT image data that has been generated by the OCT imaging device repeatedly scanning a scanned region of the retina over a time period; and stimulus data defining a sequence of stimulus indicators each being indicative of a stimulation of the retina by the light stimulus in a respective time interval of a sequence of time intervals that spans the time period. The method further comprises calculating a rolling window correlation between a sequence of B-scans that is based on the OCT image data and at least some of the stimulus indicators in the sequence of stimulus indicators by calculating, for each stimulus indicator, a correlation between stimulus indicators in a window comprising the stimulus indicator and a predetermined number of adjacent stimulus indicators, and B-scans of the sequence of B-scans that are based on a portion of the OCT image data generated while the retina was being stimulated in accordance with the stimulus indicators in the window. The method further comprises generating the indication of the response of the retina to the light stimulus by combining the calculated correlations.

There is also provided, in accordance with a third example aspect herein, a computer-implemented method of processing functional OCT image data, which has been acquired by an OCT imaging device scanning a retina of a subject while the retina is being repeatedly stimulated by a light stimulus, to generate image data defining an image that provides an indication of a response of the retina to the light stimulus. The method comprises receiving, as the functional OCT image data: OCT image data that has been generated by the OCT imaging device repeatedly scanning a scanned region of the retina over a time period; and stimulus data defining a sequence of stimulus indicators each being indicative of a stimulation of the retina by the light stimulus in a respective time interval of a sequence of time intervals that spans the time period. The method further comprises calculating a rolling window correlation between a sequence of B-scans that is based on the OCT image data and stimulus indicators in the sequence of stimulus indicators. The method further comprises using the calculated correlation to generate image data defining an image which indicates at least one of: the response of the scanned region of the retina to the light stimulus as a function of time; one or more properties of a curve defining the response of the scanned region of the retina to the light stimulus as a function of time; and a spatial variation, in the scanned region of the retina, of one or more properties of the curve defining the response of the scanned region of the retina to the light stimulus as a function of time, the spatial variation being overlaid on an en-face representation of at least a portion the retina which includes the scanned region.

There is also provided, in accordance with a fourth example aspect herein, a computer program which, when executed by a processor, causes the processor to perform a method according to at least one of the first example aspect, the second example aspect, or the third example aspect herein.

There is also provided, in accordance with a fifth example aspect herein, a non-transitory computer-readable storage medium storing the computer program according to the fourth example aspect herein.

BRIEF DESCRIPTION OF THE DRAWINGS

Example embodiments will now be explained in detail, by way of non-limiting example only, with reference to the accompanying figures described below. Like reference

FIG. 6(*b*) is a schematic illustration of a first example process by which the correlation calculator module 120-1 of the first example embodiment herein may process the two-dimensional array 800 of correlation values to generate a normalised two-dimensional array of correlation values, 900-1.

FIG. 6(*c*) is a schematic illustration of a second example process by which the correlation calculator module 120-1 of the first example embodiment herein may process the two-dimensional array 800 of correlation values to generate a normalised two-dimensional array of correlation values, 900-2.

FIG. 23(*b*) is a schematic illustration of a first example process by which the response generator module 125-5 of the fifth example embodiment herein may process the two-dimensional array 800' of combined correlation values to generate a normalised two-dimensional array of combined correlation values, 900'-1.

FIG. 23(*c*) is a schematic illustration of a second example process by which the response generator module 125-5 of the fifth example embodiment herein may process the two-dimensional array 800' of combined correlation values to generate a normalised two-dimensional array of combined correlation values, 900'-2.

DETAILED DESCRIPTION OF EMBODIMENTS

Figure 1:
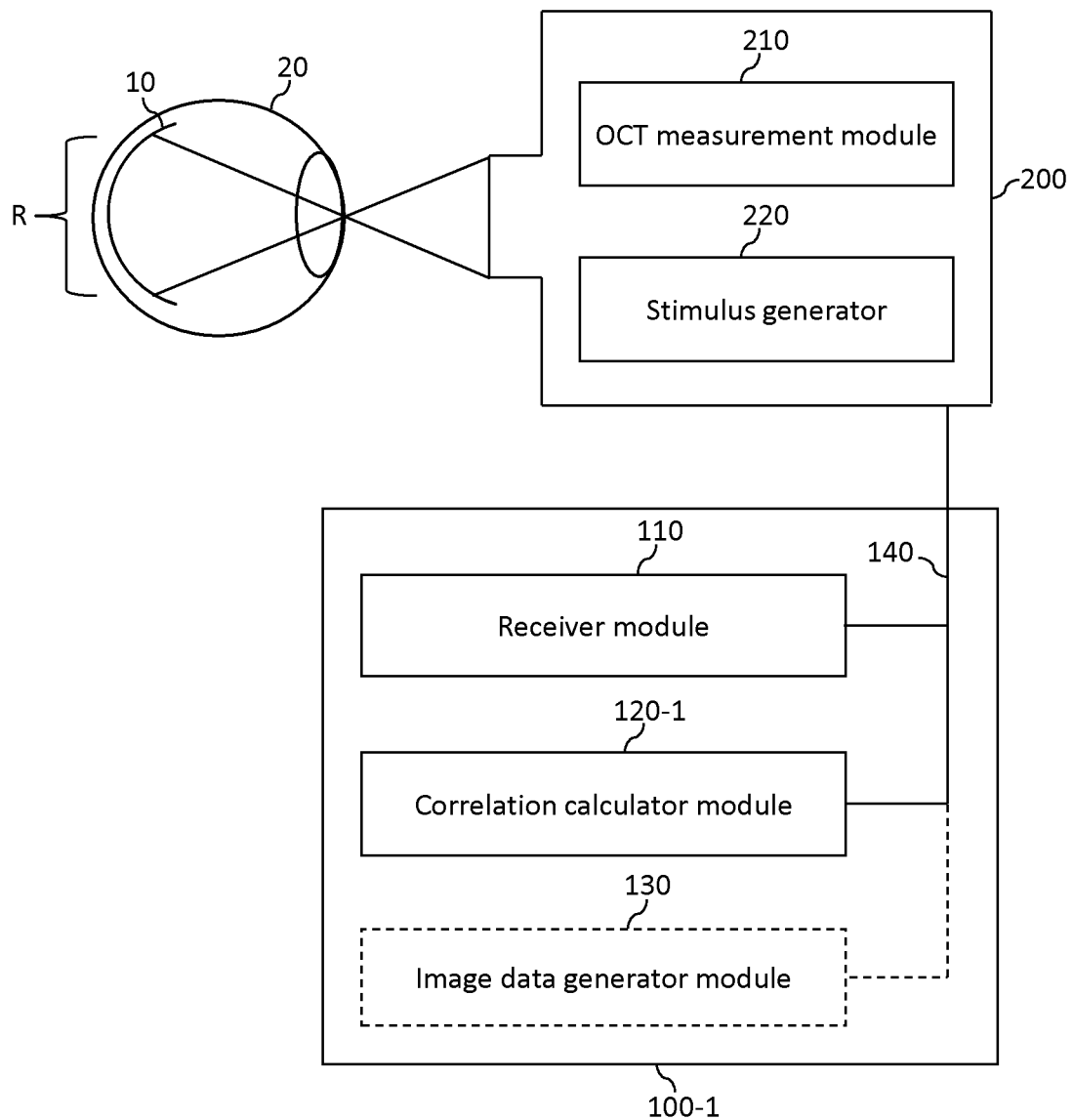
FIG. 1 is a schematic illustration of an apparatus for processing functional OCT image data according to a first example embodiment herein.

There is described herein, by way of example embodiments, an apparatus for processing functional OCT image data, which has been acquired by an OCT imaging device scanning a retina of a subject while the retina is being repeatedly stimulated by a light stimulus, to generate image data defining an image that provides an indication of a response of the retina to the light stimulus. The apparatus comprises a receiver module configured to receive, as the functional OCT image data: OCT image data that has been generated by the OCT imaging device repeatedly scanning a scanned region of the retina over a time period; and stimulus data defining a sequence of stimulus indicators each being indicative of a stimulation of the retina by the light stimulus in a respective time interval of a sequence of time intervals that spans the time period. The apparatus further comprises a correlation calculator module configured to calculate a rolling window correlation between a sequence of B-scans that is based on the OCT image data and stimulus indicators in the sequence of stimulus indicators. The rolling window correlation may be calculated in a number of different ways. For example, the correlation calculator module may calculate the rolling window correlation between the sequence of B-scans and the stimulus indicators in the sequence of stimulus indicators by calculating, for each of a plurality of windowed portions of the sequence of B-scans, a respective product of a stimulus indicator in accordance which the retina was stimulated while OCT image data, on which at least one of the B-scans in the windowed portion of the sequence of B-scans is based, was being generated by the OCT imaging device, and at least a portion of each B-scan in the windowed portion of the sequence of B-scans. The correlation calculator module may alternatively calculate the rolling window correlation between the sequence of B-scans and the stimulus indicators in the sequence of stimulus indicators by calculating, for each stimulus indicator, a correlation between stimulus indicators in a window comprising the stimulus indicator and a predetermined number of adjacent stimulus indicators, and B-scans of the sequence of B-scans that are based on a portion of the OCT image data generated while the retina was being stimulated in accordance with the stimulus indicators in the window. Some example methods of calculating the rolling window correlation that may be employed by the correlation calculator module are set out in the following description of example embodiments.

The apparatus set out above further comprises an image data generator module configured to use the calculated rolling window correlation to generate image data defining an image which indicates at least one of: the response of the scanned region of the retina to the light stimulus as a function of time; one or more properties of a curve defining the response of the scanned region R of the retina to the light stimulus as a function of time; and a spatial variation, in the scanned region of the retina, of one or more properties of the curve defining the response of the scanned region of the retina to the light stimulus as a function of time, the spatial variation being overlaid on an en-face representation of at least a portion the retina which includes the scanned region.

There is also described in the following, by way of example embodiments, a computer-implemented method of processing functional OCT image data, which has been acquired by an OCT imaging device scanning a retina of a subject while the retina is being repeatedly stimulated by a light stimulus, to generate image data defining an image that provides an indication of a response of the retina to the light stimulus. The method comprises receiving, as the functional OCT image data: OCT image data that has been generated by the OCT imaging device repeatedly scanning a scanned region of the retina over a time period; and stimulus data defining a sequence S of stimulus indicators each being indicative of a stimulation of the retina by the light stimulus in a respective time interval of a sequence of time intervals that spans the time period. The method further comprises calculating a rolling window correlation between a sequence of B-scans that is based on the OCT image data and stimulus indicators in the sequence S of stimulus indicators, as mentioned above. The method further comprises using the calculated rolling window correlation to generate image data defining an image which indicates at least one of: the response of the scanned region of the retina to the light stimulus as a function of time; one or more properties of a curve defining the response of the scanned region of the retina to the light stimulus as a function of time; and a spatial variation, in the scanned region of the retina, of one or more properties of the curve defining the response of the scanned region of the retina to the light stimulus as a function of time, the spatial variation being overlaid on an en-face representation of at least a portion of the retina which includes the scanned region.

Example embodiments herein will now be described in more detail with reference to the accompanying drawings.

Embodiment 1

FIG. 1 is a schematic illustration of an apparatus 100-1 according to a first example embodiment, which is configured to process functional Optical Coherence Tomography (OCT) image data to generate an indication of how well a retina 10 of a subject's eye 20 responds to a flickering light stimulus. The functional OCT data processed by the apparatus 100-1 is acquired by an OCT imaging device 200, specifically by the OCT imaging device 200 employing an ophthalmic scanner (not shown) to scan an OCT sample beam generated by an OCT measurement module 210 across a region R of the subject's retina 10 while the retina 10 is being repeatedly stimulated by a light stimulus generated by a light stimulus generator 220 of the OCT imaging device 200.

The light stimulus may, as in the present example embodiment, comprise a full-field light stimulus (or flash), which provides substantially uniform illumination (at wavelengths in the visible spectrum between about 380 and 740 nm in the present example, although other wavelengths could alternatively or additionally be used) that fills the whole visual field of the subject. The light stimulus generator 220 may, for example, comprise a light-emitting diode (LED) or other optical emitter for generating the light stimuli. The flashes that the light stimulus generator 220 emits may, as in the present example embodiment, give rise to a random (or pseudo-random) stimulation of the retina over time. In other words, the light stimulus generator 220 may emit light flashes that are randomly or pseudo-randomly distributed in time, so that the subject cannot (subconsciously) learn to anticipate upcoming flashes, thereby allowing a more accurate functional response to the subject's retina 10 to light stimulation to be measured.

It should be noted, however, that the light stimulus need not be a full-field stimulus, and may alternatively stimulate only a portion of the retina, which may be illuminated in accordance with a structural scan pattern (e.g. an annulus, a hypotrochoid, or Lissajous figure, for example) by the ophthalmic scanner (not shown) of the OCT imaging device 200.

As illustrated in FIG. 1, the apparatus 100-1 of the present example embodiment comprises a receiver module 110, a correlation calculator module 120-1 and, optionally, an image data generator module 130, which are communicatively coupled (e.g. via a bus 140) so as to be capable of exchanging data with one another and with the OCT imaging device 200.

Figure 2:
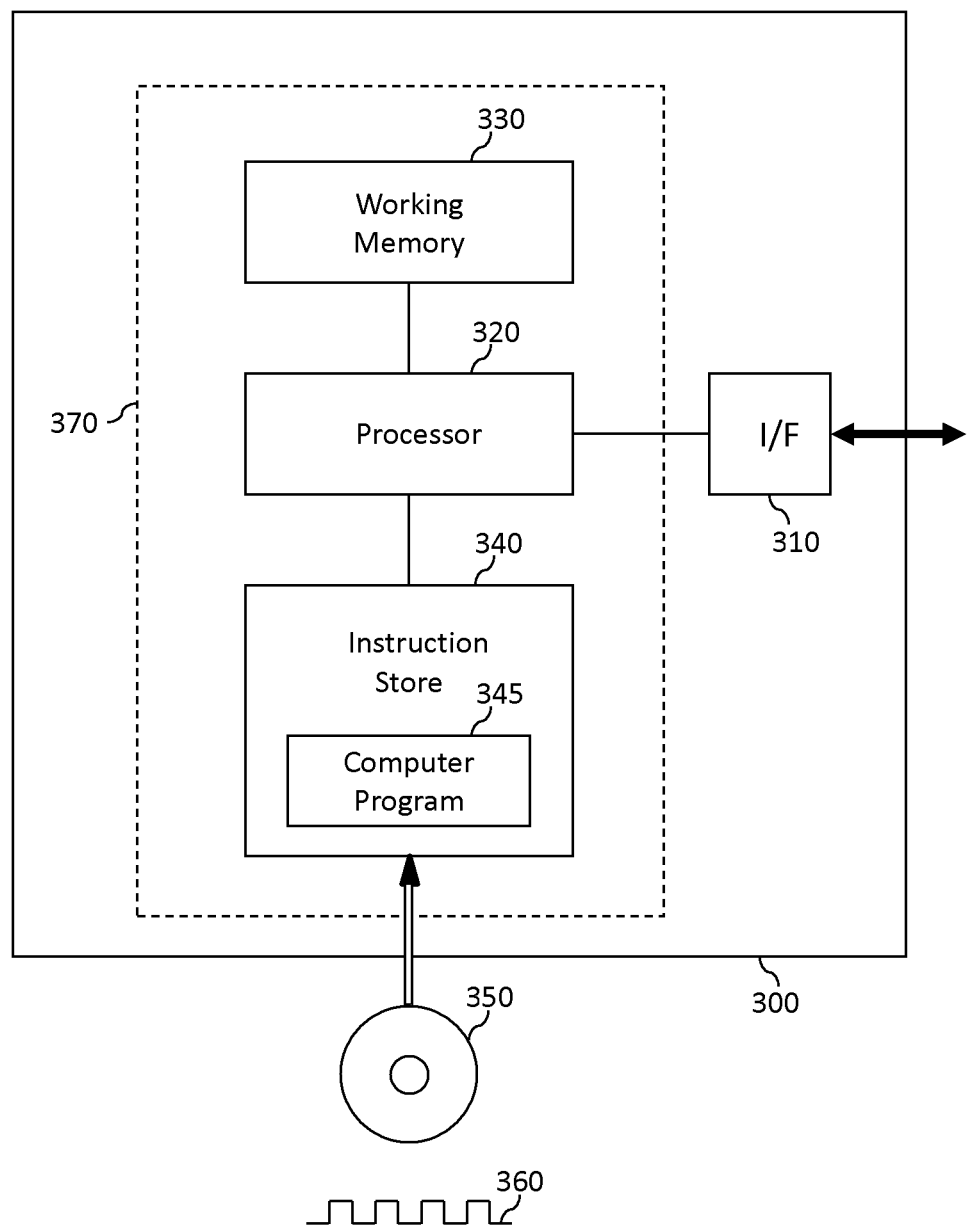
FIG. 2 is a block diagram illustrating an example implementation of the apparatus of the first example embodiment in signal processing hardware.

FIG. 2 is a schematic illustration of a programmable signal processing hardware 300, which may be configured to process functional OCT data using the techniques described herein and, in particular, function as the receiver module 110, the correlation calculator module 120-1 and the (optional) image data generator module 130 of the first example embodiment. The programmable signal processing hardware 300 comprises a communication interface (I/F) 310 for receiving the functional OCT data from the OCT imaging device 200, and outputting image data described herein below, which defines an image indicating the response of the retina to the light stimulus. The signal processing apparatus 300 further comprises a processor (e.g. a Central Processing Unit, CPU, or Graphics Processing Unit, GPU) 320, a working memory 330 (e.g. a random access memory) and an instruction store 340 storing a computer program 345 comprising the computer-readable instructions which, when executed by the processor 320, cause the processor 320 to perform various functions including those of the receiver module 120-1, the correlation calculator module 120-1 and/or the image data generator module 130 described herein. The working memory 330 stores information used by the processor 320 during execution of the computer program 345, including intermediate processing results such as the calculated products of stimulus indicators and respective windowed portions of the sequence of B-scans, for example. The instruction store 340 may comprise a ROM (e.g. in the form of an electrically-erasable programmable read-only memory (EEPROM) or flash memory) which is pre-loaded with the computer-readable instructions. Alternatively, the instruction store 340 may comprise a RAM or similar type of memory, and the computer-readable instructions of the computer program 345 can be input thereto from a computer program product, such as a non-transitory, computer-readable storage medium 350 in the form of a CD-ROM, DVD-ROM, etc. or a computer-readable signal 360 carrying the computer-readable instructions. In any case, the computer program 345, when executed by the processor 320, causes the processor 320 to execute a method of processing functional OCT data as described herein. It should be noted, however, that the receiver module 110, the correlation calculator module 120-1 and/or the image data generator module 130 may alternatively be implemented in non-programmable hardware, such as an application-specific integrated circuit (ASIC).

In the present example embodiment, a combination 370 of the hardware components shown in FIG. 2, comprising the processor 320, the working memory 330 and the instruction store 340, is configured to perform functions of the receiver module 110, the correlation calculator module 120-1 and the image data generator module 130 that are described below.

Figure 3:
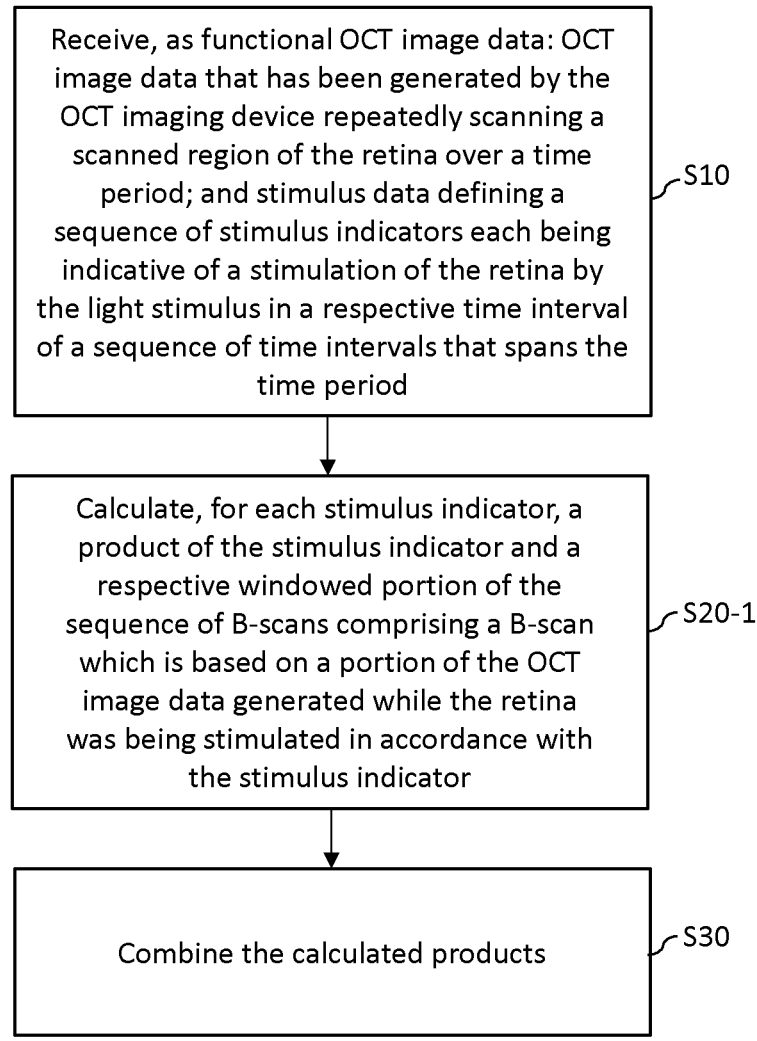
FIG. 3 is a flow diagram illustrating a method of processing functional OCT image data, which has been acquired by an OCT imaging device scanning the subject's retina while the retina is being repeatedly stimulated by the light stimulus, to generate an indication of a response of the retina to the light stimulus in the first example embodiment herein.

FIG. 3 is a flow diagram illustrating a method performed by the processor 320, by which the processor 320 processes functional OCT data, which has been acquired by the OCT imaging device 200 scanning the subject's retina 10 while the retina 10 is being repeatedly stimulated by the light stimulus, to generate an indication of a response of the retina 10 to the light stimulus.

In step S10 of FIG. 3, the receiver module 110 receives from the OCT imaging device 200, as the functional OCT image data: (i) OCT image data that has been generated by the OCT imaging device 200 repeatedly scanning a scanned region R of the retina 10 over a time period T; and (ii) stimulus data defining a sequence of s stimulus indicators, each stimulus indicator being indicative of a stimulation of the retina 10 by the light stimulus in a respective time interval, T/s, of a sequence of time intervals that spans the time period T.

Figure 4:
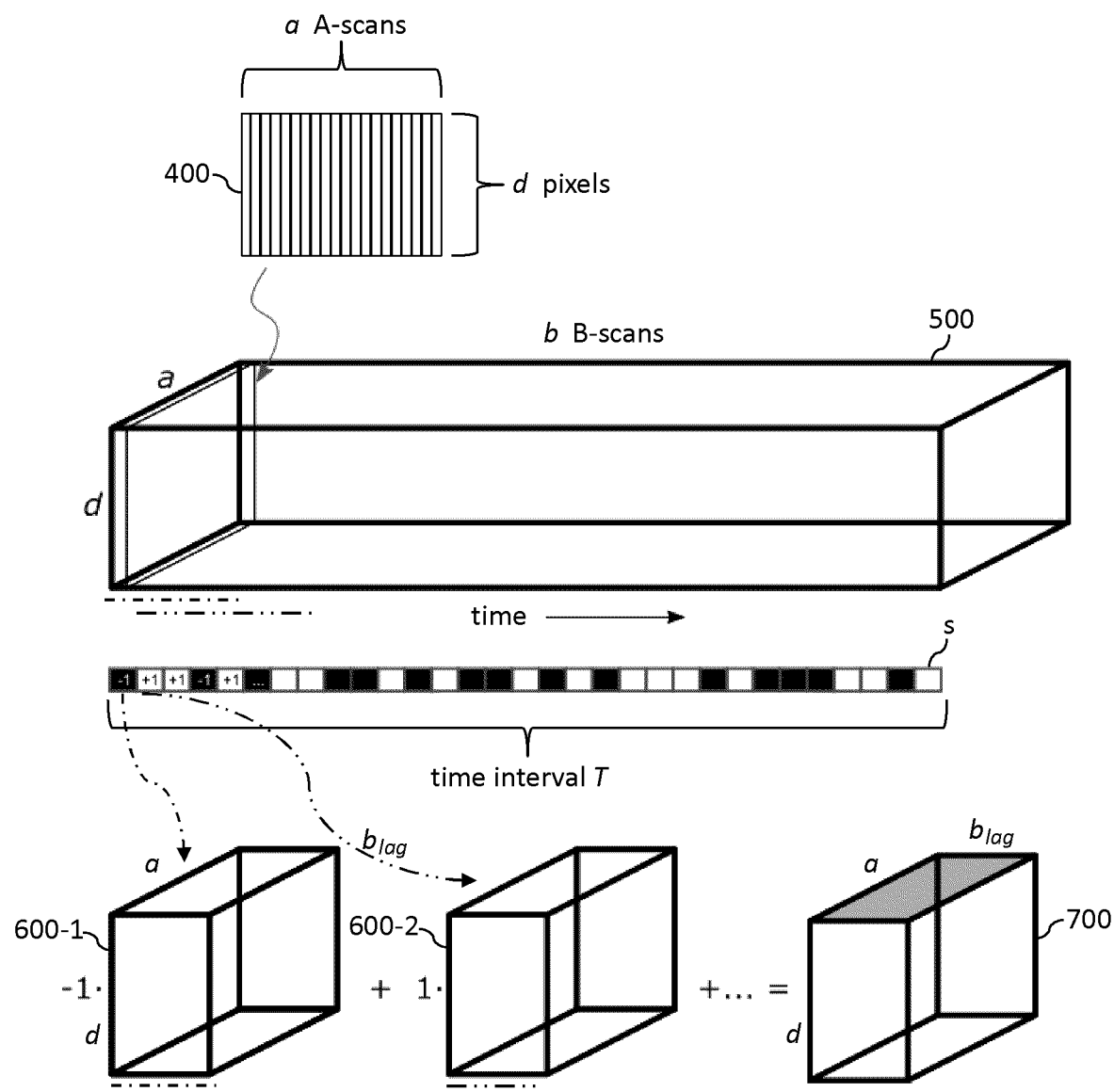
FIG. 4 is a schematic illustration of functional OCT image data acquired by a receiver module 110 in step S10 of FIG. 3, and results of processing the functional OCT image data in the first example embodiment herein.

The received OCT image data may, as in the present example embodiment, comprise a sequence of b B-scans, which has been generated by the OCT imaging device 200 repeatedly scanning the scanned region R of the retina 10 over the time period T. FIG. 4 illustrates functional OCT image data acquired by the receiver module 110 in step S10 of FIG. 3. As illustrated in FIG. 4, each B-scan 400 in the sequence of B-scans can be represented as a 2D image made up of a A-scans (vertical lines). Each A-scan comprises a one-dimensional array of d pixels, where the pixel value of each pixel represents a corresponding OCT measurement result, and the location of each pixel in the one-dimensional array is indicative of the OCT measurement location in the axial direction of the OCT imaging device 200, at which location the corresponding pixel value was measured. The OCT image data can thus be represented as a three-dimensional pixel array 500, which is a×b×d pixels in size.

It should be noted that each A-scan in the B-scan 400 may be an average of a number of adjacent A-scans that have been acquired by the OCT imaging device 200. In other words, the OCT imaging device 200 may acquire A-scans having lateral spacing (e.g. along the surface of the retina) which is smaller than the optical resolution of the OCT imaging device 200, and average sets of adjacent A-scans to generate a set of averaged A-scans which make up a B-scans displaying improved signal-to-noise.

The OCT imaging device 200 generates the OCT image data by scanning a laser beam across the scanned region R of the retina 10 in accordance with a predetermined scan pattern, acquiring the A-scans that are to make up each B-scan 400 as the scan location moves over the scanned region R. The shape of the scan pattern on the retina 10 is not limited, and is usually determined by a mechanism in the OCT imaging device 200 that can steer the laser beam generated by the OCT measurement module 210. In the present example embodiment, galvanometer ("galvo") motors, whose rotational position values are recorded, are used to guide the laser beam during the acquisition of the OCT data. These positions can be correlated to locations on the retina 10 in various ways, which will be familiar to those versed in the art. The scan pattern may, for example, trace out a line, a curve, or a circle on the surface of the retina 10, although a lemniscate scan pattern is employed in the present example embodiment. The A-scans acquired during each full period of the scan pattern form one B-scan. In the present example embodiment, all of the b B-scans are recorded in the time period T, such that the time per B-scan is T/b, and the scan pattern frequency is b/T.

During the time period T, while the OCT image data is being generated by the OCT imaging device 200, a stimulus is shown to the subject, which can be a full-field stimulus (substantially the same brightness value over the whole visual field), as in the present example embodiment, or a spatial pattern, where the visual field is divided into e.g. squares, hexagons or more complicated shapes. In the case of a full-field stimulus, at any point in time, the brightness can be denoted, for example, as either "1" (full brightness) or as "−1" (darkness, with no stimulus having been applied). The time period T is divided into a sequence of s time intervals (corresponding to the "stimulus positions" referred to herein), each of size T/s and, for each time interval, there is an associated stimulus indicator ($s_1$, $s_2$, $s_3$ ...) which is indicative of a stimulation of the retina 10 by the light stimulus in the respective time interval T/s. Thus, each stimulus indicator in the sequence of stimulus indicators may take a value of either 1 or −1 (although the presence or absence of the stimulus may more generally be denoted by n and −n, where n is an integer). The concatenation of the stimulus indicator values that are indicative of the stimulation of the retina 10 during OCT image data generation is referred to herein as a sequence S of stimulus indicators. One choice for S is an m-sequence, which is a pseudo-random array. In alternative embodiments, in which there is a spatial pattern to the stimulus, each individual field can either display a completely different m-sequence, or a version of one m-sequence that is (circularly) delayed by a specific time, or an inversion of one m-sequence (i.e. when one field shows a 1, another shows a −1 and vice versa). As noted above, the receiver module 110 is configured to receive stimulus data defining the sequence S of stimulus indicators $s_1$, $s_2$, $s_3$, etc. The receiver module 110 may, for example, receive information defining the sequence S of stimulus indicators itself, or alternatively information that allows the sequence S of stimulus indicators to be constructed by the apparatus 100-1.

It should be noted that, although each stimulus indicator in the sequence S of stimulus indicators is indicative of whether or not the retina 10 was stimulated by the light stimulus in the corresponding time interval of duration T/s, the stimulus indicator is not so limited, and may, in other example embodiments, be indicative of a change in stimulation of the retina 10 by the light stimulus that occurs in a respective time interval of the sequence S of time intervals that spans the time period T. For example, in the following description of correlation calculations, each windowed portion of the sequence of B-scans may be multiplied by −1 if the stimulus changes from +1 to −1 in the associated time interval T/s, by +1 if the stimulus changes from −1 to +1 in the associated time interval T/s, and by zero if the stimulus does not change in the time interval.

After at least some of the functional OCT data have been received by the receiver module 110, the correlation calculator 120-1 begins to calculate a rolling window correlation between a sequence of B-scans that is based on the OCT image data and at least some of the stimulus indicators in the sequence S of stimulus indicators.

More particularly, the correlation calculator module 120-1 calculates the rolling window correlation firstly by calculating, in step S20-1 of FIG. 3, for each of the stimulus indicators $s_1$, $s_2$, $s_3$, etc., a product of the stimulus indicator and a respective windowed portion of the sequence of B-scans 500 comprising a predetermined number, $b_{lag}$, of B-scans, beginning with (or otherwise including) a B-scan which is based on a portion of the OCT image data generated while the retina 10 was being stimulated in accordance with the stimulus indicator. The correlation calculator module 120-1 thus generates in step S20-1 of FIG. 3 a plurality of calculated products. It should be noted that the intervals T/b and T/s are not necessarily equal, and that there are b/s B-scans per stimulus position/indicator, or s/b stimuli per B-scan. By way of an example, b/s=2 in the present example embodiment, so that two B-scans are generated by the OCT imaging device 200 while the retina is being stimulated, or is not being stimulated (as the case may be), in accordance with each stimulus indicator value. Thus, the correlation calculator module 120-1 calculates a product of the value of the first stimulus indicator $s_1$, which is −1 in the example of FIG. 4, and each of the data elements of a first portion (or block) 600-1 of the three-dimensional array of pixels 500, which portion 600-1 is a×$b_{lag}$×d pixels in size and includes two B-scans that were generated by the OCT imaging device 200 while the retina 10 was not being stimulated (in accordance with the stimulus indicator value "−1" applicable for the time interval from time t=0 to t=T/s) and six subsequent B-scans, as $b_{lag}$=8 in the example of FIG. 4 (although other values for $b_{lag}$ could alternatively be used). The value of $b_{lag}$ is preferably set to correspond to the number of B-scans generated by the OCT imaging device 200 in a period of no more than about 1 second, as the use of greater values of $b_{lag}$ may make little or no improvement to the calculated retinal response, whilst making the calculation more demanding of computational resources. In other words, the correlation calculator module 120-1 multiplies each matrix element of a matrix, which is formed by the portion 600-1 of the three-dimensional array 500 of pixels that is a×$b_{lag}$×d pixels in size, by the value ("−1") of the first stimulus indicator, $s_1$, in the sequence S of indicator values defined by the received stimulus data. Then, for the second stimulus indicator, $s_2$, in the sequence S of stimulus indicators (having the value "+1"), each data element of the data elements of a second portion (or block) 600-2 of the three-dimensional pixel array 500, which second portion 600-2 is also a×$b_{lag}$×d pixels in size but begins with the two B-scans that were generated by the OCT imaging device 200 while the retina was being stimulated (in accordance with the second stimulus indicator value "+1" applicable for the time interval from time t=T/s to t=2T/s) and also includes six adjacent, subsequent B-scans, by the corresponding stimulus indicator value "+1". This multiplication process is repeated for the remaining stimulus indicators in the sequence S of stimulus indicators, with the correlation calculator module 120-1 moving the rolling window forward in time by one time interval T/s in each step of the process, so that it slides past the second stimulus indicator, $s_1$, in the sequence S of stimulus indicators and covers the stimulus indicator immediately adjacent the right-hand boundary of the rolling window as it was previously positioned, and the product of the stimulus indicator and windowed portion of the sequence of B-scans 500 is calculated once again, using the newly-windowed portion of the sequence S of stimulus indicators and the corresponding B-scans in the sequence of B-scans 500 to generate another block of eight weighted B-scans. This procedure of sliding the rolling window forward in time and calculating the product to obtain a block of weighted B-scans for each rolling window position is repeated until the rolling window reaches the end of the sequence S of stimulus indicators, thereby generating a plurality of data blocks that are each $a \times b_{lag} \times d$ pixels in size, as illustrated in FIG. 4.

In step S30 of FIG. 3, the correlation calculator module 120-1 combines the calculated products, thus generating an indication of the response of the retina 10 to the light stimulus. In the present example embodiment, the correlation calculator module 120-1 combines the calculated products by performing a matrix addition of the plurality of data blocks 600-1, 600-2 . . . etc. generated in step S20-1, which are each $a \times b_{lag} \times d$ pixels in size, to generate a response block (also referred to herein as a "response volume") 700, which is a three-dimensional array of correlation values that is likewise $a \times b_{lag} \times d$ array elements in size. The correlation values in the response block 700 may each be divided by s, to obtain a normalised response.

As an alternative to the correlation calculation described above (sum of stimulus values multiplied with OCT blocks), it is also possible to use a more advanced normalisation cross-correlation that takes into account mean and standard deviation of the intensities in the sequence of B-scans 500 and mean and standard deviation of stimulus values in the sequence of stimulus indicators S. Such normalisation cross-correlation may be calculated using the "normxcorr2" function in Matlab™, for example.

The three-dimensional array 700 of correlation values may further be processed by the correlation calculator module 120-1, and the results of those further processing operations may be used by the image data generator module 130 to generate image data defining an image which indicates the response of the retina to the light stimulus for display to a user of the apparatus 100-1, so that an assessment of how well the retina responds to stimulation can be made. These optional further processing operations will now be described with reference to the flow diagram in FIG. 5.

The response volume 700 may be reduced to a two-dimensional response image for easier visualisation by taking the average in the depth (d) direction, i.e. one value per A-scan per lag time point. Thus, in (optional) step S40 of FIG. 5, the correlation calculator module 120-1 converts the three-dimensional array 700 of correlation values, which is $a \times b_{lag} \times d$ pixels in size, into a two-dimensional array 800 of correlation values, which is $a \times b_{lag}$ pixels in size (as illustrated in FIG. 6(a)), by replacing each one-dimensional array of correlation values in the three-dimensional array 700, which one-dimensional array has been calculated using A-scans that are identically located in respective B-scans of the sequence 500 of B-scans, with a single value that is an average of the correlation values in the one-dimensional array. The two-dimensional array 800 of correlation values indicates the response of the retina 10 to the light stimulus as a function of location along the scanned region R of the retina 10 (i.e. as a function of position along the line defining the scan pattern) and time.

The image data generator module 130 may use the two-dimensional array 800 of correlation values to generate image data defining an image which indicates the response of the retina to the light stimulus as a function of location in the scanned region of the retina and time, where the values of a and $b_{lag}$ determine the extent of the spatial and temporal variations of the response. However, it may be preferable to pre-process the two-dimensional array 800 of correlation values generated in step S40 prior to image data generation (or prior to the alternative further processing operation described below), in order to accentuate the time-dependent variability of the signal, i.e. the variation of the retinal response to light stimulation over time. Such pre-processing may be desirable in cases where the response variability in the A-scan direction is greater than in the time lag direction.

Figure 6A:
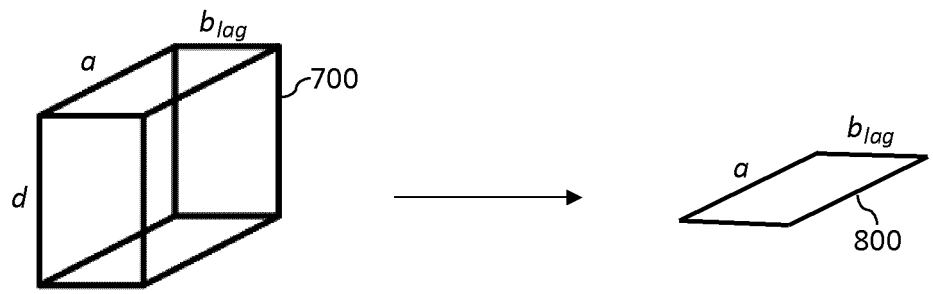
FIG. 6(*a*) is a schematic illustration of a conversion of a three-dimensional array 700 of correlation values into a two-dimensional array 800 of correlation values by the correlation calculator module 120-1 of the first example embodiment herein.
Figure 6B:
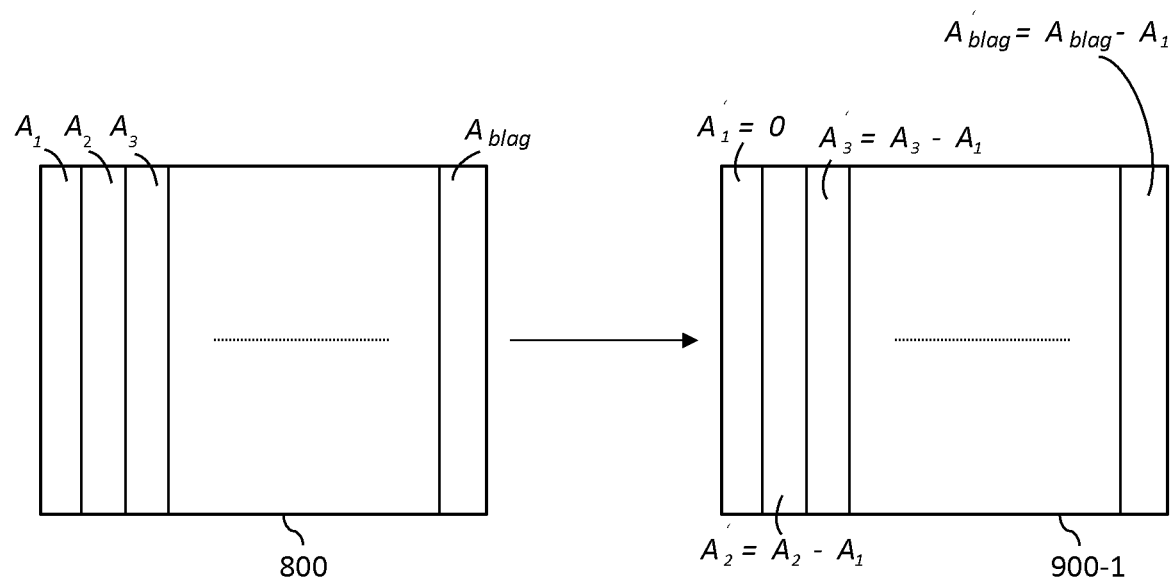
Figure 6C:
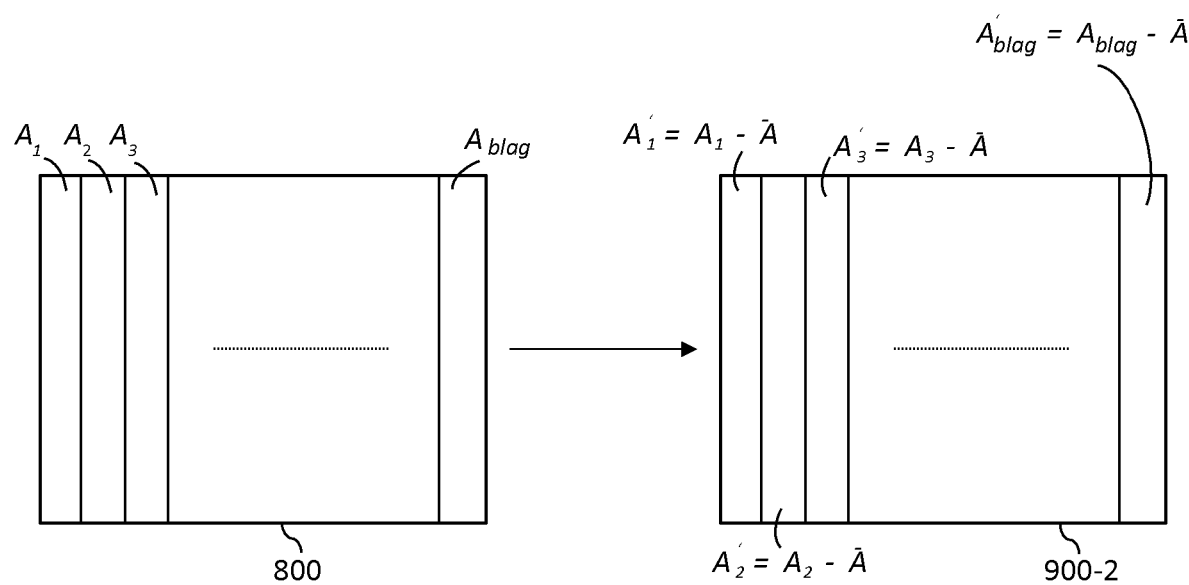

The correlation calculator module 120-1 may pre-process the two-dimensional array 800 of correlation values, which comprises a sequence of $b_{lag}$ one-dimensional arrays ($A_1$, $A_2$, . . . $A_{b_{lag}}$), each indicating the response of the retina 10 to the light stimulus as a function of location in the scanned region R of the retina 10, by generating a normalised two-dimensional array of correlation values. The correlation calculator module 120-1 may, as illustrated in FIG. 6(b), generate a normalised two-dimensional array, 900-1, of correlation values by subtracting the first one-dimensional array, $A_1$, in the sequence of one-dimensional arrays from each remaining one-dimensional array ($A_2$, $A_3$, . . . , $A_{b_{lag}}$) in the sequence of one-dimensional arrays. Alternatively, the correlation calculator module 120-1 may generate a normalised two-dimensional array of correlation values, 900-2, by calculating an array of averaged correlation values, $$\overline{A} = \frac{1}{b_{lag}} \sum_{n=1}^{b_{lag}} A_n,$$

such that each averaged correlation value in the array of averaged correlation values is an average (mean) of the correlation values that are correspondingly located in the sequence of one-dimensional arrays, and subtracting the calculated array of averaged correlation values, $\overline{A}$, from each of the one-dimensional arrays ($A_1$, $A_2$, $A_3$, . . . , $A_{b_{lag}}$) in the sequence of one-dimensional arrays (in other words, performing a vector subtraction of the calculated array of averaged correlation values from each of the one-dimensional arrays), as illustrated in FIG. 6(c). In both of these alternative ways of calculating normalised two-dimensional array of correlation values, the resulting normalised two-dimensional array of correlation values, 900-1 or 900-2, indicates the response of the retina to the light stimulus as a function of location in the scanned region R of the retina 10 and time.

Figure 5:
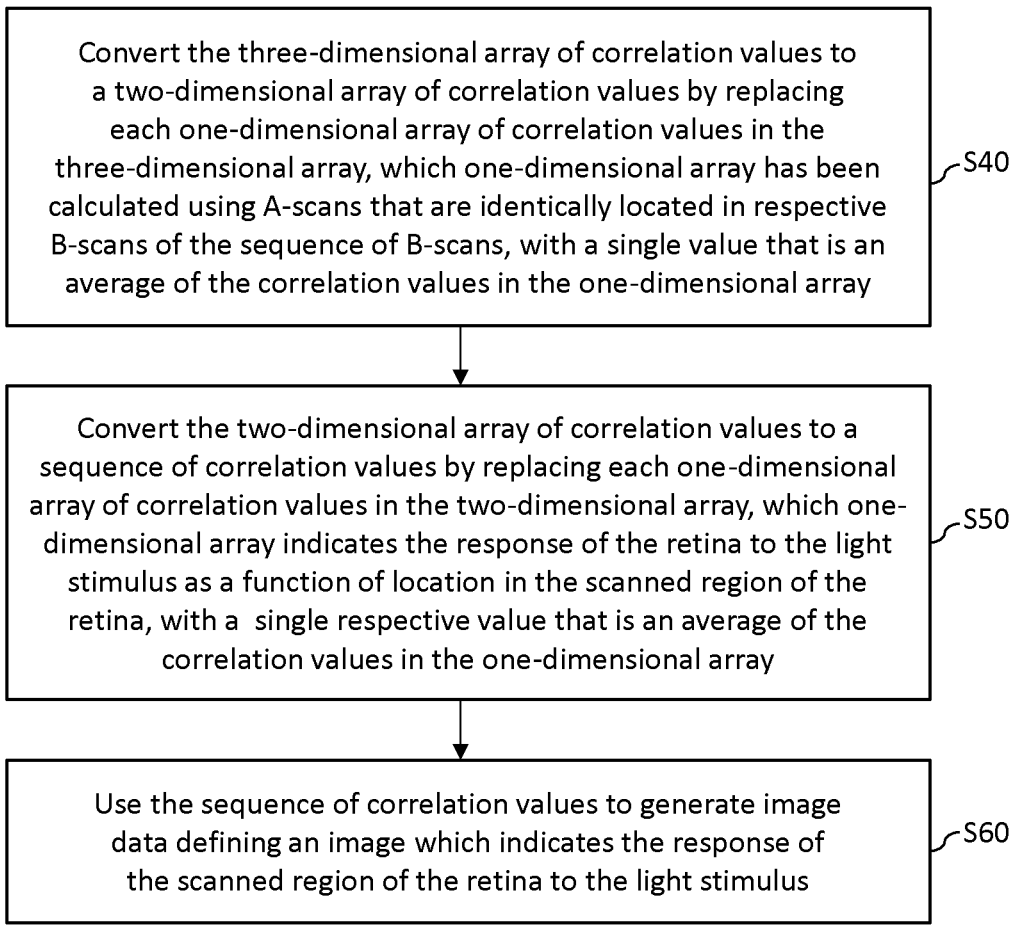
FIG. 5 is a flow diagram illustrating a process by which a three-dimensional array of correlation values generated by a correlation calculator mode 120-1 may further be processed to generate image data in the first example embodiment herein.

To allow the response of the retina to the light stimulus to be illustrated in a form that may be more useful for a healthcare practitioner such as an ophthalmologist, the correlation calculator module 120-1 may, as shown in step S50 of FIG. 5, convert the two-dimensional array of correlation values (or the normalised two-dimensional array of correlation values, as the case may be) to a sequence of correlation values by replacing each of the one-dimensional arrays of correlation values in the two-dimensional array 800, 900-1 or 900-2 (each of the one-dimensional arrays indicating the response of the retina 10 to the light stimulus as a function of location in the scanned region R of the retina 10) with a single respective value that is an average of the correlation values in the one-dimensional array, the sequence of correlation values indicating a response of the scanned region R of the retina 10 to the light stimulus as a function of time.

In step S60 of FIG. 5, the image data generator module 130 uses the sequence of correlation values generated in step S50 to generate image data defining an image which indicates the response of the retina 10 to the light stimulus.

Figure 7:
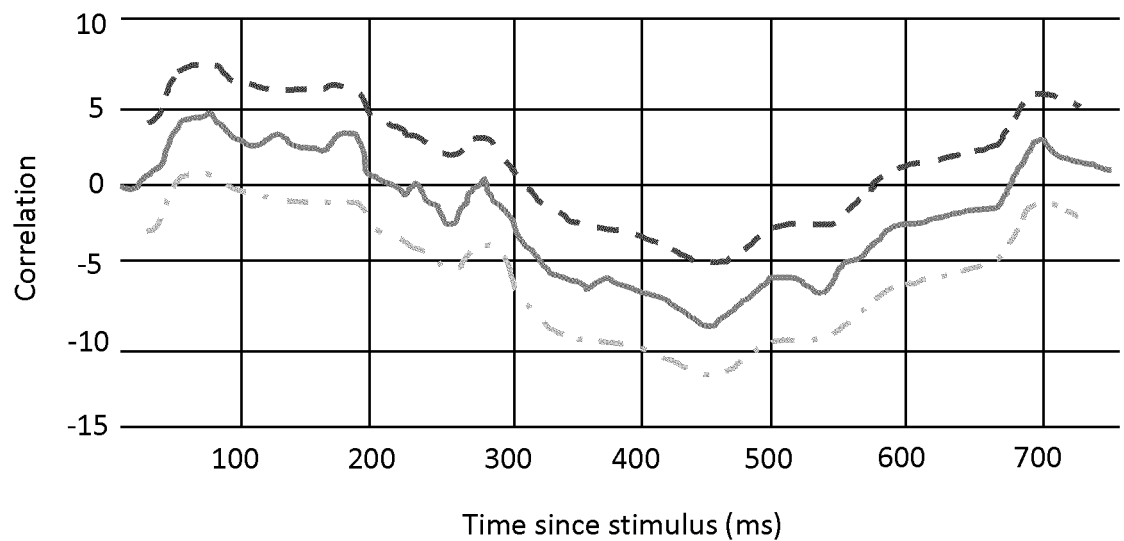
FIG. 7 is an example of an image defined by image data generated by an image data generator module 130 of the first example embodiment herein, which indicates a calculated response of the scanned region of the retina to an applied light stimulus as a function of time.

The image data may, for example, define an image which indicates the calculated response of the scanned region R of the retina 10 to the light stimulus as a function of time; in other words, the strength of the correlation of the change in OCT intensity with the time elapsed since the corresponding stimulus was applied. An example of such an image is shown in FIG. 7, where the solid response curve illustrates the strength of the calculated correlation of the change in OCT intensity with the time elapsed since the corresponding stimulus was applied. This data may, as also illustrated in FIG. 7, be augmented by additional plotted curves (or coloured bands) defining upper and lower limits, which may be created, for example, by computing a confidence interval from functional OCT data recorded from a set of healthy eyes. Diseased eyes would be expected to fall outside of these limits, thereby aiding the healthcare practitioner to diagnose potential loss of function. A typical representation may show a green band for the 95% confidence interval as computed from functional OCT data acquired from a set of healthy eyes. Alternatively, bands or limits may be displayed that have been computed from functional OCT data acquired from eyes with specific diseases.

Additionally or alternatively, the image data may define an image which indicates one or more properties of a curve which defines the response of the scanned region R of the retina 10 to the light stimulus as a function of time, for example the (solid) response curve shown in FIG. 7. An indicated property of the response curve may (depending on the shape of the curve) be the presence of a change from a predetermined first value to at least a predetermined second (higher or lower) value, the presence of one or more maxima or minima in the response curve, or the absence of a significant change in the calculated correlation strength indicated by the response curve (e.g. as determined by the calculated correlation strength remaining within predefined upper and lower limits), for example. The latter property, i.e. no change in the response curve (other than any noise that may be present) might be expected to be observed in data from diseased eyes, which show little or no response to light stimulation. The indicated property of the response curve may alternatively be data (referred to herein as a "marker") which quantifies one or more of the aforementioned features of the response curve. For example, where there is an extremum (a maximum or a minimum) in the response curve, the image defined by the image data may provide an indication of the time to the extremum since the stimulus was applied and/or an indication of the amplitude of the extremum relative to a predefined reference (e.g. zero correlation strength). Where there is a second extremum in the response curve (which may be the same or a different kind of extremum than the first extremum), the image defined by the image data may additionally or alternatively provide an indication of the time to the second extremum since the stimulus was applied and/or an indication of the amplitude of the second extremum relative to the predefined reference, and/or an indication of the difference in amplitude between the first and second extrema, for example. The indication(s) (marker(s)) may be provided in the form of one or more numerical values, or as a classification of each value into one of a number of predefined numerical ranges, for example. Each indication may be augmented, in the image that is defined by the image data, with a comment or a colour to indicate whether it is within a normal (healthy) range, or within an abnormal range of values that is indicative of a diseased state.

Figure 8:
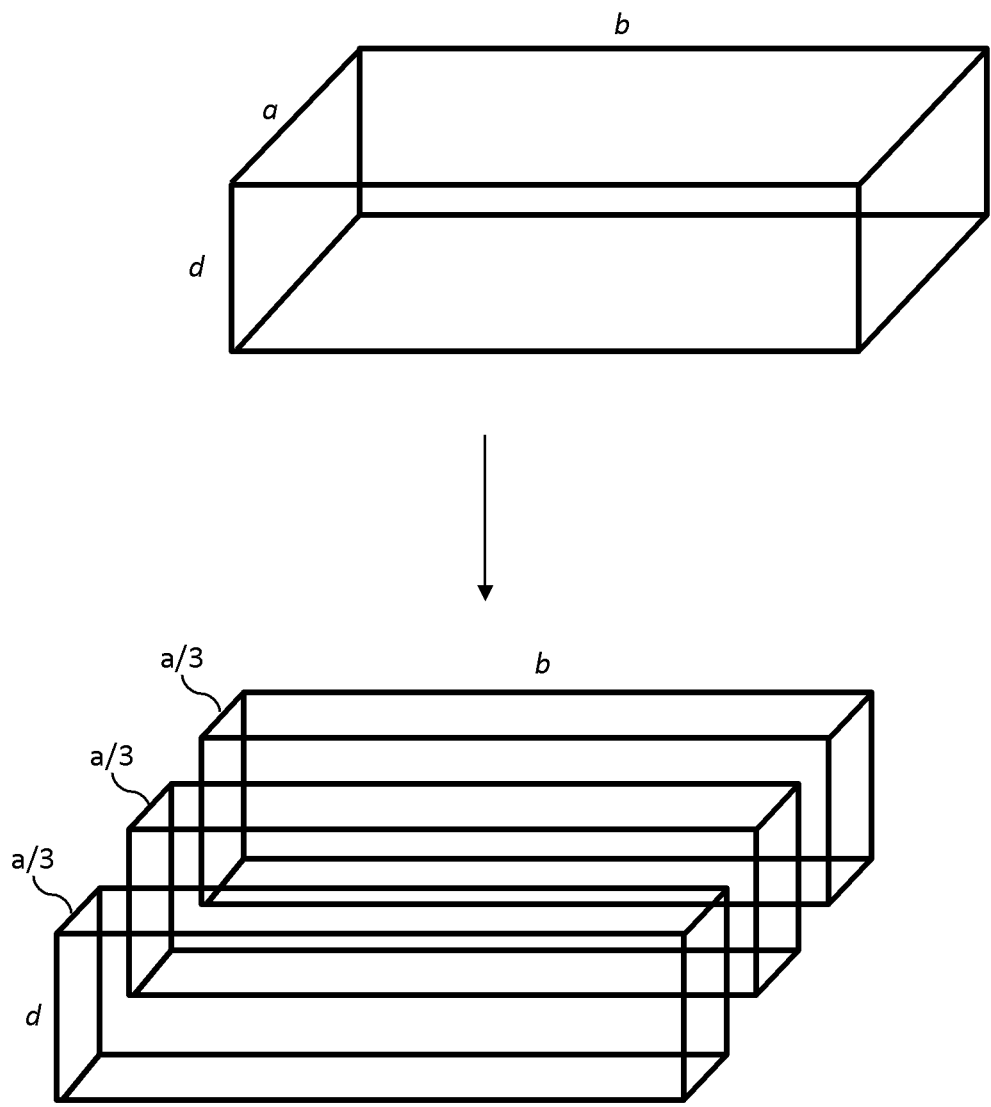
FIG. 8 is a schematic illustration of a division of each B-scan in a sequence of B-scans into sets of adjacent A-scans and a subsequent concatenating of resulting corresponding sets of A-scans to obtain respective sections of a sequence of B-scans.

The image data discussed above represents data that has been aggregated over the whole of each B-scan, and thus over the whole of the scanned region R. As a further alternative, respective correlations may be computed for each of a plurality of different sections of the scanned region R of the retina (with each section comprising a different respective set of A-scans), and these correlations may be mapped to an en-face representation of the retina, either as a diagram or as a retinal image such as a fundus image, a scanning laser ophthalmoscope (SLO) image or an en-face OCT image, for example. In other words, the rolling window correlation described above may be calculated separately for each of two or more sections of the sequence of B-scans 500, which are obtained by dividing each B-scan in the sequence of B-scan 500 in the same way, into two or more sets of adjacent A-scans, and concatenating the resulting corresponding sets of A-scans to obtain the respective sections of the sequence of B-scans 500, as illustrated in FIG. 8 (where the B-scans are divided into three equally-sized sections in the A-scan direction, by way of an illustrative example, although there may more generally be more or fewer sections, which need not have the same number of A-scans).

The image data may thus additionally or alternatively define an image which indicates a spatial variation, in the scanned region R of the retina 10, of the one or more properties of the response curve mentioned above (for example), the spatial variation being overlaid on an en-face representation of at least a portion the retina which includes the scanned region R. The correlations calculated for the different sections of the scanned region R may be coloured in accordance with any appropriate colour scheme to indicate one or more of the following, for example: (i) the value of one of the markers in each of the sections; (ii) which of a predefined set of intervals the marker in each of the sections belongs to, based on a reference database, e.g. green for a part of the scanned region of the retina that has provided a signal which corresponds to a marker "amplitude of the difference between the first and second peak" whose value is within the 95% confidence interval of a population of healthy eyes; (iii) the percentage of the correlation values on the response curve that adheres to the confidence interval of a reference set of either healthy eyes or eyes with a specific disease; or (iv) aggregate values from the response curve, such as maximum, minimum, mean or median over time, where a darker hue or more red colour is higher than a lighter hue or more blue/green colour, for example.

Figure 9:
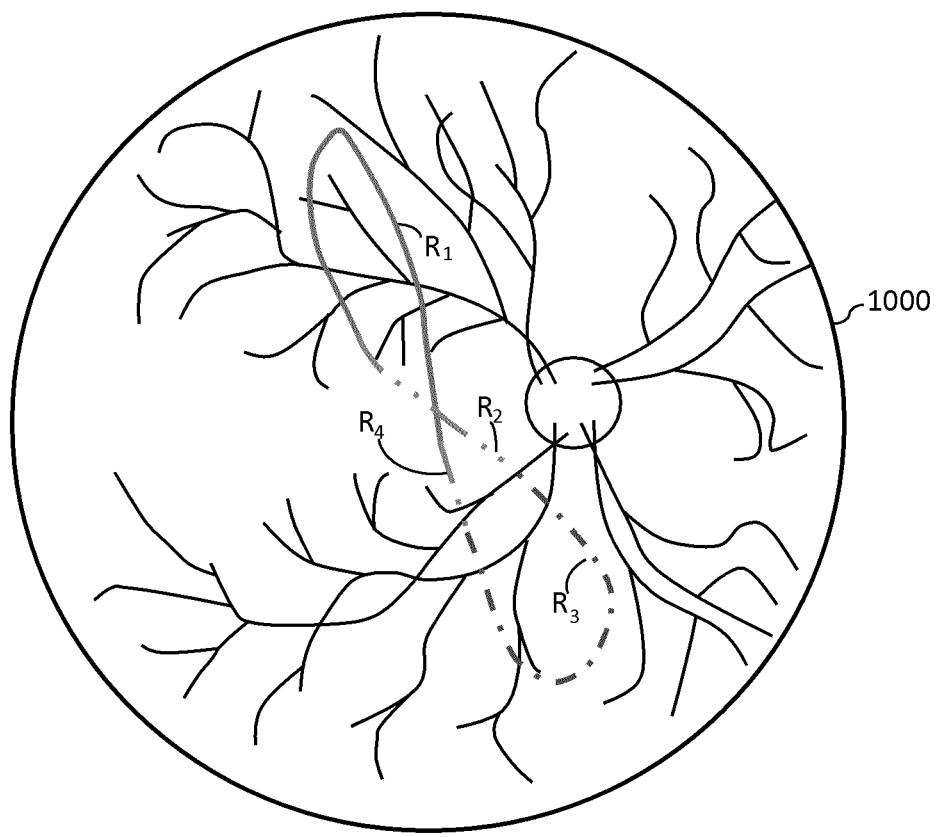
FIG. 9 is an example illustration of an image indicating respective correlation strengths calculated for each of four different sections of a scanned region of a retina, which are overlaid on a representation of the retina.

FIG. 9 is an example illustration of an image indicating respective correlation strengths calculated for each of four different sections, $R_1$, $R_2$, $R_3$, and $R_4$, of the scanned region R of the retina 10 (using four corresponding sections of the sequence of B-scans 500), which are overlaid on a representation 1000 of the retina 10. Where the scan has taken place, different colours and hues may be used to indicate one of options (i) to (iv) listed above, for example. In the example of FIG. 9, the scan pattern on the retina resembles the shape of a figure of 8, although other scan patterns could alternatively be used.

The image which indicates the overlay of the spatial variation (in the scanned region R) of the one or more properties of the response curve onto an en-face representation may be turned into an animation by showing how the correlation strength varies over time at each scan location in the scanned region R shown in the image. Colours and hue may be used to represent the amplitude of the correlation strength and sign by converting either the absolute strength or the normalised strength values to different hues, e.g. darker hues to illustrate a stronger signal, and different colours, e.g. blue for positive correlation and red for negative correlation, for example.

Figure 10:
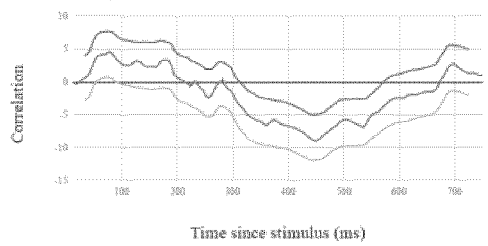
FIG. 10 is an example of a functional OCT report defined by image data which may be generated by an image data generation module of the first example embodiment herein.
Figure 10:
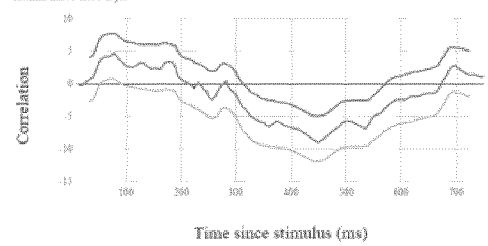
Figure 10:
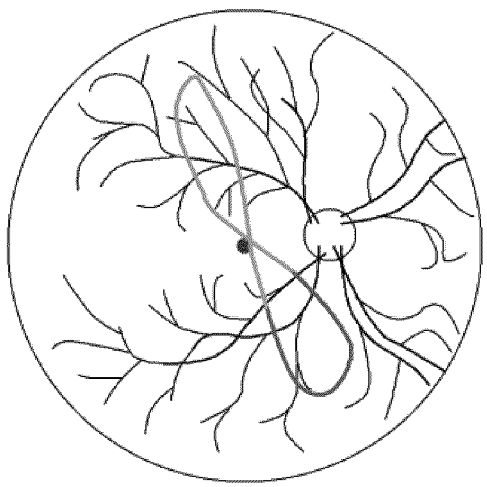
Figure 10:
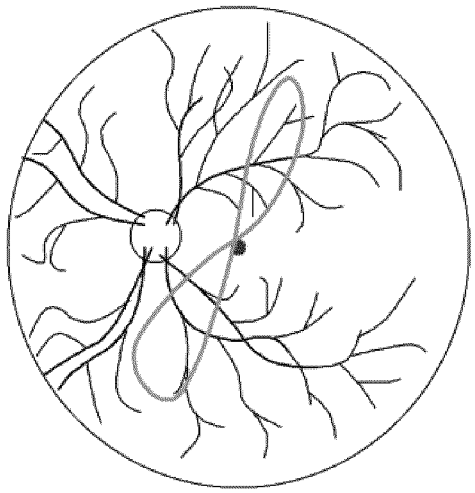

The image data may define an image which is indicative of retinal responses derived from two separate functional OCT data sets, for example first set of functional OCT data that has been acquired from an eye, and a second set of functional OCT data that has subsequently been acquired from the same eye, the image allowing corresponding responses of the retina to be compared to one another. The image data generator 130 may generate image data that allows two main forms of results to be displayed, as follows: (i) retinal responses based on the first and second sets of functional OCT data, which may be presented in the same (or same kind of) graph or table in order to enable the healthcare practitioner to see the absolute values 'side by side'—this is applicable to both the correlation strength variations over time (which may, for example, be plotted on a graph) and the derived markers (which may, for example, be presented in columns or rows of a table); and (ii) the difference or a ratio between the retinal responses based on the first and second sets of functional OCT data. Colour and hue may be used to show the magnitude and sign (e.g. red for negative and blue for positive) of the difference, for example. An example of a functional OCT report defined by such image data is illustrated in FIG. 10.

Embodiment 2

In the first example embodiment, the correlation calculator module 120-1 is configured to calculate the rolling window correlation between the sequence of B-scans 500 and the sequence S of stimulus indicators received from the OCT imaging device 200, and to subsequently process the resulting three-dimensional array 700 of correlation values (in step S40 of FIG. 5) so as to generate a two-dimensional array 800 of correlation values, by taking the average of the correlation values in the depth (d) direction. However, the averaging operation may, as in the present example embodiment, alternatively be performed on the B-scans prior to their correlation with the sequence S of stimulus indicators, thereby simplifying and speeding up the correlation calculation.

Figure 11:
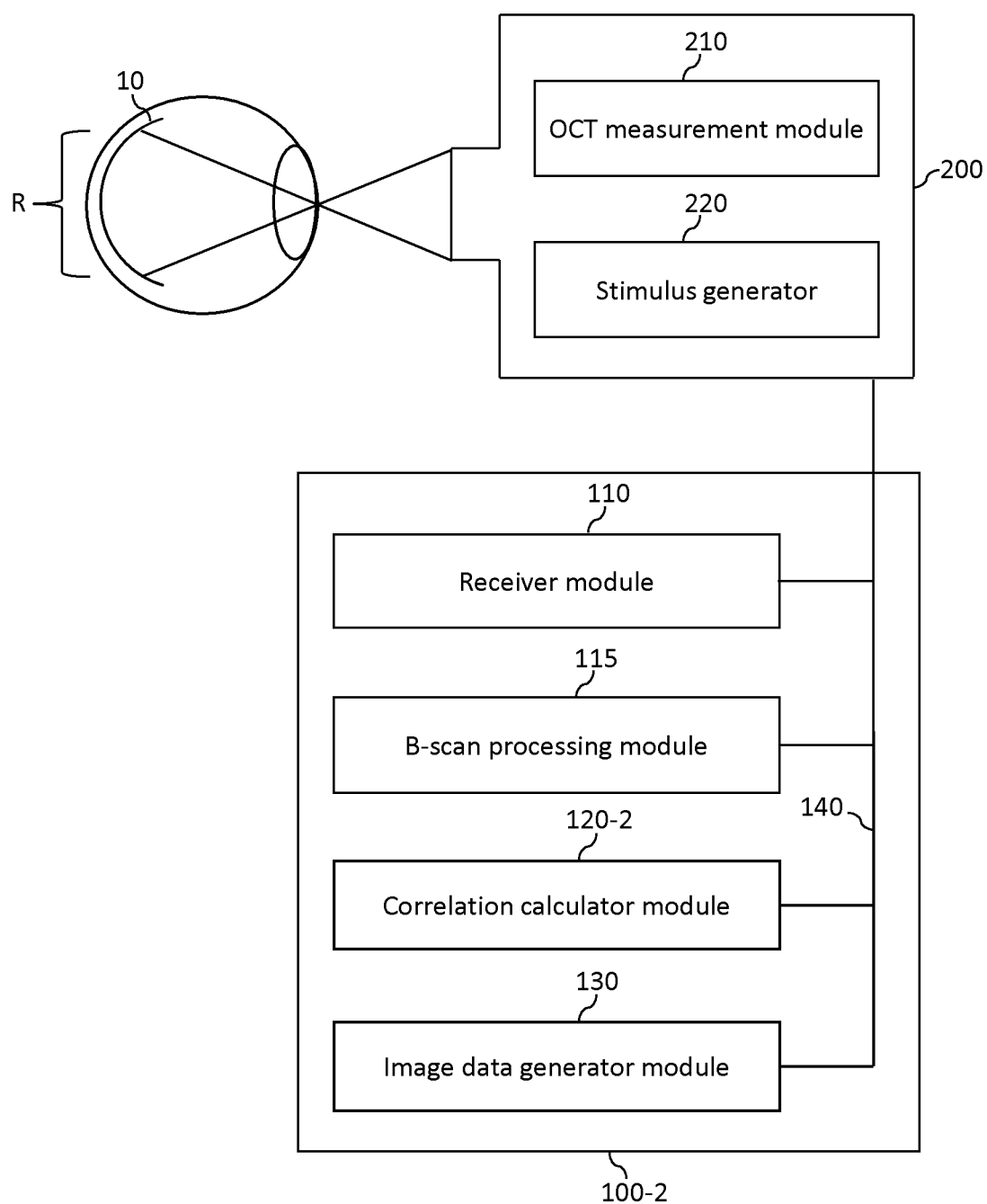
FIG. 11 is a schematic illustration of an apparatus for processing functional OCT image data according to a second example embodiment herein.

FIG. 11 is a schematic illustration of an apparatus 100-2 according to the second example embodiment, which comprises, in addition to the receiver module 110 and the image data generator module 130 that are the same as those in apparatus 100-1, a B-scan processing module 115 and a correlation calculator module 120-2. The apparatus 100-2 of the present example embodiment thus differs from the apparatus 100-1 of the first example embodiment only by comprising the B-scan processing module 115, and the correlation calculator module 120-2, whose functionality differs from that of the correlation calculator module 120-1 of the first example embodiment (as explained in more detail below). The following description of the second example embodiment will therefore focus on these differences, with all other details of the first example embodiment, which are applicable to the second example embodiment, not being repeated here for sake of conciseness. It should be noted that the variations and modifications which may be made to the first example embodiment, as described above, are also applicable to the second embodiment. It should also be noted that one or more of the illustrated components of the apparatus 100-2 may be implemented in the form of a programmable signal processing hardware as described above with reference to FIG. 2, or alternatively in the form of non-programmable hardware, such as an application-specific integrated circuit (ASIC).

Figure 12:
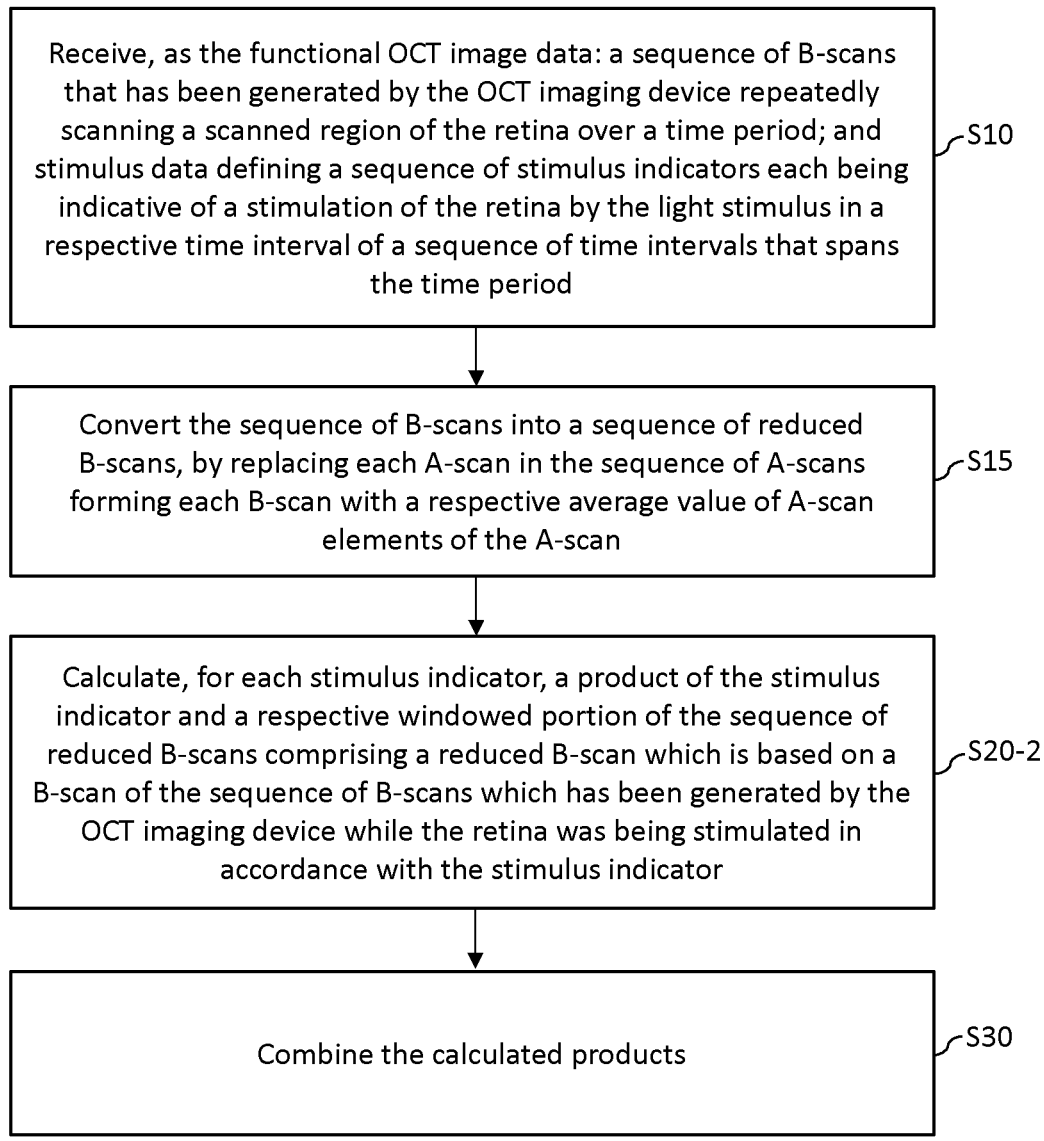
FIG. 12 is a flow diagram illustrating a method of processing functional OCT image data, which has been acquired by an OCT imaging device scanning the subject's retina while the retina is being repeatedly stimulated by the light stimulus, to generate an indication of a response of the retina to the light stimulus in the second example embodiment herein.

FIG. 12 is a flow diagram illustrating a method by which the apparatus 100-2 of the second example embodiment processes functional OCT data to generate an indication of a response of the retina 10 to the light stimulus.

In step S10 of FIG. 12 (which is same as step S10 in FIG. 3), the receiver module 110 receives from the OCT imaging device 200, as the functional OCT image data: (i) OCT image data (specifically, in the form of a sequence of B-scans 500) that has been generated by the OCT imaging device 200 repeatedly scanning the scanned region R of the retina 10 over a time period T; and (ii) stimulus data defining the sequence of s stimulus indicators, each indicative of a stimulation of the retina by the light stimulus in a respective time interval, T/s, of a sequence of time intervals that spans the time period T.

Figure 13:
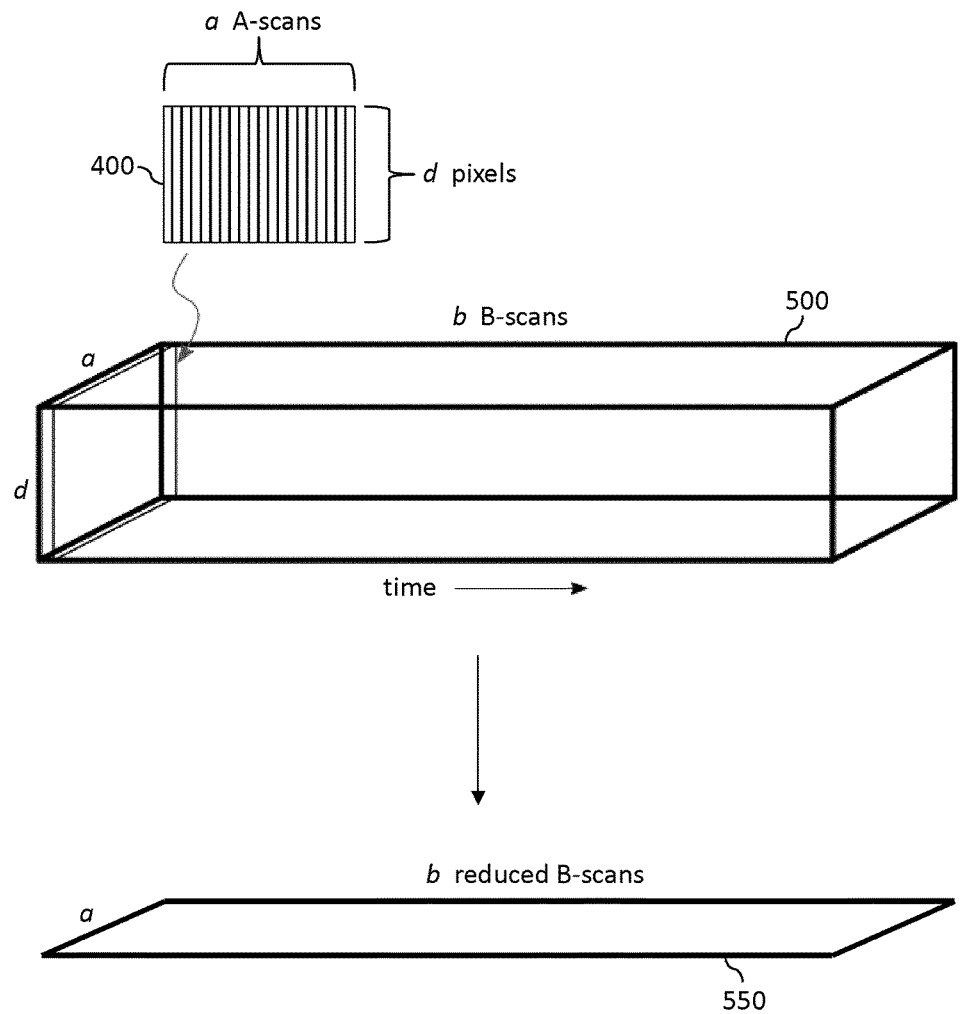
FIG. 13 is a schematic illustration of a conversion of a sequence of B-scans into a sequence of reduced B-scans by a B-scan processing module 115 in the second example embodiment herein.

In step S15 of FIG. 12, the B-scan processing module 115 converts the sequence of B-scans 500 received by the receiver module 110 in step S10 into a sequence of reduced B-scans 550, by replacing each A-scan in the sequence of A-scans forming each B-scan 400 with a respective average value of A-scan elements of the A-scan, as illustrated in FIG. 13.

In step S20-2 of FIG. 12, the correlation calculator module 120-2 calculates the rolling window correlation between reduced B-scans in the sequence of reduced B-scans 550 and stimulus indicators $s_1$, $s_2$, $s_3$ . . . in the sequence S of stimulus indicators by calculating, for each of the stimulus indicators, a product of the stimulus indicator and a respective windowed portion of the sequence of reduced B-scans 550, which may begin with a reduced B-scan that is based on a B-scan of the sequence of B-scans 500 which has been generated by the OCT imaging device 200 while the retina 10 was being stimulated in accordance with the stimulus indicator, and include a predetermined number of subsequent reduced B-scans in the sequence of reduced B-scans 550.

In step S30 of FIG. 12, the correlation calculator module 120-2 combines the calculated products to generate, as the indication of the response of the retina 10 to the light stimulus, a two-dimensional array of correlation values (as shown at 800 in FIG. 6(a)) indicating the response of the retina 10 to the light stimulus as a function of location in the scanned region R of the retina 10 and time.

The two-dimensional array 800 of correlation values may be processed by the image data generator module 130 to generate image data in the same way as in the first example embodiment, and/or the correlation calculator module 120-2 may pre-process the two-dimensional array 800 of correlation values and/or convert the two-dimensional array of correlation values (or the normalised two-dimensional array of correlation values, as the case may be) to a sequence of correlation values in the same way as the correlation calculator module 120-1 of the first example embodiment. The sequence of correlation values may further be processed by the image data generator module 130 to generate image data in the same way as in step S60 of the first example embodiment.

Embodiment 3

The processing of functional OCT data that is performed by the apparatus 100-1 of the first example embodiment allows an indication of the functional response of a scanned region R of the retina 10 to be obtained, based on a correlation which is computed for the whole retinal depth covered by the scan. However, it may be valuable for determining disease diagnosis, for example, to be able to generate an indication of the individual functional responses of one or more retinal layers corresponding to different cell types (e.g. photoreceptors, retinal pigment epithelium, retinal nerve fiber layer, etc.). Such enhanced functionality is provided by the apparatus 100-3 of the third example embodiment, which will now be described with reference to FIGS. 14 to 16.

Figure 14:
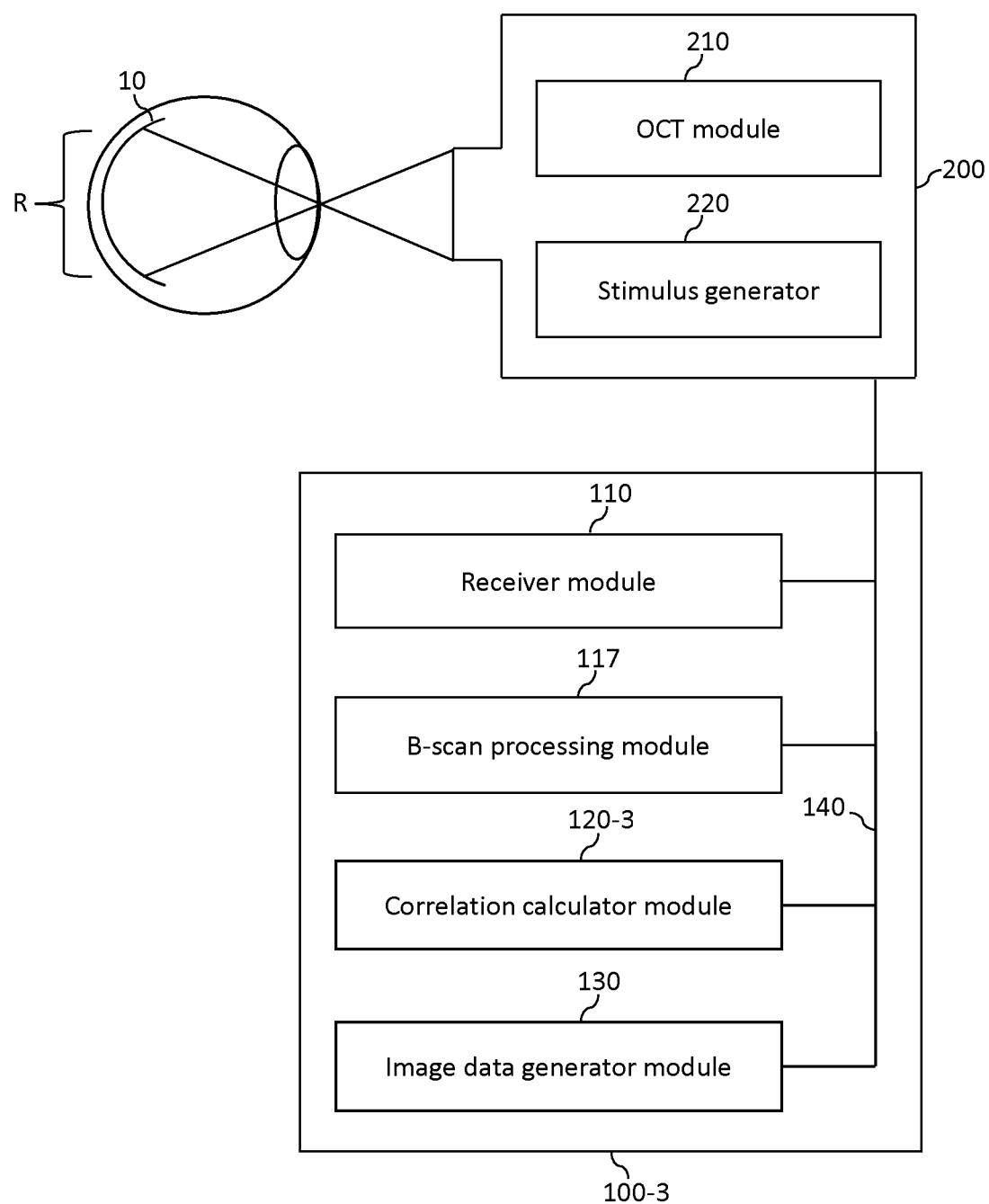
FIG. 14 is a schematic illustration of an apparatus for processing functional OCT image data according to a third example embodiment herein.

FIG. 14 is a schematic illustration of an apparatus 100-3 for processing functional OCT image data to generate an indication of the individual responses of one or more layers of the retina to the light stimulus, according to the third example embodiment. The apparatus 100-3 comprises the same receiver module 110 as the first and second example embodiments, a B-scan processing module 117, a correlation calculator module 120-3, and an image generator module 130 which is the same as that of the first and second example embodiments. It should also be noted that one or more of the illustrated components of the apparatus 100-3 may be implemented in the form of a programmable signal processing hardware as described above with reference to FIG. 2, or alternatively in the form of non-programmable hardware, such as an application-specific integrated circuit (ASIC). Processing operations performed by the apparatus 100-3 will now be described with reference to FIG. 15.

Figure 15:
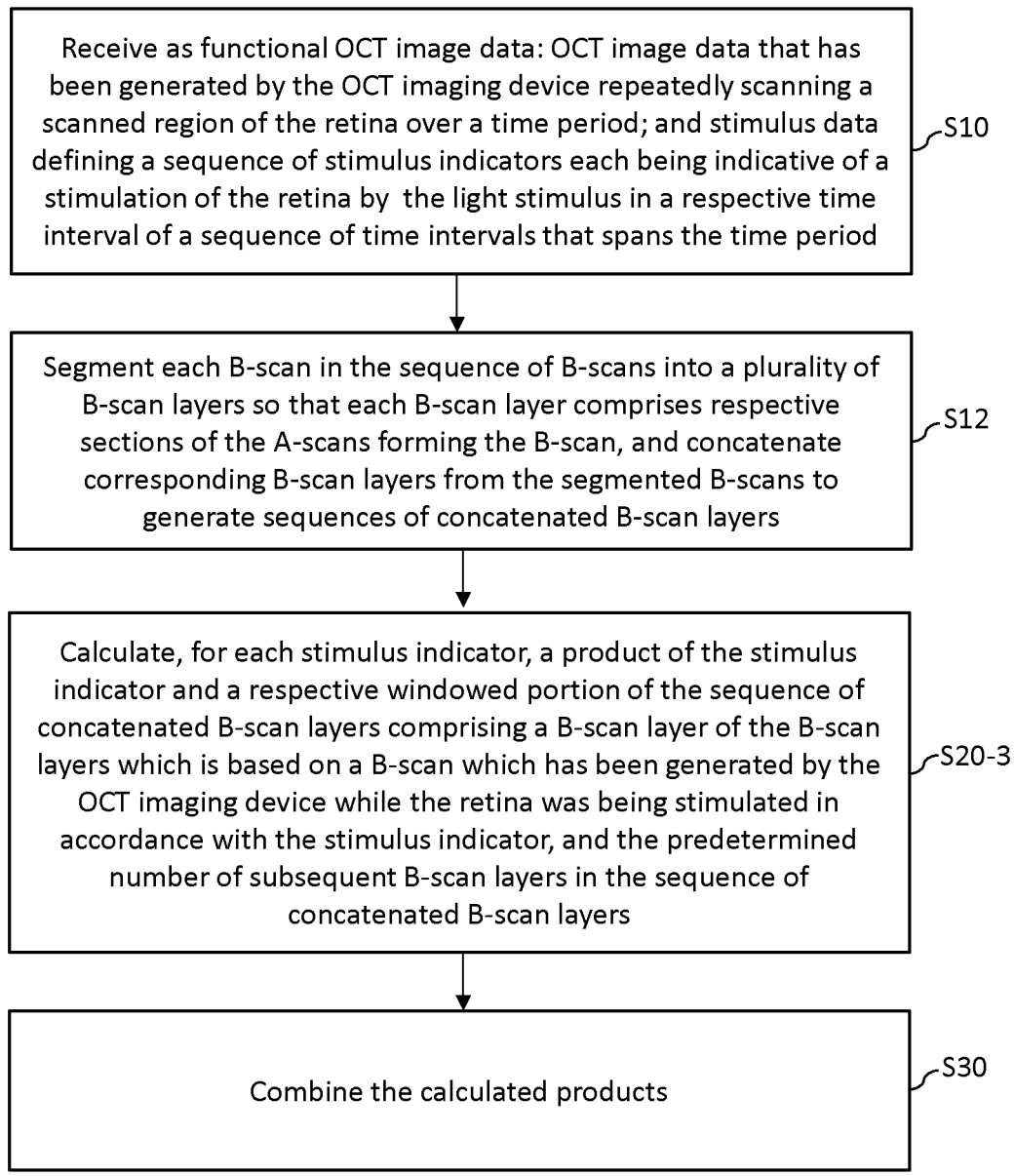
FIG. 15 is a flow diagram illustrating a method of processing functional OCT image data, which has been acquired by an OCT imaging device scanning the subject's retina while the retina is being repeatedly stimulated by the light stimulus, to generate an indication of a response of a layer of the retina to the light stimulus in the third example embodiment herein.

FIG. 15 is a flow diagram illustrating a method by which the apparatus 100-3 of the third example embodiment processes functional OCT data to generate an indication of the response of one or more layers of the retina 10 to the light stimulus.

In step S10 of FIG. 15, the receiver module 110 receives functional OCT image data from the OCT imaging device 200. Step S10 in FIG. 15 is the same as step S10 in FIG. 3, and will therefore not be described in further detail here.

Figure 16:
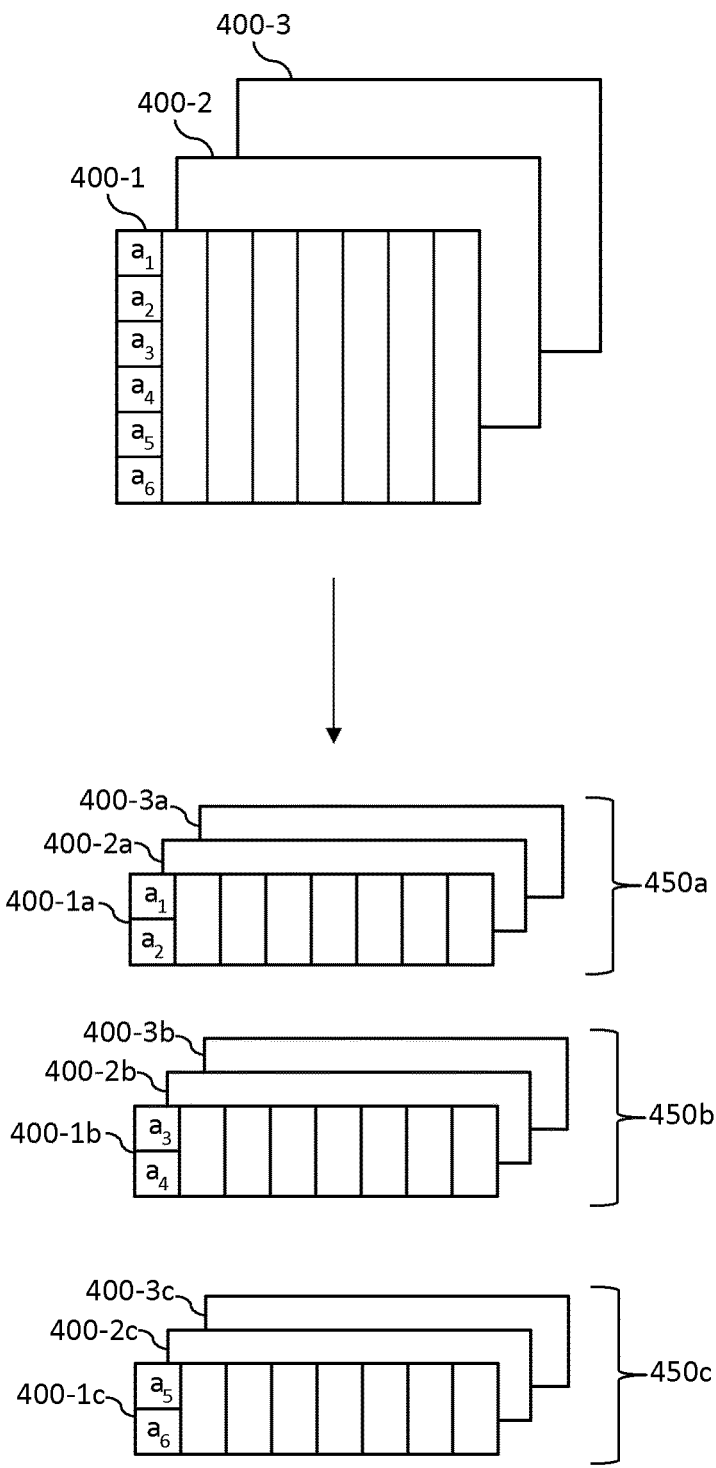
FIG. 16 is a schematic illustration of a segmentation of B-scans by a B-scan processing module 117 into B-scan layers in the third example embodiment herein.

In step S12 of FIG. 15, the B-scan processing module 117 identically segments each B-scan 400 in the sequence of B-scans 500 into a plurality of B-scan layers, so that each B-scan layer comprises respective sections of the A-scans forming the B-scan 400. In other words, as illustrated in FIG. 16, the B-scan processing module 117 divides a first B-scan 400-1 in the sequence of B-scans 500 into a plurality of layers (or segments) 400-1a, 400-1b and 400-1c in the depth direction, so that each layer comprises a respective set of a A-scan sections, divides a second B-scan 400-2 in the sequence of B-scans 500 into a plurality of layers (or segments) 400-2a, 400-2b and 400-2c in the depth direction, so that each layer comprises a respective set of a A-scan sections, and so on. It should be noted that the segmentation of the B-scans by the B-scan processing module 117 into three equal layers in FIG. 16 is given by way of example only, and that the B-scans may be segmented into a greater or smaller number of B-scan layers. It should also be noted that the number of A-scan elements in the columns of the B-scan layers need not be the same; in other words, the B-scan layers may have different respective thicknesses.

The B-scan processing module 117 further concatenates corresponding B-scan layers (i.e. B-scan layers from different B-scans, which B-scan layers contain respective sets of OCT measurement results derived from the same range of depths from the retinal surface) from the segmented B-scans to generate sequences of concatenated B-scan layers. Thus, as illustrated in FIG. 16, the B-scan processing module 117 concatenates B-scan layers 400-1a, 400-2a, 400-3a, . . . etc. to generate a first sequence of concatenated B-scan layers, 450a, which corresponds to a first layer of the retina 10, concatenates B-scan layers 400-1b, 400-2b, 400-3b, . . . etc. to generate a second sequence of concatenated B-scan layers, 450b, which corresponds to a second (deeper) layer of the retina 10, and concatenates B-scan layers 400-1c, 400-2c, 400-3c, . . . etc. to generate a third sequence of concatenated B-scan layers, 450c, which corresponds to a third (yet deeper) layer of the retina 10. Each of the sequences of concatenated B-scan layers thus forms a three-dimensional array of A-scan elements, which corresponds to a respective layer of the retina 10.

In step S20-3 of FIG. 15, the correlation calculator module 120-3 calculates, for each of at least one sequence of concatenated B-scan layers of the sequences of concatenated B-scan layers generated in step S12 of FIG. 15, a respective rolling window correlation between concatenated B-scan layers in the sequence of concatenated B-scan layers and stimulus indicators ($s_1$, $s_2$, $s_3$) in the sequence S of stimulus indicators, specifically by calculating, for each stimulus indicator, a product of the stimulus indicator and a respective windowed portion of the sequence of concatenated B-scan layers, comprising a B-scan layer of the B-scan layers which is based on a B-scan 400 which has been generated by the OCT imaging device 200 while the retina 10 was being stimulated in accordance with the stimulus indicator, and the predetermined number, $b_{lag}$, of subsequent B-scan layers in the sequence of concatenated B-scan layers.

In step S30 of FIG. 15, for each of the at least one sequence of concatenated B-scan layers, the correlation calculator module 120-3 combines the products calculated in step S20-3 to generate a respective three-dimensional array of values ("response volume") that provides an indication of a response of the respective layer of the retina (10) to the light stimulus.

Each resulting three-dimensional array of correlation values may further be processed by the correlation calculator module 120-3, and the results of those further processing operations may be used by the image data generator module 130 to generate image data defining an image which indicates the response of the corresponding layer of the retina 10 to the light stimulus for display to a user of the apparatus 100-3, using the further processing operations that have been explained in the above description of the first embodiment, with reference to FIG. 5.

More particularly, the response volume corresponding to each retinal layer may be reduced to a two-dimensional response image for easier visualisation, by taking the average in the depth (d) direction, i.e. one value per A-scan per lag time point. Thus, the correlation calculator module 120-3 may convert each three-dimensional array of correlation values, which is a/3×$b_{lag}$×d pixels in size in the present example embodiment, into a respective two-dimensional array of correlation values, which is a/3×$b_{lag}$ pixels in size, by replacing each one-dimensional array of correlation values in the three-dimensional array, which one-dimensional array has been calculated using sections of A-scans that are identically located in respective B-scans of the sequence of B-scans, with a single value that is an average of the correlation values in the one-dimensional array. Thus, each array element of the one-dimensional array is calculated on the basis of a corresponding element of an A-scan. The two-dimensional array of correlation values indicates the response of the corresponding layer of the retina 10 to the light stimulus as a function of location along the scanned region R of the retina 10 (i.e. as a function of position along the line defining the scan pattern) and time.

The image data generator module 130 may use at least one of the two-dimensional arrays of correlation values to generate image data defining an image which indicates the response, to the light stimulus, of a respective layer of the retina 10 corresponding to each of the at least one of the two-dimensional arrays as a function of location in the scanned region R of the retina 10 and time. However, it may be preferable to pre-process at least some of the two-dimensional arrays of correlation values prior to image data generation (or prior to the alternative further processing operation described below), in order to accentuate the time-dependent variability of the signal, i.e. the variation of the retinal layer response to light stimulation over time. Such pre-processing may be desirable in cases where the response variability in the A-scan direction is greater than in the time lag direction.

The correlation calculator module 120-3 may pre-process one or more of the two-dimensional arrays of correlation values, each comprising a sequence of $b_{lag}$ one-dimensional arrays, each indicating the response of the corresponding layer of the retina 10 to the light stimulus as a function of location in the scanned region R of the retina 10, to generate a normalised two-dimensional array of correlation values. The correlation calculator module 120-3 may generate the normalised two-dimensional array of correlation values by subtracting the first one-dimensional array in the sequence of one-dimensional arrays from each remaining one-dimensional array in the sequence of one-dimensional arrays. Alternatively, the correlation calculator module 120-3 may generate a normalised two-dimensional array of correlation values by calculating an array of averaged correlation values, such that each averaged correlation value in the array of averaged correlation values is an average (mean) of the correlation values that are correspondingly located in the sequence of one-dimensional arrays, and subtracting the calculated array of averaged correlation values from each of the one-dimensional arrays in the sequence of one-dimensional arrays (in other words, performing a vector subtraction of the calculated array of averaged correlation values from each of the one-dimensional arrays). In both of these alternative ways of calculating normalised two-dimensional array of correlation values, the resulting normalised two-dimensional array of correlation values indicates the response of the corresponding layer of the retina to the light stimulus as a function of location in the scanned region R of the retina 10 and time. The image data generator module 130 may use each normalised two-dimensional array of correlation values to generate image data defining an image that indicates the response of the corresponding layer of the retina 10 to the light stimulus as a function of location in the scanned region R of the retina 10 and time.

To allow the response of one or more layers of the retina 10 to the light stimulus to be illustrated in a form that may be more useful for a healthcare practitioner or other user, the correlation calculator module 120-3 may convert the two-dimensional array of correlation values (or the normalised two-dimensional array of correlation values, as the case may be) corresponding to each of one or more of the retinal layers to a sequence of correlation values by replacing each of the one-dimensional arrays of correlation values in the two-dimensional array (each of the one-dimensional arrays indicating the response of the corresponding layer of the retina 10 to the light stimulus as a function of location along the scanned region R of the retina 10) with a single respective value that is an average of the correlation values in the one-dimensional array, each sequence of correlation values indicating a response of the respective layer of the retina 10 in the scanned region R to the light stimulus as a function of time.

The image data generator module 130 may use one or more of the sequences of correlation values to generate image data defining an image that indicates the response of the respective one or more layers of the retina 10 in the scanned region R of the retina 10 to the light stimulus.

Similar to the first and second example embodiments described above, the image data generator module 130 may use one or more sequences of correlation values to generate an image which indicates at least one of: the response of the respective one or more layers of the retina 10 in the scanned region R to the light stimulus as a function of time; one or more properties of a respective one or more curves defining the response of the respective one or more layers of the retina 10 in the scanned region R to the light stimulus as a function of time; and a spatial variation, in the scanned region R of the retina 10, of one or more properties of the respective one or more curves defining the response of the respective one or more layers of the retina 10 in the scanned region R to the light stimulus as a function of time, the spatial variation being overlaid on an en-face representation of at least a portion the retina 10 which includes the scanned region R.

Embodiment 4

In the third example embodiment, the correlation calculator module 120-3 is, in one configuration, configured to calculate, for each of at least one sequence of concatenated B-scan layers of the concatenated sequences of B-scan layers, a respective rolling window correlation between the sequence of concatenated B-scan layers and the sequence S of stimulus indicators received from the OCT imaging device 200, and to subsequently process the resulting three-dimensional array of correlation values to generate a two-dimensional array of correlation values, by taking an average of the correlation values in the depth (d) direction. However, the averaging operation may, as in the present example embodiment, alternatively be performed on the one or more of the sequences of concatenated B-scan layers prior to their correlation with the sequence S of stimulus indicators, thereby simplifying and speeding up the correlation calculation.

Figure 17:
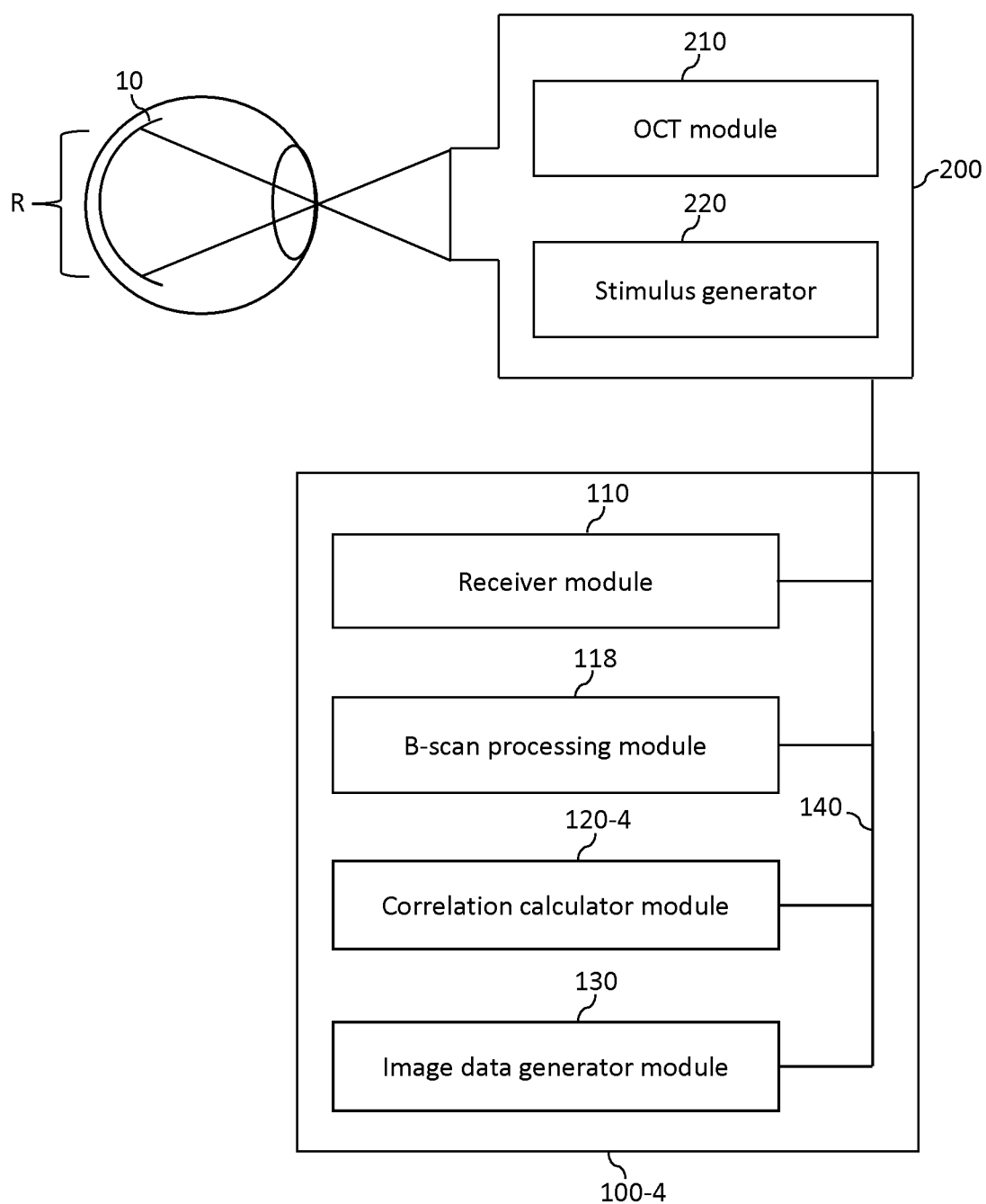
FIG. 17 is a schematic illustration of an apparatus for processing functional OCT image data according to a fourth example embodiment herein.

FIG. 17 is a schematic illustration of an apparatus 100-4 according to the fourth example embodiment, which comprises, in addition to the receiver module 110 and the image data generator module 130 that are the same as those in apparatuses 100-1, 100-2 and 100-3 of the foregoing example embodiments, a B-scan processing module 118 and a correlation calculator module 120-4, which are described in detail below. The B-scan processing module 118 has functionality in common with that the B-scan processing module 117 of the third example embodiment (which will not be described here again), as well as some further functionality which is described below. It should also be noted that one or more of the illustrated components of the apparatus 100-4 may be implemented in the form of a programmable signal processing hardware as described above with reference to FIG. 2, or alternatively in the form of non-programmable hardware, such as an application-specific integrated circuit (ASIC).

Figure 18:
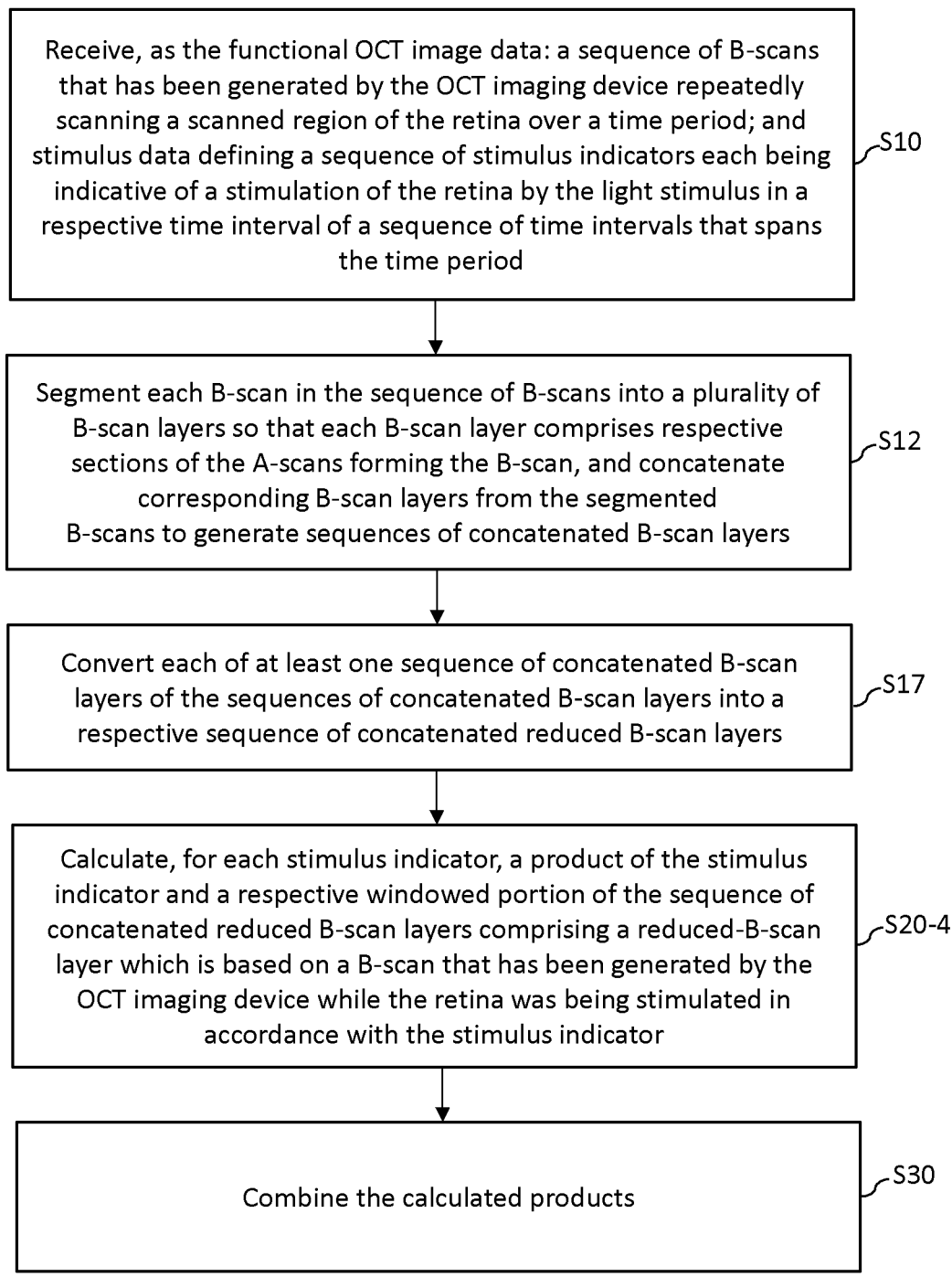
FIG. 18 is a flow diagram illustrating a method of processing functional OCT image data, which has been acquired by an OCT imaging device scanning the subject's retina while the retina is being repeatedly stimulated by the light stimulus, to generate an indication of a response of a layer of the retina to the light stimulus in the fourth example embodiment herein.

FIG. 18 is a flow diagram illustrating a method by which the apparatus 100-4 of the fourth example embodiment processes functional OCT data to generate an indication of a response of the retina 10 to the light stimulus.

In step S10 of FIG. 18, the receiver module 110 receives the functional OCT image data from the OCT imaging device 200. Step S10 in FIG. 18 is the same as step S10 in FIG. 3, and will therefore not be described in further detail here.

In step S12 of FIG. 18, the B-scan processing module 118 identically segments each B-scan 400 in the sequence of B-scans 500 into a plurality of B-scan layers, so that each B-scan layer comprises respective sections of the A-scans forming the B-scan 400. Step S12 in FIG. 18 is the same as step S12 in FIG. 15, and will therefore not be described in further detail here. As in the third example embodiment, each of the sequences of concatenated B-scan layers forms a three-dimensional array of A-scan elements, which corresponds to a respective later of the retina 10.

In step S17 of FIG. 18, the B-scan processing module 118 converts each of at least one of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans. For example, in the illustrative example of FIG. 16, the B-scan processing module 118 converts the three-dimensional array formed by the first sequence of concatenated B-scan layers, 450a, into a two-dimensional array, by replacing the first column of B-scan layer (or segment) 400-1a, comprising A-scan elements a1 and a2, with a single value that is an average of a1 and a2, with the remaining columns of B-scan segment 400-1a, and the other B-scan segments 400-1b, 400-1c, etc. of the first sequence of concatenated B-scan layers 450a are processed in the same way. The B-scan processing module 118 may likewise process the second sequence of concatenated B-scan layers 450b and/or the third sequence of concatenated B-scan layers 450c in addition to, or alternatively to, the first sequence of concatenated B-scan layers 450a. Thus, the B-scan processing module 118 can convert each of one or more of the three-dimensional arrays of OCT measurement values shown in the example of FIG. 16, each of which is $a/3 \times b_{lag} \times d$ pixels in size, into a respective two-dimensional array of values, which is $a/3 \times b_{lag}$ pixels in size.

In step S20-4 of FIG. 18, the correlation calculator module 120-4 calculates, for each of at least one sequence of concatenated reduced B-scan layers of the sequences of concatenated reduced B-scan layers generated in step S17 of FIG. 18, a respective rolling window correlation between reduced B-scan layers in the sequence of concatenated reduced B-scan layers and stimulus indicators ($s_1$, $s_2$, $s_3$) in the sequence S of stimulus indicators, specifically by calculating, for each stimulus indicator, a product of the stimulus indicator and a respective windowed portion of the sequence of concatenated reduced B-scan layers comprising a reduced B-scan layer which is based on a B-scan that has been generated by the OCT imaging device 200 while the retina 10 was being stimulated in accordance with the stimulus indicator, and the predetermined number, $b_{lag}$, of subsequent reduced B-scan layers in the sequence of concatenated reduced B-scan layers.

In step S30 of FIG. 18, for each of the at least one sequence of concatenated reduced B-scan layers, the correlation calculator module 120-4 combines the products calculated in step S20-4 to generate a respective two-dimensional array of values ("response area") that provides an indication of a response of a layer of the retina corresponding to the sequence of concatenated reduced B-scan layers to the light stimulus as a function of location in the scanned region R of the retina 10 and time.

Each resulting two-dimensional array of correlation values may further be processed by the correlation calculator module 120-4 in the same way as the two-dimensional array(s) of correlation values is/are processed by the correlation calculator module 120-3 in the third example embodiment described above.

Thus, the image data generator module 130 may use at least one of the two-dimensional arrays of correlation values to generate image data defining an image which indicates the response, to the light stimulus, of a respective layer of the retina 10 corresponding to each of the at least one of the two-dimensional arrays as a function of location in the scanned region R of the retina 10 and time. However, it may be preferable to pre-process at least some of the two-dimensional arrays of correlation values prior to image data generation (or prior to the alternative further processing operation described below), in order to accentuate the time-dependent variability of the signal, i.e. the variation of the retinal layer response to light stimulation over time. Such pre-processing may be desirable in cases where the response variability in the A-scan direction is greater than in the time lag direction.

The correlation calculator module 120-4 may pre-process one or more of the two-dimensional arrays of correlation values, each comprising a sequence of $b_{lag}$ one-dimensional arrays, each array indicating the response of the corresponding layer of the retina 10 to the light stimulus as a function of location in the scanned region R of the retina 10, to generate a normalised two-dimensional array of correlation values. The correlation calculator module 120-4 may generate a normalised two-dimensional array of correlation values (indicating the response of the corresponding layer of the retina 10 to the light stimulus as a function of location in the scanned region R of the retina 10 and time) using one of the processes described in the third example embodiment, for example. The image data generator module 130 may use each normalised two-dimensional array of correlation values to generate image data defining an image that indicates the response of the corresponding layer of the retina 10 to the light stimulus as a function of location in the scanned region R of the retina 10 and time.

To allow the response of one or more layers of the retina to the light stimulus to be illustrated in a form that may be more useful for a healthcare practitioner such as an ophthalmologist, the correlation calculator module 120-4 may convert the two-dimensional array of correlation values (or the normalised two-dimensional array of correlation values, as the case may be) corresponding to each of one or more of the retinal layers to a sequence of correlation values by replacing each of the one-dimensional arrays of correlation values in the two-dimensional array (each of the one-dimensional arrays indicating the response of the corresponding layer of the retina 10 to the light stimulus as a function of location in the scanned region R of the retina 10) with a single respective value that is an average of the correlation values in the one-dimensional array, each sequence of correlation values indicating a response of the respective layer of the retina 10 in the scanned region to the light stimulus as a function of time.

The image data generator module 130 may use one or more of the sequences of correlation values to generate image data defining an image that indicates the response of the respective one or more layers of the retina 10 in the scanned region R of the retina 10 to the light stimulus.

Similar to the third example embodiment described above, the image data generator module 130 may use one or more sequences of correlation values to generate an image which indicates at least one of: the response of the respective one or more layers of the retina 10 in the scanned region R to the light stimulus as a function of time; one or more properties of a respective one or more curves defining the response of the respective one or more layers of the retina 10 in the scanned region R to the light stimulus as a function of time; and a spatial variation, in the scanned region R of the retina 10, of one or more properties of the respective one or more curves defining the response of the respective one or more layers of the retina 10 in the scanned region R to the light stimulus as a function of time, the spatial variation being overlaid on an en-face representation of at least a portion the retina 10 which includes the scanned region R.

Embodiment 5

Figure 19:
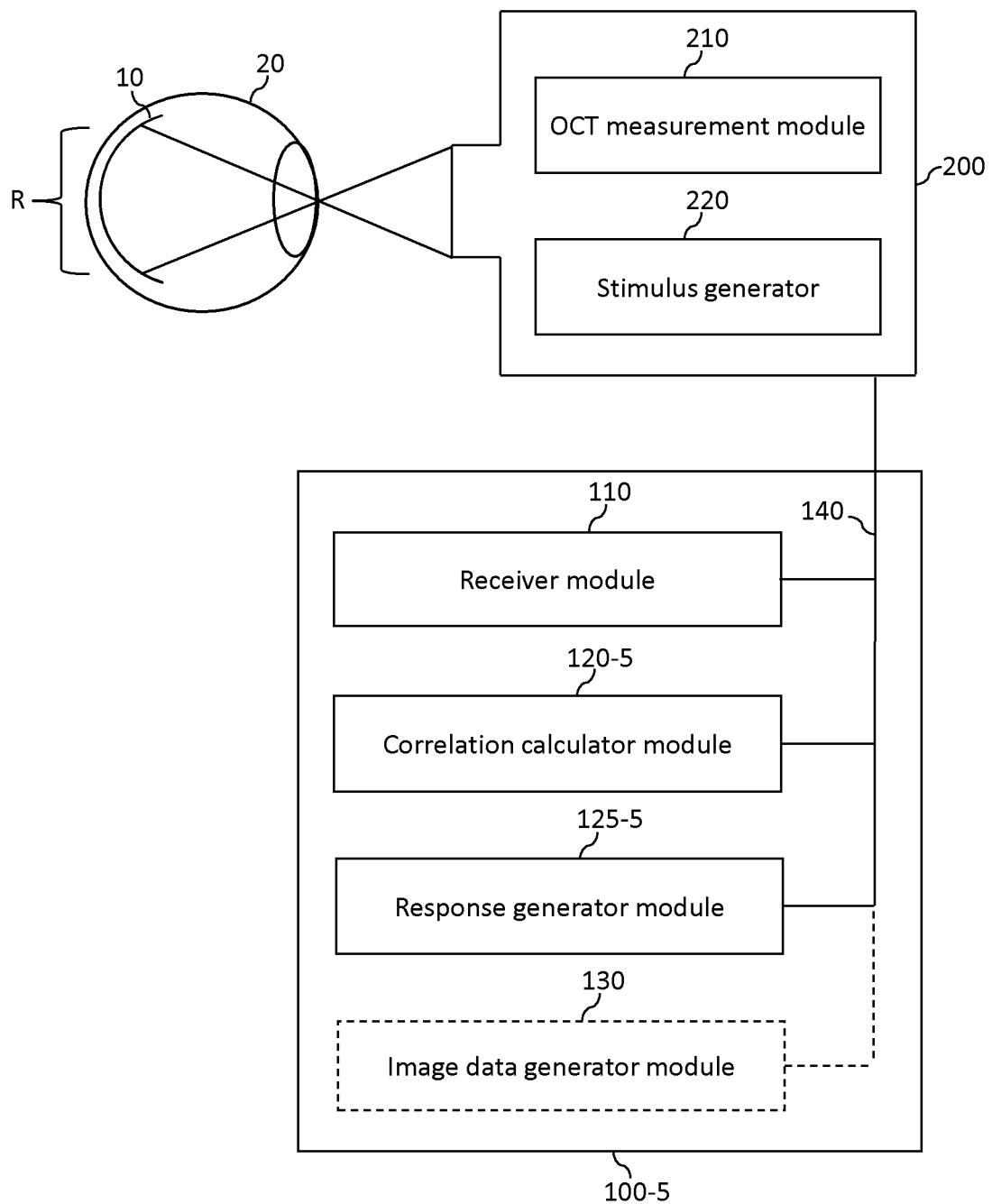
FIG. 19 is a schematic illustration of an apparatus for processing functional OCT image data according to a fifth example embodiment herein.

FIG. 19 is a schematic illustration of an apparatus 100-5 according to a fifth example embodiment, which is configured to process functional OCT image data to generate an indication of how well a retina 10 of a subject's eye 20 responds to a flickering light stimulus. The functional OCT data processed by the apparatus 100-5 is acquired by the OCT imaging device 200, which has already been described above.

The light stimulus may, as in the present example embodiment, comprise a full-field light stimulus (or flash), which provides substantially uniform illumination (at wavelengths in the visible spectrum between about 380 and 740 nm in the present example, although other wavelengths could alternatively or additionally be used) that fills the whole visual field of the subject. The light stimulus generator 220 may, for example, comprise a light-emitting diode (LED) or other optical emitter for generating the light stimuli. The flashes that the light stimulus generator 220 emits may, as in the present example embodiment, give rise to a random (or pseudo-random) stimulation of the retina over time. In other words, the light stimulus generator 220 may emit light flashes that are randomly or pseudo-randomly distributed in time, so that the subject cannot (subconsciously) learn to anticipate upcoming flashes, thereby allowing a more accurate functional response to the subject's retina 10 to light stimulation to be measured.

It should be noted, however, that the light stimulus need not be a full-field stimulus, and may alternatively stimulate only a portion of the retina, which may be illuminated in accordance with a structural scan pattern (e.g. an annulus, a hypotrochoid, or Lissajous figure, for example) by the ophthalmic scanner of the OCT imaging device 200.

As illustrated in FIG. 19, the apparatus 100-5 of the present example embodiment comprises a receiver module 110, a correlation calculator module 120-5, a response generator module 125-5 and, optionally, an image data generator module 130, which are communicatively coupled (e.g. via a bus 140) so as to be capable of exchanging data with one another and with the OCT imaging device 200. The receiver module 110 and the image data generator module 130 are the same as those in the first example embodiment.

As with the preceding example embodiments, the programmable signal processing hardware 300 described above with reference to FIG. 2 may be configured to process functional OCT data using the techniques described herein and, in particular, function as the receiver module 110, the correlation calculator module 120-5, the response generator module 125-5 and the (optional) image data generator module 130 of the fifth example embodiment. It should be noted, however, that the receiver module 110, the correlation calculator module 120-5, the response generator module 125-5 and/or the image data generator module 130 may alternatively be implemented in non-programmable hardware, such as an application-specific integrated circuit (ASIC).

In the present example embodiment, a combination 370 of the hardware components shown in FIG. 2, comprising the processor 320, the working memory 330 and the instruction store 340, is configured to perform functions of the receiver module 110, the correlation calculator module 120-5, the response generator module 125-5 and the image data generator module 130 that are described below.

Figure 20:
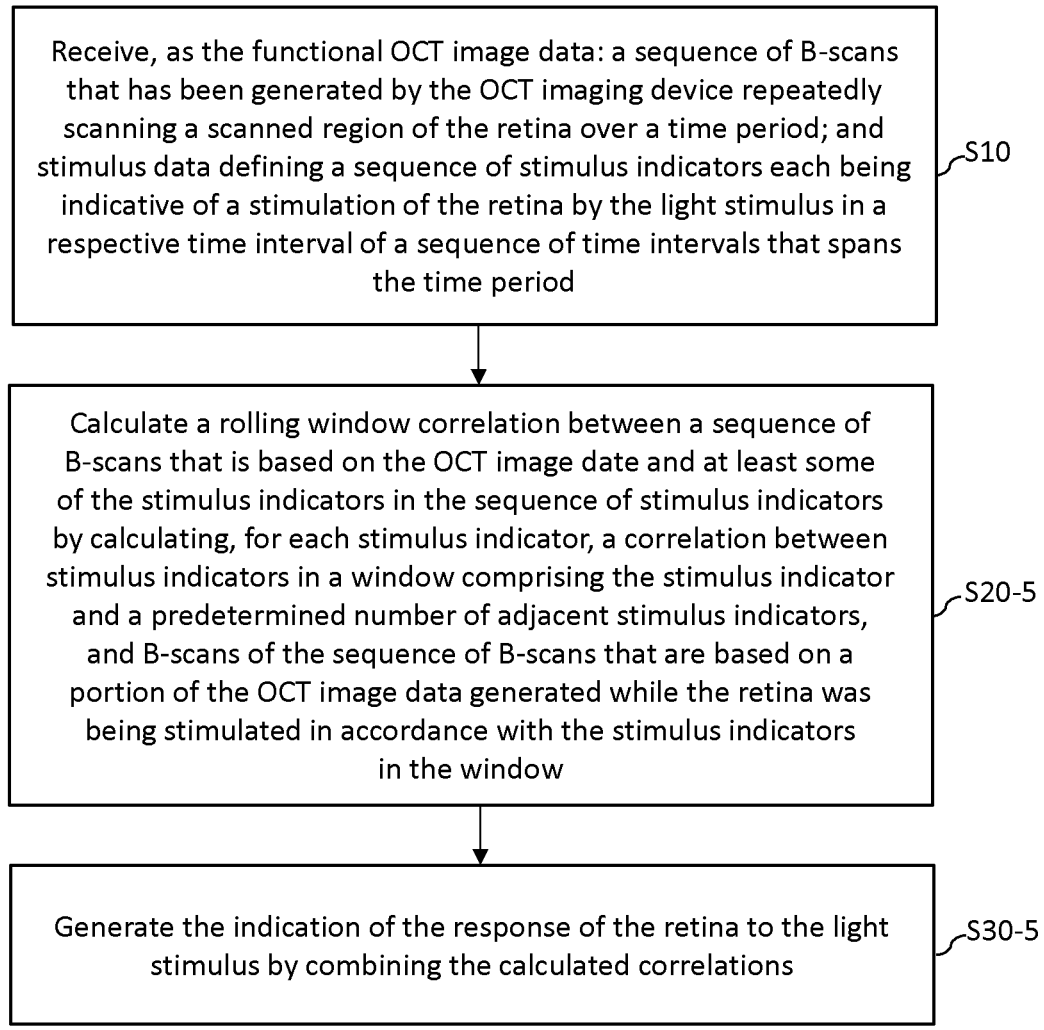
FIG. 20 is a flow diagram illustrating a method of processing functional OCT image data, which has been acquired by an OCT imaging device scanning the subject's retina while the retina is being repeatedly stimulated by the light stimulus, to generate an indication of a response of the retina to the light stimulus in the fifth example embodiment herein.

FIG. 20 is a flow diagram illustrating a method performed by the processor 320, by which the processor 320 processes functional OCT data, which has been acquired by the OCT imaging device 200 scanning the subject's retina 10 while the retina 10 is being repeatedly stimulated by the light stimulus, to generate an indication of a response of the retina 10 to the light stimulus.

In step S10 of FIG. 20, the receiver module 110 receives from the OCT imaging device 200, as the functional OCT image data: (i) OCT image data that has been generated by the OCT imaging device 200 repeatedly scanning a scanned region R of the retina 10 over a time period T; and (ii) stimulus data defining a sequence of s stimulus indicators, each stimulus indicator being indicative of a stimulation of the retina 10 by the light stimulus in a respective time interval, T/s, of a sequence of time intervals that spans the time period T.

The received OCT image data may, as in the present example embodiment, comprise a sequence of b B-scans, which has been generated by the OCT imaging device 200 repeatedly scanning the scanned region R of the retina 10 over the time period T. Referring back to FIG. 4, this figure illustrates functional OCT image data acquired by the receiver module 110 in step S10 of FIG. 20. As illustrated in FIG. 4, each B-scan 400 in the sequence of B-scans can be represented as a 2D image made up of a A-scans (vertical lines). Each A-scan comprises a one-dimensional array of d pixels, where the pixel value of each pixel represents a corresponding OCT measurement result, and the location of each pixel in the one-dimensional array is indicative of the OCT measurement location in the axial direction of the OCT imaging device 200, at which location the corresponding pixel value was measured. The OCT image data can thus be represented as a three-dimensional pixel array 500, which is $a \times b \times d$ pixels in size.

It should be noted that each A-scan in the B-scan 400 may be an average of a number of adjacent A-scans that have been acquired by the OCT imaging device 200. In other words, the OCT imaging device 200 may acquire A-scans having lateral spacing (e.g. along the surface of the retina) which is smaller than the optical resolution of the OCT imaging device 200, and average sets of adjacent A-scans to generate a set of averaged A-scans which make up a B-scans displaying improved signal-to-noise.

The OCT imaging device 200 generates the OCT image data by scanning a laser beam across the scanned region R of the retina 10 in accordance with a predetermined scan pattern, acquiring the A-scans that are to make up each B-scan 400 as the scan location moves over the scanned region R. The shape of the scan pattern on the retina 10 is not limited, and is usually determined by a mechanism in the OCT imaging device 200 that can steer the laser beam generated by the OCT measurement module 210. In the present example embodiment, galvanometer ("galvo") motors, whose rotational position values are recorded, are used to guide the laser beam during the acquisition of the OCT data. These positions can be correlated to locations on the retina 10 in various ways, which will be familiar to those versed in the art. The scan pattern may, for example, trace out a line, a curve, or a circle on the surface of the retina 10, although a lemniscate scan pattern is employed in the present example embodiment. The A-scans acquired during each full period of the scan pattern form one B-scan. In the present example embodiment, all of the b B-scans are recorded in the time period T, such that the time per B-scan is T/b, and the scan pattern frequency is b/T.

During the time period T, while the OCT image data is being generated by the OCT imaging device 200, a stimulus is shown to the subject, which can be a full-field stimulus (substantially the same brightness value over the whole visual field), as in the present example embodiment, or a spatial pattern, where the visual field is divided into e.g. squares, hexagons or more complicated shapes. In the case of a full-field stimulus, at any point in time, the brightness can be denoted, for example, as either "1" (full brightness) or as "−1" (darkness, with no stimulus having been applied). The time period T is divided into a sequence of s time intervals (corresponding to the "stimulus positions" referred to herein), each of size T/s and, for each time interval, there is an associated stimulus indicator ($s_1$, $s_2$, $s_3$ . . . ) which is indicative of a stimulation of the retina 10 by the light stimulus in the respective time interval T/s. Thus, each stimulus indicator in the sequence of stimulus indicators may take a value of either 1 or −1 (although the presence or absence of the stimulus may more generally be denoted by n and −n, where n is an integer). The concatenation of the stimulus indicator values that are indicative of the stimulation of the retina 10 during OCT image data generation is referred to herein as a sequence S of stimulus indicators. One choice for S is an m-sequence, which is a pseudo-random array. In alternative embodiments, in which there is a spatial pattern to the stimulus, each individual field can either display a completely different m-sequence, or a version of one m-sequence that is (circularly) delayed by a specific time, or an inversion of one m-sequence (i.e. when one field shows a 1, another shows a −1 and vice versa). As noted above, the receiver module 110 is configured to receive stimulus data defining the sequence S of stimulus indicators $s_1$, $s_2$, $s_3$, etc. The receiver module 110 may, for example, receive information defining the sequence S of stimulus indicators itself, or alternatively information that allows the sequence S of stimulus indicators to be constructed by the apparatus 100-5.

It should be noted that, although each stimulus indicator in the sequence S of stimulus indicators is indicative of whether or not the retina 10 was stimulated by the light stimulus in the corresponding time interval of duration T/s, the stimulus indicator is not so limited, and may, in other example embodiments, be indicative of a change in stimulation of the retina 10 by the light stimulus that occurs in a respective time interval of the sequence S of time intervals that spans the time period T. For example, in the following description of correlation calculations, each windowed portion of the sequence of B-scans may be multiplied by −1 if the stimulus changes from +1 to −1 in the associated time interval T/s, by +1 if the stimulus changes from −1 to +1 in the associated time interval T/s, and by zero if the stimulus does not change in the time interval.

After at least some of the functional OCT data have been received by the receiver module 110, the correlation calculator 120-5 begins to calculate a rolling window correlation between a sequence of B-scans that is based on the OCT image data and at least some of the stimulus indicators in the sequence S of stimulus indicators.

More particularly, the correlation calculator module 120-5 calculates the rolling window correlation by calculating, in step S20-5 of FIG. 20, for each of the stimulus indicators $s_1$, $s_2$, $s_3$, etc., a respective correlation between stimulus indicators in a window comprising the stimulus indicator and a predetermined number of adjacent stimulus indicators, and B-scans of the sequence of B-scans 500 that are based on a portion of the OCT image data generated while the retina 10 was being stimulated in accordance with the stimulus indicators in the window. By way of an example, the correlation calculator module 120-5 of the present example embodiment calculates, for each of the stimulus indicators, a correlation between stimulus indicators in a windowed portion of the sequence S consisting of a stimulus indicator located at a predetermined sequence position in the windowed portion (e.g. the first stimulus indicator in the windowed portion), and a predetermined number of adjacent (e.g. subsequent) stimulus indicators, and corresponding B-scans of the sequence of B-scans 500 that are based on a portion of the OCT image data generated while the retina 10 was being stimulated in accordance with the stimulus indicators in the window.

As noted above, the intervals T/b and T/s are not necessarily equal, and there are b/s B-scans per stimulus position/indicator, or s/b stimuli per B-scan. By way of an example, b/s=2 in the present example embodiment, so that two B-scans are generated by the OCT imaging device 200 while the retina 10 is being stimulated, or is not being stimulated (as the case may be), in accordance with each stimulus indicator value.

Figure 21:
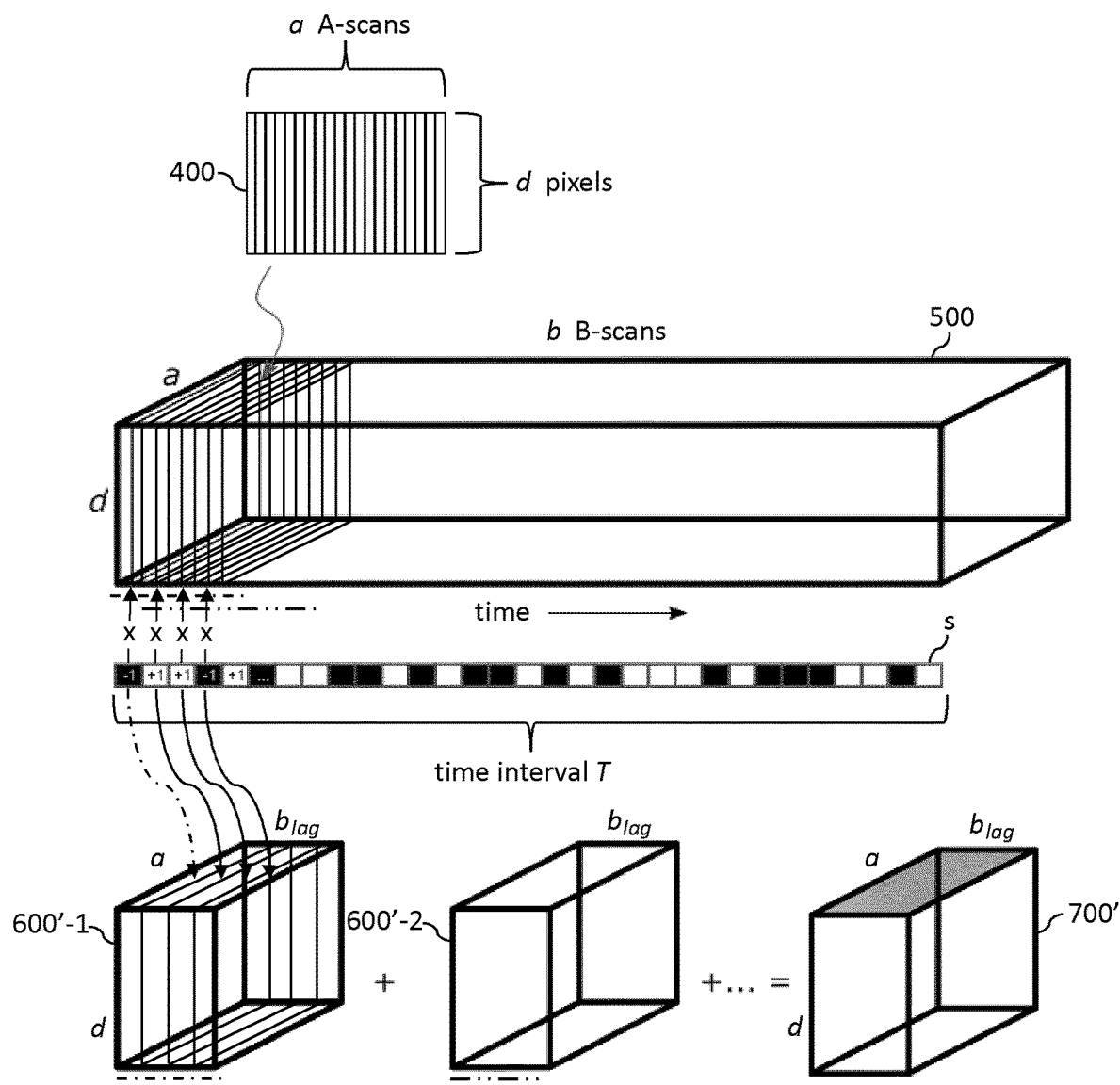
FIG. 21 is a schematic illustration of functional OCT image data acquired by the receiver module 110 in step S10 of FIG. 3, and results of processing the functional OCT image data in the fifth example embodiment herein.

FIG. 21 is a schematic illustration of functional OCT image data acquired by the receiver module 110 in step S10 of FIG. 20, and results of processing the functional OCT image data in the fifth example embodiment herein.

As illustrated in FIG. 21, the correlation calculator module 120-5 calculates a product of the value of the first stimulus indicator $s_1$ in the first windowed portion of stimulus indicators (the first windowed portion further comprising stimulus indicators $s_2$, $s_3$ and $s_4$), which is −1 in the example of FIG. 21, and each of the data elements in the first two B-scans of a first portion (or block) of the three-dimensional array of pixels 500, which portion is a×2×d pixels in size, the first two B-scans having been generated by the OCT imaging device 200 while the retina 10 was not being stimulated, in accordance with the stimulus indicator ($s_1$) value "−1" applicable for the time interval from time t=0 to t=T/s. The correlation calculator module 120-5 also calculates a product of the value of the second stimulus indicator $s_2$ in the first windowed portion of stimulus indicators, which is +1 in the example of FIG. 21, and each of the data elements in the second pair of B-scans of the first portion of the three-dimensional array of pixels 500, the second pair of B-scans having been generated by the OCT imaging device 200 while the retina 10 was being stimulated, in accordance with the stimulus indicator ($s_2$) value "+1" applicable for the time interval from time t=T/s to t=2T/s. The correlation calculator module 120-5 similarly calculates a product of the value of the third stimulus indicator $s_3$ in the first windowed portion of stimulus indicators, which is also +1 in the example of FIG. 21, and each of the data elements in the third pair of B-scans of the first portion of the three-dimensional array of pixels 500, the third pair of B-scans having been generated by the OCT imaging device 200 while the retina 10 was being stimulated, in accordance with the stimulus indicator ($s_3$) value "+1" applicable for the time interval from time t=2T/s to t=3T/s. Likewise, the correlation calculator module 120-5 calculates a product of the value of the fourth stimulus indicator $s_4$ in the first windowed portion of stimulus indicators, which is −1 in the example of FIG. 21, and each of the data elements in the fourth pair of B-scans of the first portion of the three-dimensional array of pixels 500, the fourth pair of B-scans having been generated by the OCT imaging device 200 while the retina 10 was not being stimulated, in accordance with the stimulus indicator ($s_4$) value "−1" applicable for the time interval from time t=3T/s to t=4T/s. The number of stimulus indicators in the window is, of course, not limited to four, and is preferably chosen so that the corresponding number of B-scans, $b_{lag}$, generated by the OCT imaging device 200 corresponds to a period of no more than about 1 second, as the use of greater values of $b_{lag}$ may make little or no improvement to the calculated retinal response, whilst making the calculation more demanding of computational resources. The result of multiplying each stimulus indicator in the window with respective B-scans in the sequence of B-scans is represented by partial response block 600'-1 illustrated in FIG. 21.

This multiplication process is repeated for the remaining stimulus indicators in the sequence S of stimulus indicators, with the correlation calculator module 120-5 moving the rolling window forward in time by one time interval T/s in each step of the process, so that it slides past the second stimulus indicator, $s_1$, in the sequence S of stimulus indicators and covers the stimulus indicator immediately adjacent the right-hand boundary of the rolling window as it was previously positioned, and the product of the stimulus indicators and respective B-scans in the sequence of B-scans 500 is calculated once again to generate another partial response block (600'-2, etc.) of weighted B-scans. This procedure of sliding the rolling window forward in time and calculating the product to obtain a block of weighted B-scans for each rolling window position is repeated until the rolling window reaches the end of the sequence S of stimulus indicators, thereby generating a plurality of partial response blocks that are each $a \times b_{lag} \times d$ pixels in size, as illustrated in FIG. 21.

In step S30-5 of FIG. 20, the response generator module 125-5 generates an indication of the response of the retina 10 to the light stimulus by combining the calculated correlations. In the present example embodiment, the response generator module 125-5 combines the calculated correlations by performing a matrix addition of the plurality of partial response data blocks 600'-1, 600'-2 ... etc. generated in step S20-5, which are each $a \times b_{lag} \times d$ pixels in size, to generate a response block (also referred to herein as a "response volume") 700', which is a three-dimensional array of combined correlation values that is likewise $a \times b_{lag} \times d$ array elements in size. The combined correlation values in the response block 700' may each be divided by s, to obtain a normalised response.

The three-dimensional array 700' of combined correlation values may further be processed by the response generator module 125-5, and the results of those further processing operations may be used by the image data generator module 130 to generate image data defining an image which indicates the response of the retina 10 to the light stimulus for display to a user of the apparatus 100-5, so that an assessment of how well the retina responds to stimulation can be made. These optional further processing operations will now be described with reference to the flow diagram in FIG. 22.

The response volume 700' may be converted into a two-dimensional response image for easier visualisation by taking the average in the depth (d) direction, i.e. one value per A-scan per lag time point. Thus, in (optional) step S40-5 of FIG. 22 the response generator module 125-5 converts the three-dimensional array 700' of combined correlation values, which is $a \times b_{lag} \times d$ pixels in size, into a two-dimensional array 800' of correlation values, which is $a \times b_{lag}$ pixels in size (as illustrated in FIG. 23(a)), by replacing each one-dimensional array of combined correlation values in the three-dimensional array 700', which one-dimensional array has been calculated using A-scans that are identically located in respective B-scans of the sequence 500 of B-scans, with a single value that is an average of the combined correlation values in the one-dimensional array. The two-dimensional array 800' of combined correlation values indicates the response of the retina 10 to the light stimulus as a function of location along the scanned region R of the retina 10 (i.e. as a function of position along the line defining the scan pattern) and time.

The image data generator module 130 may use the two-dimensional array 800' of combined correlation values to generate image data defining an image which indicates the response of the retina 10 to the light stimulus as a function of location in the scanned region R of the retina 10 and time, where the values of a and $b_{lag}$ determine the extent of the spatial and temporal variations of the response. However, it may be preferable to pre-process the two-dimensional array 800' of combined correlation values generated in step S40-5 prior to image data generation (or prior to the alternative further processing operation described below), in order to accentuate the time-dependent variability of the signal, i.e. the variation of the retinal response to light stimulation over time. Such pre-processing may be desirable in cases where the response variability in the A-scan direction is greater than in the time lag direction.

Figure 23A:
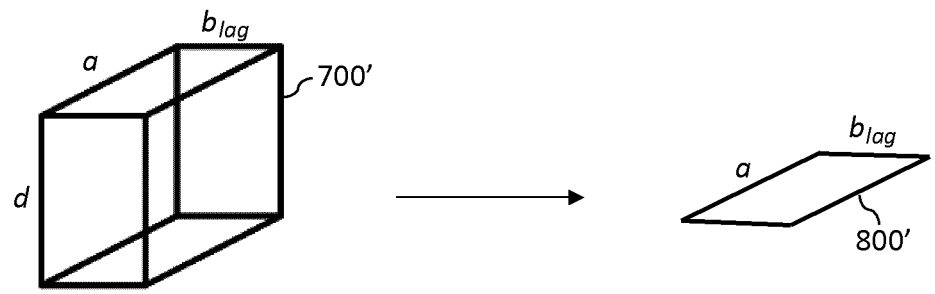
FIG. 23(*a*) is a schematic illustration of a conversion of a three-dimensional array 700' of combined correlation values into a two-dimensional array 800' of combined correlation values by the response generator module 125-5 of the fifth example embodiment herein.
Figure 23B:
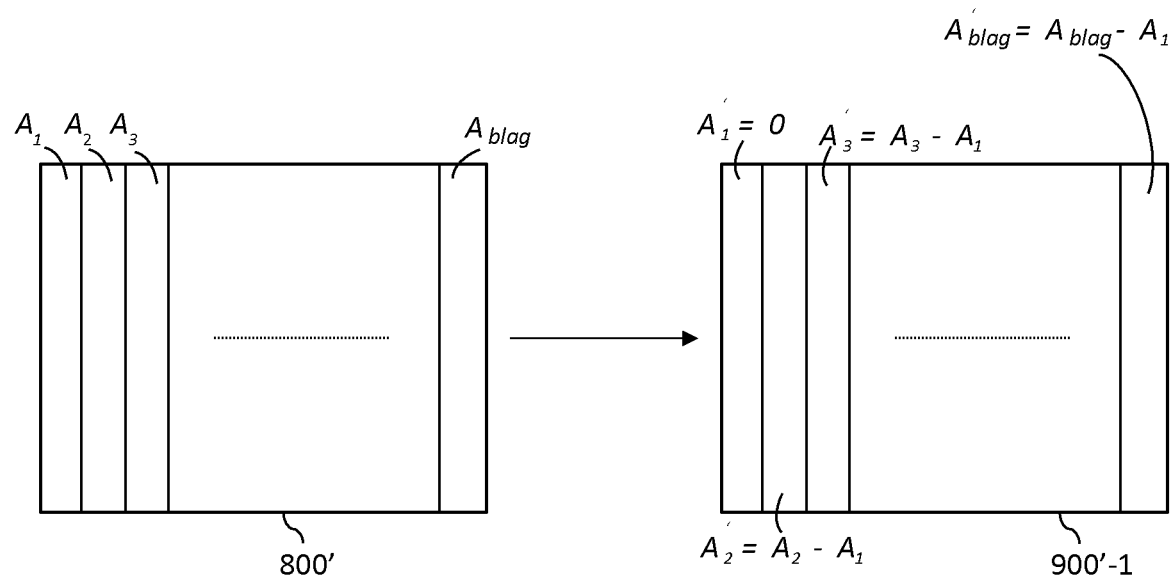
Figure 23C:
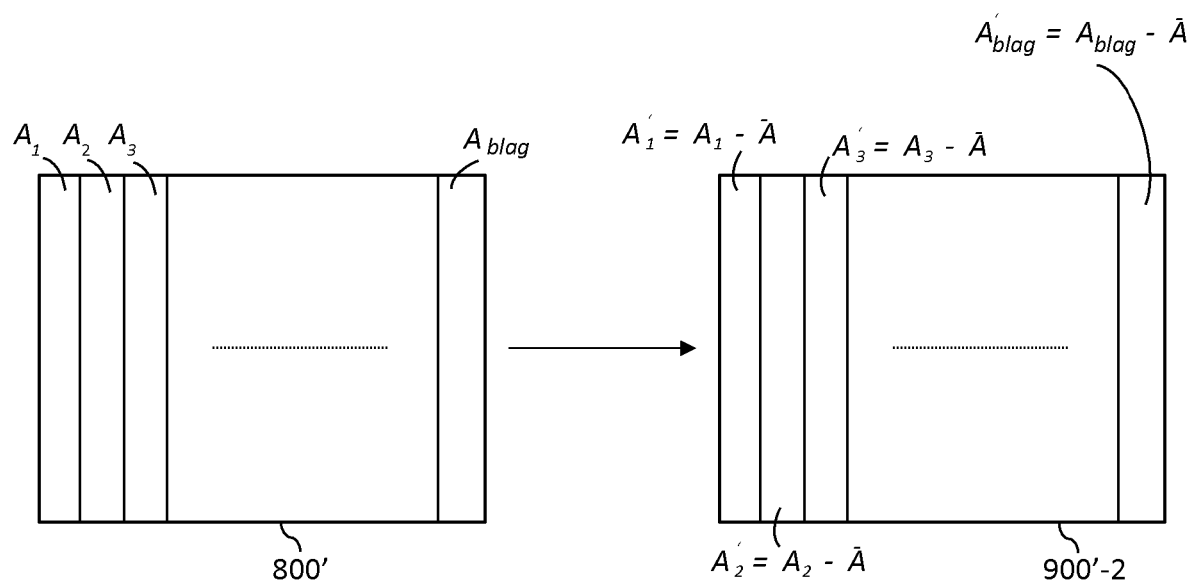

The response generator module 125-5 may pre-process the two-dimensional array 800' of combined correlation values, which comprises a sequence of $b_{lag}$ one-dimensional arrays ($A_1, A_2, \ldots A_{b_{lag}}$), each indicating the response of the retina 10 to the light stimulus as a function of location in the scanned region R of the retina 10, by generating a normalised two-dimensional array of combined correlation values. The response generator module 125-5 may, as illustrated in FIG. 23(b), generate a normalised two-dimensional array, 900'-1, of correlation values by subtracting the first one-dimensional array, $A_1$, in the sequence of one-dimensional arrays from each remaining one-dimensional array ($A_2$, $A_3, \ldots, A_{b_{lag}}$) in the sequence of one-dimensional arrays. Alternatively, the response generator module 125-5 may generate a normalised two-dimensional array of correlation values, 900'-2, by calculating an array of averaged combined correlation values, $$\overline{A} = \frac{1}{b_{lag}} \sum_{n=1}^{b_{lag}} A_n,$$

such that each averaged combined correlation value in the array of averaged combined correlation values is an average (mean) of the combined correlation values that are correspondingly located in the sequence of one-dimensional arrays, and subtracting the calculated array of averaged combined correlation values, $\overline{A}$, from each of the one-dimensional arrays $(A_1, A_2, A_3, \ldots, A_{b_{lag}})$ in the sequence of one-dimensional arrays (in other words, performing a vector subtraction of the calculated array of averaged correlation values from each of the one-dimensional arrays), as illustrated in FIG. 23(c). In both of these alternative ways of calculating normalised two-dimensional array of combined correlation values, the resulting normalised two-dimensional array of combined correlation values, 900'-1 or 900'-2, indicates the response of the retina 10 to the light stimulus as a function of location in the scanned region R of the retina 10 and time.

Figure 22:
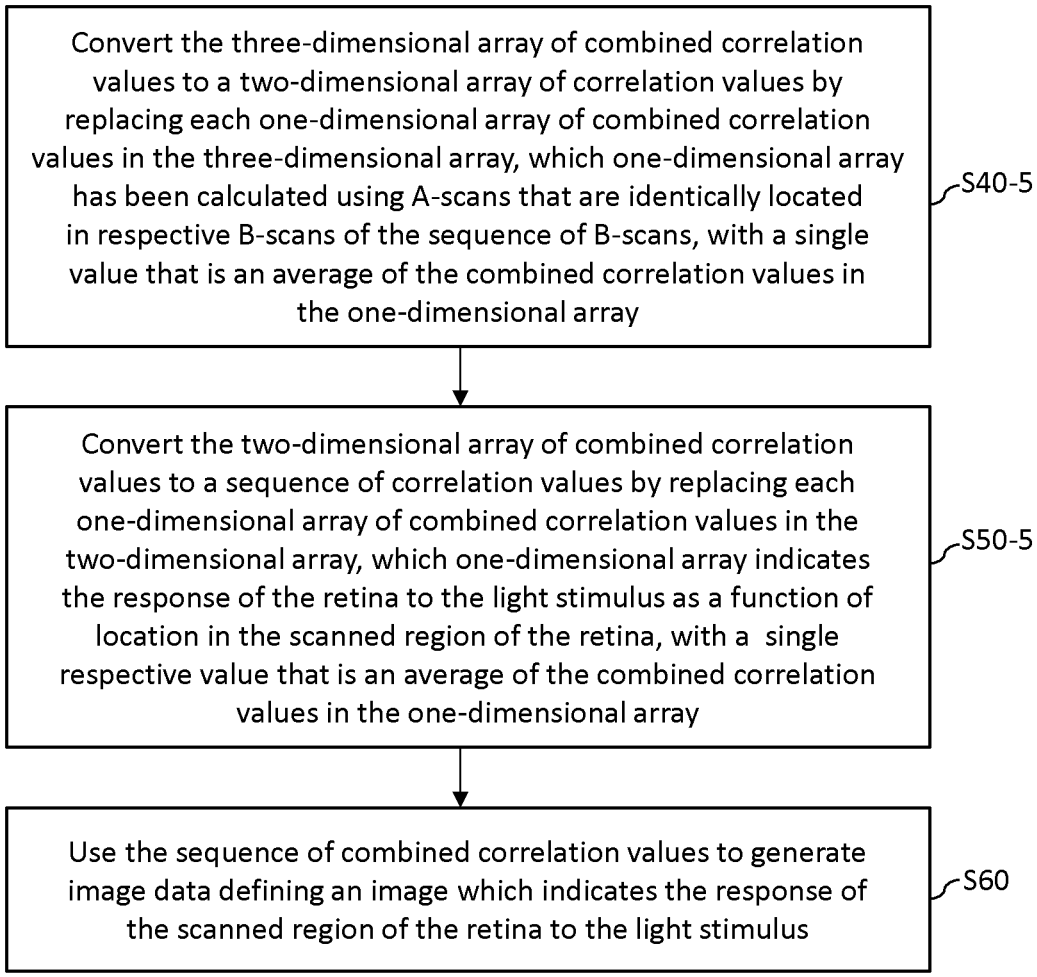
FIG. 22 is a flow diagram illustrating a process by which the three-dimensional array of correlation values generated by a response generator module 125-5 may be processed to generate image data in the fifth example embodiment herein.

To allow the response of the retina 10 to the light stimulus to be illustrated in a form that may be more useful for a healthcare practitioner such as an ophthalmologist, the response generator module 125-5 may, as shown in step S50-5 of FIG. 22, convert the two-dimensional array of combined correlation values (or the normalised two-dimensional array of combined correlation values, as the case may be) to a sequence of combined correlation values by replacing each of the one-dimensional arrays of combined correlation values in the two-dimensional array 800', 900'-1 or 900'-2 (each of the one-dimensional arrays indicating the response of the retina 10 to the light stimulus as a function of location in the scanned region R of the retina 10) with a single respective value that is an average of the combined correlation values in the one-dimensional array, the sequence of combined correlation values indicating a response of the scanned region R of the retina 10 to the light stimulus as a function of time.

In step S60 of FIG. 22, the image data generator module 130 uses the sequence of combined correlation values generated in step S50-5 to generate image data defining an image which indicates the response of the retina 10 to the light stimulus.

The image data may, for example, define an image which indicates the calculated response of the scanned region R of the retina 10 to the light stimulus as a function of time; in other words, the strength of the correlation of the change in OCT intensity with the time elapsed since the corresponding stimulus was applied. An example of such an image has been described above with reference to FIG. 7, and its description will not be repeated here.

Additionally or alternatively, the image data may define an image which indicates one or more properties of a curve which defines the response of the scanned region R of the retina 10 to the light stimulus as a function of time, for example the (solid) response curve shown in FIG. 7. An indicated property of the response curve may (depending on the shape of the curve) be the presence of a change from a predetermined first value to at least a predetermined second (higher or lower) value, the presence of one or more maxima or minima in the response curve, or the absence of a significant change in the calculated correlation strength indicated by the response curve (e.g. as determined by the calculated correlation strength remaining within predefined upper and lower limits), for example. The latter property, i.e. no change in the response curve (other than any noise that may be present) might be expected to be observed in data from diseased eyes, which show little or no response to light stimulation. The indicated property of the response curve may alternatively be data (referred to herein as a "marker") which quantifies one or more of the aforementioned features of the response curve. For example, where there is an extremum (a maximum or a minimum) in the response curve, the image defined by the image data may provide an indication of the time to the extremum since the stimulus was applied and/or an indication of the amplitude of the extremum relative to a predefined reference (e.g. zero correlation strength). Where there is a second extremum in the response curve (which may be the same or a different kind of extremum than the first extremum), the image defined by the image data may additionally or alternatively provide an indication of the time to the second extremum since the stimulus was applied and/or an indication of the amplitude of the second extremum relative to the predefined reference, and/or an indication of the difference in amplitude between the first and second extrema, for example. The indication(s) (marker(s)) may be provided in the form of one or more numerical values, or as a classification of each value into one of a number of predefined numerical ranges, for example. Each indication may be augmented, in the image that is defined by the image data, with a comment or a colour to indicate whether it is within a normal (healthy) range, or within an abnormal range of values that is indicative of a diseased state.

The image data discussed above represents data that has been aggregated over the whole of each B-scan, and thus over the whole of the scanned region R. As a further alternative, respective correlations may be computed for each of a plurality of different sections of the scanned region R of the retina (with each section comprising a different respective set of A-scans), and these correlations may be mapped to an en-face representation of the retina, either as a diagram or as a retinal image such as a fundus image, a scanning laser ophthalmoscope (SLO) image or an en-face OCT image, for example. In other words, the rolling window correlation described above may be calculated separately for each of two or more sections of the sequence of B-scans 500, which are obtained by dividing each B-scan in the sequence of B-scans 500 in the same way, into two or more sets of adjacent A-scans, and concatenating the resulting corresponding sets of A-scans to obtain the respective sections of the sequence of B-scans 500, as illustrated in FIG. 8 (where the B-scans are divided into three equally-sized sections in the A-scan direction, by way of an illustrative example, although there may more generally be more or fewer sections, which need not have the same number of A-scans).

The image data may thus additionally or alternatively define an image which indicates a spatial variation, in the scanned region R of the retina 10, of the one or more properties of the response curve mentioned above (for example), the spatial variation being overlaid on an en-face representation of at least a portion the retina which includes the scanned region R. The correlations calculated for the different sections of the of the scanned region R may be coloured in accordance with any appropriate colour scheme to indicate at least one the following, for example: (i) the value of one of the markers in each of the sections; (ii) which of a predefined set of intervals the marker in each of the sections belongs to, based on a reference database, e.g. green for a part of the scanned region of the retina that has provided a signal which corresponds to a marker "amplitude of the difference between the first and second peak" whose value is within the 95% confidence interval of a population of healthy eyes; (iii) the percentage of the correlation values on the response curve that adheres to the confidence interval of a reference set of either healthy eyes or eyes with a specific disease; or (iv) aggregate values from the response curve, such as maximum, minimum, mean or median over time, where a darker hue or more red colour is higher than a lighter hue or more blue/green colour, for example.

As described above, FIG. 9 illustrates respective correlation strengths calculated using the correlation calculation technique of the first example embodiment for each of four different sections, $R_1$, $R_2$, $R_3$, and $R_4$, of the scanned region R of the retina 10 (using four corresponding sections of the sequence of B-scans 500), which are overlaid on a representation 1000 of the retina 10. The similar figure may be generated using the correlation calculation technique of the present example embodiment. Where the scan has taken place, different colours and hues may be used to indicate one of options (i) to (iv) listed above, for example. In the example of FIG. 9, the scan pattern on the retina resembles the shape of a figure of 8, although other scan patterns could alternatively be used.

As with the first example embodiment, the image which indicates the overlay of the spatial variation (in the scanned region R) of the one or more properties of the response curve onto an en-face representation may be turned into an animation by showing how the correlation strength varies over time at each scan location in the scanned region R shown in the image. Colours and hue may be used to represent the amplitude of the correlation strength and sign by converting either the absolute strength or the normalised strength values to different hues, e.g. darker hues to illustrate a stronger signal, and different colours, e.g. blue for positive correlation and red for negative correlation, for example.

The image data may define an image which is indicative of retinal responses derived from two separate functional OCT data sets, for example a first set of functional OCT data that has been acquired from an eye, and a second set of functional OCT data that has subsequently been acquired from the same eye, the image allowing corresponding responses of the retina to be compared to one another. The image data generator 130 may generate image data that allows two main forms of results to be displayed, as follows: (i) retinal responses based on the first and second sets of functional OCT data, which may be presented in the same (or same kind of) graph or table in order to enable the healthcare practitioner to see the absolute values 'side by side'—this is applicable to both the correlation strength variations over time (which may, for example, be plotted on a graph) and the derived markers (which may, for example, be presented in columns or rows of a table); and (ii) the difference or a ratio between the retinal responses based on the first and second sets of functional OCT data. Colour and hue may be used to show the magnitude and sign (e.g. red for negative and blue for positive) of the difference, for example. An example of a functional OCT report defined by such image data is illustrated in FIG. 10.

It will be appreciated from the foregoing that the fifth example embodiment provides another example of a computer-implemented method of processing functional OCT image data, which has been acquired by an OCT imaging device 200 scanning a retina of a subject while the retina is being repeatedly stimulated by a light stimulus, to generate image data defining an image that provides an indication of a response of the retina to the light stimulus. This method comprises receiving, as the functional OCT image data: OCT image data that has been generated by the OCT imaging device 200 repeatedly scanning a scanned region of the retina over a time period T; and stimulus data defining a sequence S of stimulus indicators ($s_1$, $s_2$, $s_3$) each being indicative of a stimulation of the retina by the light stimulus in a respective time interval of a sequence of time intervals that spans the time period T. The method also makes use of an alternative way of calculating a correlation between a sequence of B-scans 500 that is based on the OCT image data and stimulus indicators in the sequence S of stimulus indicators, and uses the calculated correlation to generate an image which indicates at least one of: the response of the scanned region of the retina to the light stimulus as a function of time; one or more properties of a curve defining the response of the scanned region of the retina to the light stimulus as a function of time; and a spatial variation, in the scanned region of the retina, of one or more properties of the curve defining the response of the scanned region of the retina to the light stimulus as a function of time, the spatial variation being overlaid on an en-face representation of at least a portion the retina which includes the scanned region.

Embodiment 6

In the fifth example embodiment, the correlation calculator module 120-5 is configured to calculate the rolling window correlation between the sequence of B-scans 500 and the sequence S of stimulus indicators received from the OCT imaging device 200, and the response generator module 125-5 is configured to subsequently process the resulting three-dimensional array 700' of combined correlation values (in step S50-5 of FIG. 22) so as to generate a two-dimensional array 800' of combined correlation values, by taking the average of the combined correlation values in the depth (d) direction. However, the averaging operation may, as in the present example embodiment, alternatively be performed on the B-scans prior to their correlation with the sequence S of stimulus indicators, thereby simplifying and speeding up the correlation calculation.

Figure 24:
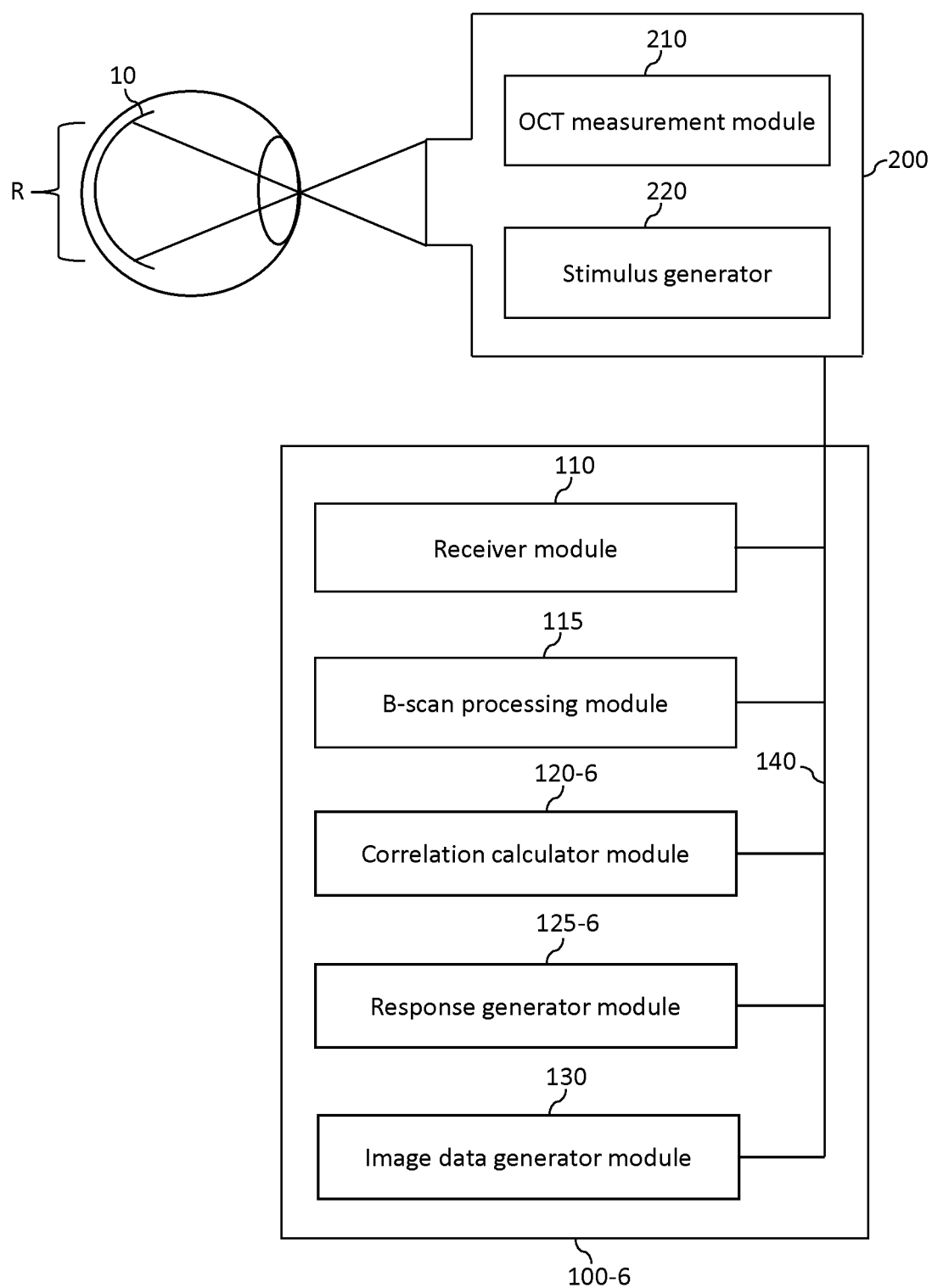
FIG. 24 is a schematic illustration of an apparatus for processing functional OCT image data according to a sixth example embodiment herein.

FIG. 24 is a schematic illustration of an apparatus 100-6 according to the sixth example embodiment, which comprises, in addition to the receiver module 110 and the image data generator module 130 that are the same as those in apparatus 100-5, a B-scan processing module 115 which is the same as that in the second example embodiment, a response generator module 125-6, and a correlation calculator module 120-6. The apparatus 100-6 of the present example embodiment thus differs from the apparatus 100-5 of the fifth example embodiment only by comprising the B-scan processing module 115, the response generator module 125-6, and the correlation calculator module 120-6, whose functionality is explained in detail below. The following description of the sixth example embodiment will therefore focus on these differences, with all other details of the fifth example embodiment, which are applicable to the sixth example embodiment, not being repeated here for sake of conciseness. It should be noted that the variations and modifications which may be made to the fifth example embodiment, as described above, are also applicable to the sixth example embodiment. It should also be noted that one or more of the illustrated components of the apparatus 100-6 may be implemented in the form of a programmable signal processing hardware as described above with reference to FIG. 2, or alternatively in the form of non-programmable hardware, such as an application-specific integrated circuit (ASIC).

Figure 25:
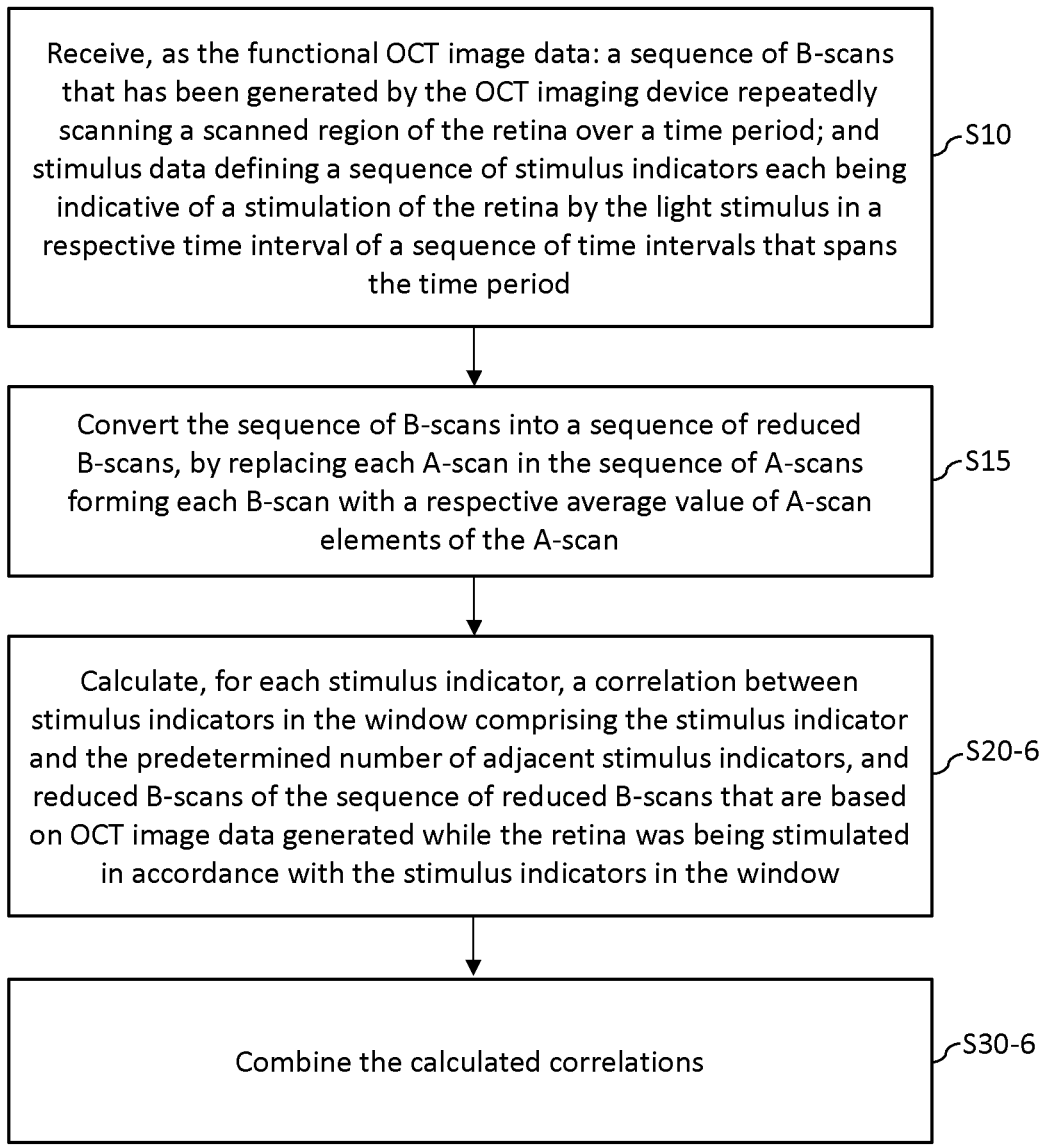
FIG. 25 is a flow diagram illustrating a method of processing functional OCT image data, which has been acquired by an OCT imaging device scanning the subject's retina while the retina is being repeatedly stimulated by the light stimulus, to generate an indication of a response of the retina to the light stimulus in the sixth example embodiment herein.

FIG. 25 is a flow diagram illustrating a method by which the apparatus 100-6 of the sixth example embodiment processes functional OCT data to generate an indication of a response of the retina 10 to the light stimulus.

In step S10 of FIG. 25 (which is same as step S10 in FIG. 20), the receiver module 110 receives from the OCT imaging device 200, as the functional OCT image data: (i) OCT image data (specifically, in the form of a sequence of B-scans 500) that has been generated by the OCT imaging device 200 repeatedly scanning the scanned region R of the retina 10 over a time period T; and (ii) stimulus data defining the sequence of s stimulus indicators, each indicative of a stimulation of the retina by the light stimulus in a respective time interval, T/s, of a sequence of time intervals that spans the time period T.

In step S15 of FIG. 25, the B-scan processing module 115 converts the sequence of B-scans 500 received by the receiver module 110 in step S10 into a sequence of reduced B-scans 550, by replacing each A-scan in the sequence of A-scans forming each B-scan 400 with a respective average value of A-scan elements of the A-scan, as illustrated in FIG. 13.

In step S20-6 of FIG. 25, the correlation calculator module 120-6 calculates the rolling window correlation between reduced B-scans in the sequence of reduced B-scans 550 and stimulus indicators $s_1$, $s_2$, $s_3$ . . . in the sequence S of stimulus indicators by calculating, for each of the stimulus indicators, a correlation between stimulus indicators in the window comprising the stimulus indicator and the predetermined number of adjacent stimulus indicators, and reduced B-scans of the sequence of reduced B-scans 550 that are based on OCT image data generated while the retina 10 was being stimulated in accordance with the stimulus indicators in the window. By way of an example, the correlation calculator module 120-6 of the present example embodiment calculates, for each of the stimulus indicators, a correlation between stimulus indicators in a windowed portion of the sequence S consisting of a stimulus indicator located at a predetermined sequence position in the windowed portion (e.g. the first sequence indicator in the windowed portion), and a predetermined number of adjacent (e.g. subsequent) stimulus indicators, and corresponding reduced B-scans of the sequence of reduced B-scans that are based on a portion of the OCT image data generated while the retina 10 was being stimulated in accordance with the stimulus indicators in the window.

In step S30-6 of FIG. 25, the response generator module 125-6 combines the calculated correlations to generate, as the indication of the response of the retina 10 to the light stimulus, a two-dimensional array of combined correlation values (as shown at 800' in FIG. 23(a)) indicating the response of the retina 10 to the light stimulus as a function of location in the scanned region R of the retina 10 and time.

The two-dimensional array 800' of combined correlation values may be processed by the image data generator module 130 to generate image data in the same way as in the fifth example embodiment, and/or the response generator module 125-6 may pre-process the two-dimensional array 800' of combined correlation values and/or convert the two-dimensional array of combined correlation values (or the normalised two-dimensional array of combined correlation values, as the case may be) to a sequence of combined correlation values in the same way as the response generator module 125-5 of the fifth example embodiment. The sequence of combined correlation values may further be processed by the image data generator module 130 to generate image data in the same way as in step S60 of the fifth example embodiment.

Embodiment 7

The processing of functional OCT data that is performed by the apparatus 100-5 of the fifth example embodiment allows an indication of the functional response of a scanned region R of the retina 10 to be obtained, based on a correlation which is computed for the whole retinal depth covered by the scan. However, it may be valuable for determining disease diagnosis to be able to generate an indication of the individual functional responses of one or more retinal layers corresponding to different cell types (e.g. photoreceptors, retinal pigment epithelium, retinal nerve fiber layer, etc.). Such enhanced functionality is provided by the apparatus 100-7 of the seventh example embodiment, which will now be described with reference to FIGS. 26 and 27.

Figure 26:
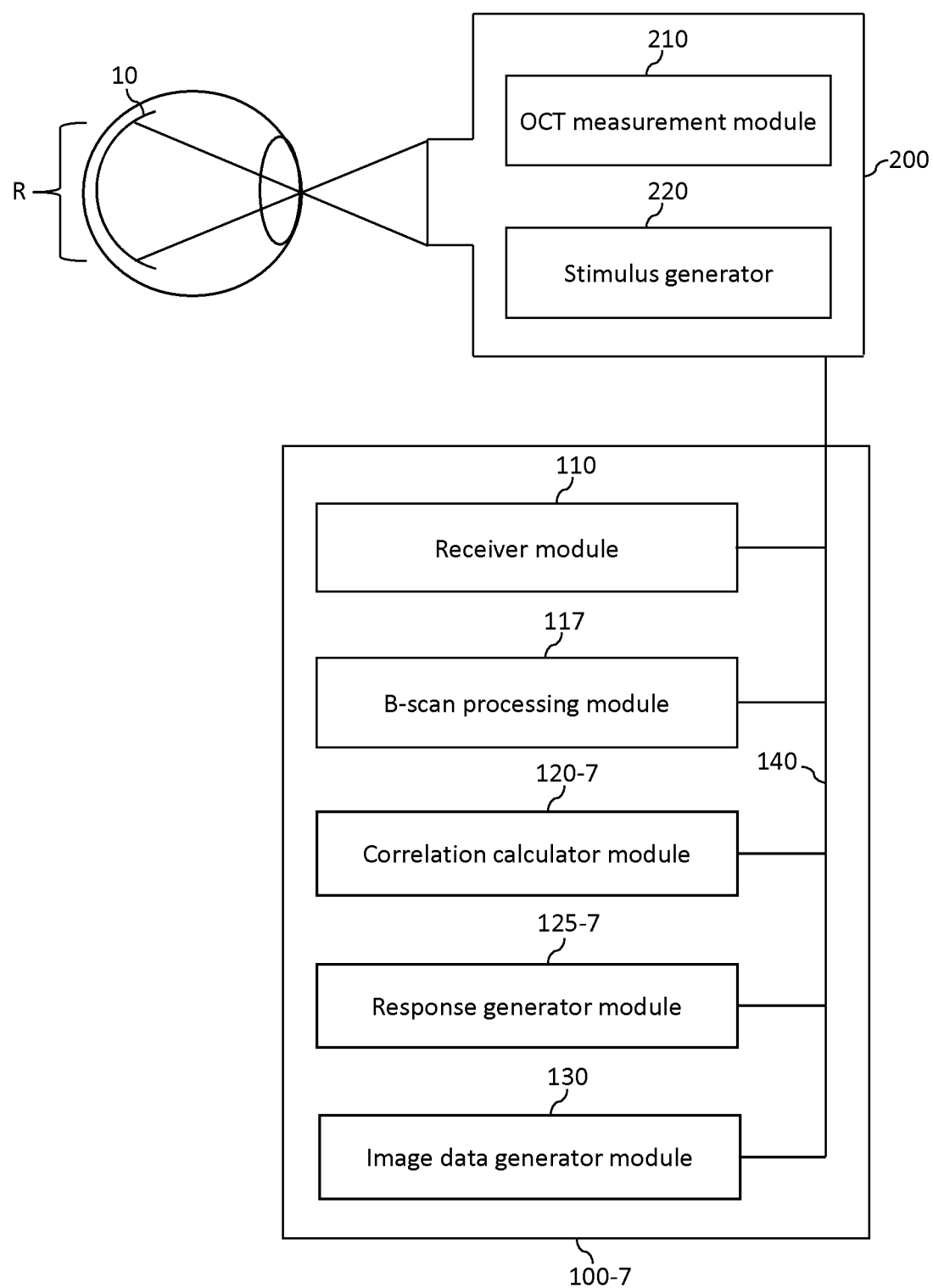
FIG. 26 is a schematic illustration of an apparatus for processing functional OCT image data according to a seventh example embodiment herein.

FIG. 26 is a schematic illustration of an apparatus 100-7 for processing functional OCT image data to generate an indication of the individual responses of one or more layers of the retina 10 to the light stimulus, according to the seventh example embodiment. The apparatus 100-7 comprises the same receiver module 110 as the first, second, fifth and sixth example embodiments, a B-scan processing module 117 which is the same as that of the third example embodiment, a correlation calculator module 120-7, a response generator module 125-7, and an image generator module 130 which is the same as that of the first, second, fifth and sixth example embodiments. It should also be noted that one or more of the illustrated components of the apparatus 100-7 may be implemented in the form of a programmable signal processing hardware as described above with reference to FIG. 2, or alternatively in the form of non-programmable hardware, such as an application-specific integrated circuit (ASIC). Processing operations performed by the apparatus 100-7 will now be described with reference to FIG. 27.

Figure 27:
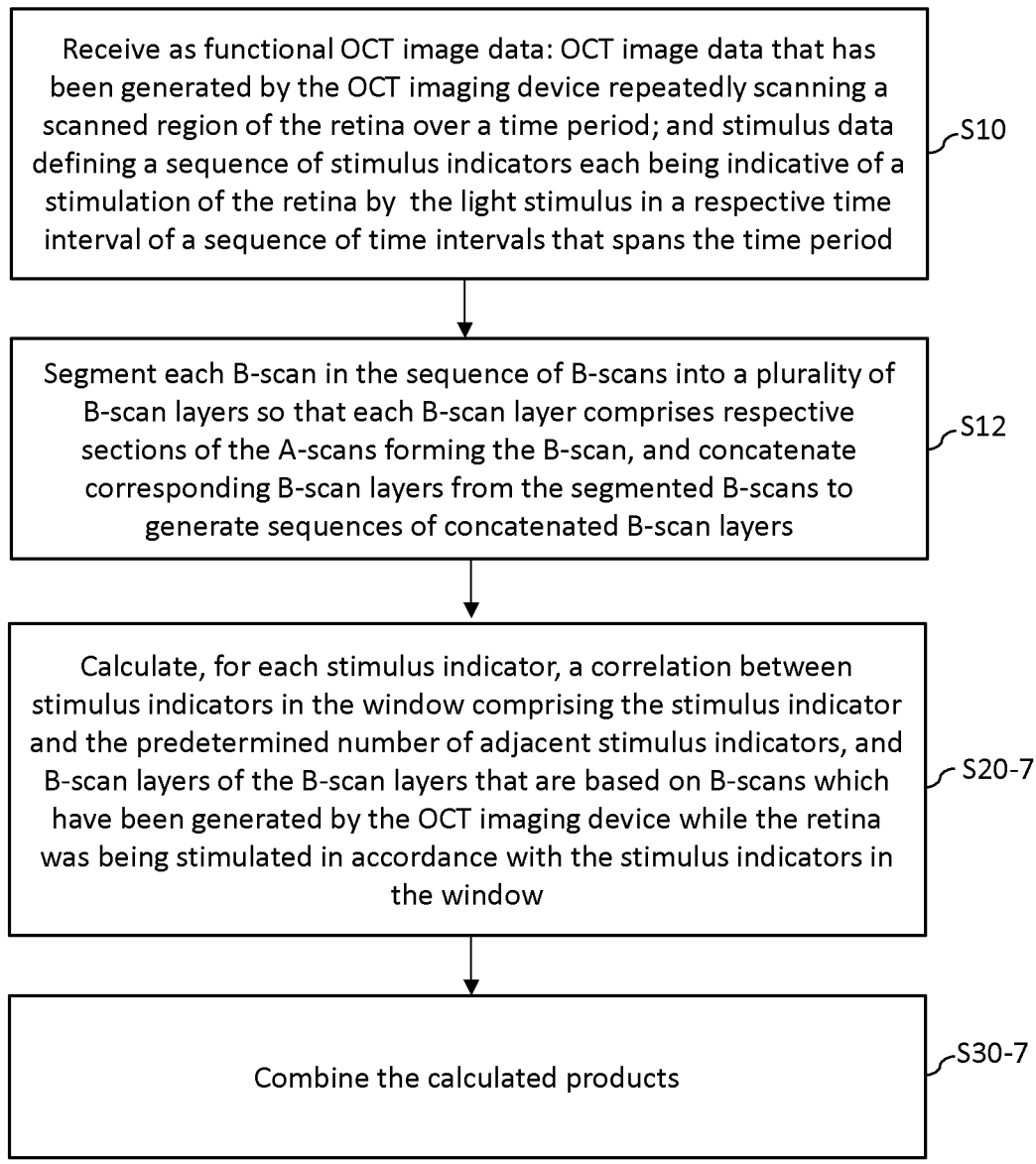
FIG. 27 is a flow diagram illustrating a method of processing functional OCT image data, which has been acquired by an OCT imaging device scanning the subject's retina while the retina is being repeatedly stimulated by the light stimulus, to generate an indication of a response of a layer of the retina to the light stimulus in the seventh example embodiment herein.

FIG. 27 is a flow diagram illustrating a method by which the apparatus 100-7 of the seventh example embodiment processes functional OCT data to generate an indication of the response of one or more layers of the retina 10 to the light stimulus.

In step S10 of FIG. 27, the receiver module 110 receives the functional OCT image data from the OCT imaging device 200. Step S10 in FIG. 27 is the same as step S10 in FIGS. 3, 12, 15, 18, 20 and 25, and will therefore not be described in further detail here.

In step S12 of FIG. 27, the B-scan processing module 117 identically segments each B-scan 400 in the sequence of B-scans 500 into a plurality of B-scan layers, so that each B-scan layer comprises respective sections of the A-scans forming the B-scan 400. Step S12 in FIG. 27 is the same as step S12 in FIG. 15, and its description will therefore not be repeated here. The B-scan processing module 117 further concatenates corresponding B-scan layers from the segmented B-scans to generate sequences of concatenated B-scan layers. Each of the sequences of concatenated B-scan layers thus forms a three-dimensional array of A-scan elements, which corresponds to a respective later of the retina 10.

In step S20-7 of FIG. 27, the correlation calculator module 120-7 calculates, for each of at least one sequence of concatenated B-scan layers of the sequences of concatenated B-scan layers generated in step S12 of FIG. 27, a respective rolling window correlation between the sequence of concatenated B-scan layers and the sequence S of stimulus indicators by calculating, for each stimulus indicator ($s_1$, $s_2$, $s_3$) in the sequence of stimulus indicators, a correlation between stimulus indicators in the window comprising the stimulus indicator and the predetermined number of adjacent stimulus indicators, and B-scan layers of the B-scan layers that are based on B-scans which have been generated by the OCT imaging device 100 while the retina 10 was being stimulated in accordance with the stimulus indicators in the window. In the present example embodiment, the correlation calculator module 120-7 thus calculates, for each of the stimulus indicators, a correlation between stimulus indicators in a windowed portion of the sequence S consisting of a stimulus indicator located at a predetermined sequence position in the windowed portion (e.g. the first sequence indicator in the windowed portion), and a predetermined number of adjacent (e.g. subsequent) stimulus indicators, and corresponding B-scan layers of the sequence of B-scan layers that are based on a portion of the OCT image data generated while the retina 10 was being stimulated in accordance with the stimulus indicators in the window.

In step S30-7 of FIG. 27, for each of the at least one sequence of concatenated B-scan layers, the response generator module 125-7 combines the correlations calculated in step S20-7 to generate a respective three-dimensional array of values ("response volume") that provides an indication of a response of the respective layer of the retina 10 to the light stimulus.

Each resulting three-dimensional array of combined correlation values may further be processed by the response generator module 125-7, and the results of those further processing operations may be used by the image data generator module 130 to generate image data defining an image which indicates the response of the corresponding layer of the retina 10 to the light stimulus for display to a user of the apparatus 100-7, using the further processing operations that have been explained in the above description of the first embodiment, with reference to FIG. 5.

More particularly, the response volume corresponding to each retinal layer may be reduced to a two-dimensional response image for easier visualisation by taking the average in the depth (d) direction, i.e. one value per A-scan per lag time point. Thus, the response generator module 125-7 may convert each three-dimensional array of combined correlation values, which is $a/3 \times b_{lag} \times d$ pixels in size in the present example embodiment, into a respective two-dimensional array of combined correlation values, which is $a/3 \times b_{lag}$ pixels in size, by replacing each one-dimensional array of combined correlation values in the three-dimensional array, which one-dimensional array has been calculated using sections of A-scans that are identically located in respective B-scans of the sequence of B-scans, with a single value that is an average of the combined correlation values in the one-dimensional array. Thus, each array element of the one-dimensional array is calculated on the basis of a corresponding element of an A-scan. The two-dimensional array of combined correlation values indicates the response of the corresponding layer of the retina 10 to the light stimulus as a function of location along the scanned region R of the retina 10 (i.e. as a function of position along the line defining the scan pattern) and time.

The image data generator module 130 may use at least one of the two-dimensional arrays of combined correlation values to generate image data defining an image which indicates the response, to the light stimulus, of a respective layer of the retina 10 corresponding to each of the at least one of the two-dimensional arrays as a function of location in the scanned region R of the retina 10 and time. However, it may be preferable to pre-process at least some of the two-dimensional arrays of combined correlation values prior to image data generation (or prior to the alternative further processing operation described below), in order to accentuate the time-dependent variability of the signal, i.e. the variation of the retinal layer response to light stimulation over time. Such pre-processing may be desirable in cases where the response variability in the A-scan direction is greater than in the time lag direction.

The response generator module 125-7 may pre-process one or more of the two-dimensional arrays of combined correlation values, each comprising a sequence of $b_{lag}$ one-dimensional arrays, each indicating the response of the corresponding layer of the retina 10 to the light stimulus as a function of location in the scanned region R of the retina 10, to generate a normalised two-dimensional array of combined correlation values. The response generator module 125-7 may generate the normalised two-dimensional array of combined correlation values by subtracting the first one-dimensional array in the sequence of one-dimensional arrays from each remaining one-dimensional array in the sequence of one-dimensional arrays. Alternatively, the response generator module 125-7 may generate a normalised two-dimensional array of combined correlation values by calculating an array of averaged combined correlation values, such that each averaged combined correlation value in the array of averaged combined correlation values is an average (mean) of the combined correlation values that are correspondingly located in the sequence of one-dimensional arrays, and subtracting the calculated array of averaged combined correlation values from each of the one-dimensional arrays in the sequence of one-dimensional arrays (in other words, performing a vector subtraction of the calculated array of averaged combined correlation values from each of the one-dimensional arrays). In both of these alternative ways of calculating normalised two-dimensional array of combined correlation values, the resulting normalised two-dimensional array of combined correlation values indicates the response of the corresponding layer of the retina to the light stimulus as a function of location in the scanned region R of the retina 10 and time. The image data generator module 130 may use each normalised two-dimensional array of combined correlation values to generate image data defining an image that indicates the response of the corresponding layer of the retina 10 to the light stimulus as a function of location in the scanned region R of the retina 10 and time.

To allow the response of one or more layers of the retina to the light stimulus to be illustrated in a form that may be more useful for a healthcare practitioner such as an ophthalmologist, the response generator module 125-7 may convert the two-dimensional array of combined correlation values (or the normalised two-dimensional array of combined correlation values, as the case may be) corresponding to each of one or more of the retinal layers to a sequence of correlation values by replacing each of the one-dimensional arrays of combined correlation values in the two-dimensional array (each of the one-dimensional arrays indicating the response of the corresponding layer of the retina 10 to the light stimulus as a function of location in the scanned region R of the retina 10) with a single respective value that is an average of the combined correlation values in the one-dimensional array, each sequence of combined correlation values indicating a response of the respective layer of the retina in the scanned region to the light stimulus as a function of time.

The image data generator module 130 may use one or more of the sequences of combined correlation values to generate image data defining an image that indicates the response of the respective one or more layers of the retina 10 in the scanned region R of the retina 10 to the light stimulus.

Similar to the fifth and sixth example embodiments described above, the image data generator module 130 may use one or more sequences of combined correlation values to generate an image which indicates at least one of: the response of the respective one or more layers of the retina 10 in the scanned region R to the light stimulus as a function of time; one or more properties of a respective one or more curves defining the response of the respective one or more layers of the retina 10 in the scanned region R to the light stimulus as a function of time; and a spatial variation, in the scanned region R of the retina 10, of one or more properties of the respective one or more curves defining the response of the respective one or more layers of the retina 10 in the scanned region R to the light stimulus as a function of time, the spatial variation being overlaid on an en-face representation of at least a portion the retina 10 which includes the scanned region R.

Embodiment 8

In the seventh example embodiment, the correlation calculator module 120-7 is, in one configuration, configured to calculate, for each of at least one sequence of concatenated B-scan layers of the concatenated sequences of B-scan layers, a respective rolling window correlation between the sequence of concatenated B-scan layers and the sequence S of stimulus indicators received from the OCT imaging device 200, and the response generator module 125-7 is configured to subsequently process the resulting three-dimensional array of correlation values so as to generate a two-dimensional array of combined correlation values, by taking an average of the combined correlation values in the depth (d) direction. However, the averaging operation may, as in the present example embodiment, alternatively be performed on the one or more of the sequences of concatenated B-scan layers prior to their correlation with the sequence S of stimulus indicators, thereby simplifying and speeding up the correlation calculation.

Figure 28:
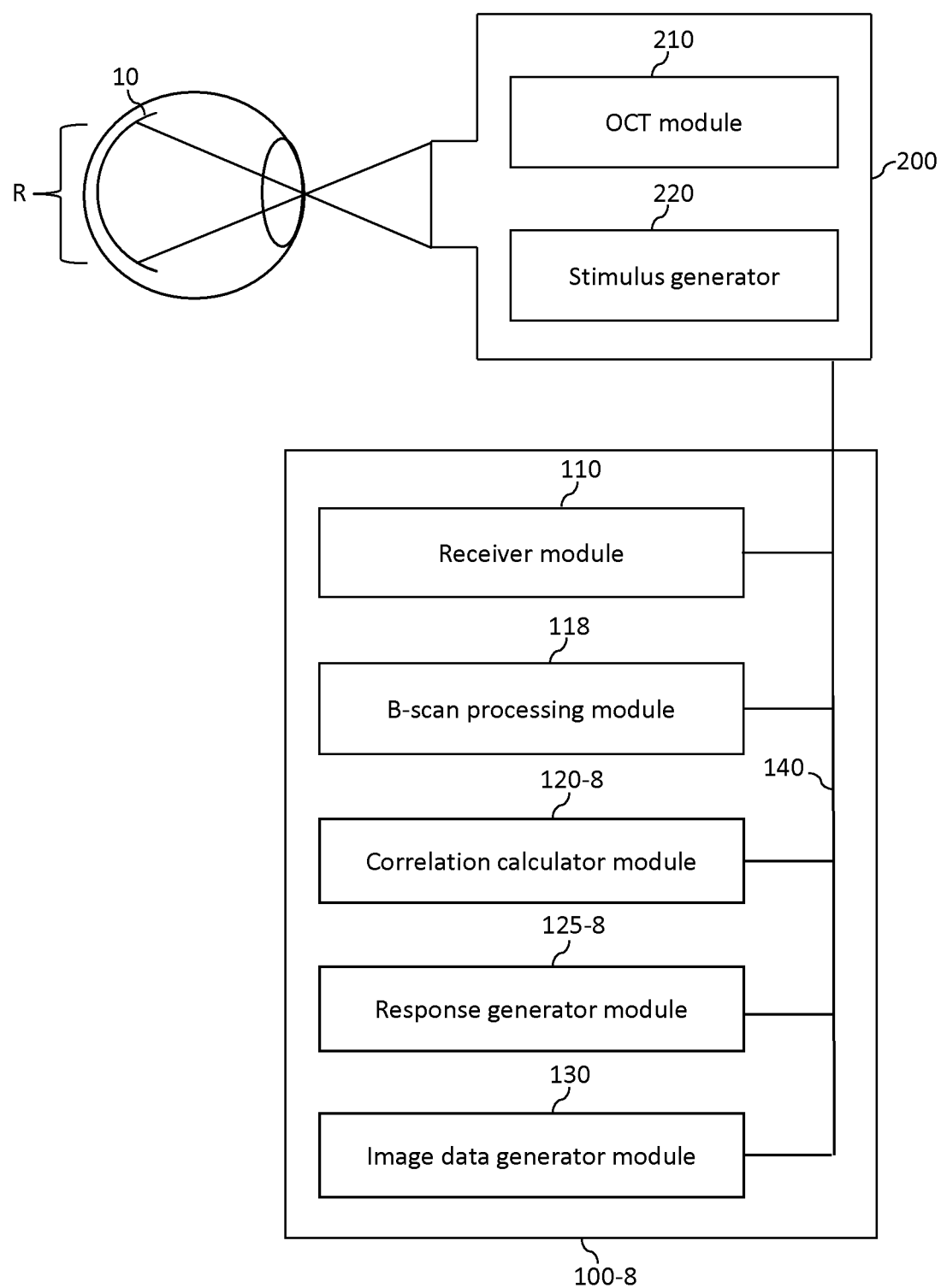
FIG. 28 is a schematic illustration of an apparatus for processing functional OCT image data according to an eighth example embodiment herein.

FIG. 28 is a schematic illustration of an apparatus 100-8 according to the eighth example embodiment, which comprises, in addition to the receiver module 110 and the image data generator module 130 that are the same as those in apparatus of the foregoing example embodiments, and a B-scan processing module 118 which is the same as in the fourth example embodiment, a correlation calculator module 120-8 and a response generator module 125-8 which are described in detail below. It should be noted that one or more of the illustrated components of the apparatus 100-8 may be implemented in the form of a programmable signal processing hardware as described above with reference to FIG. 2, or alternatively in the form of non-programmable hardware, such as an application-specific integrated circuit (ASIC).

Figure 29:
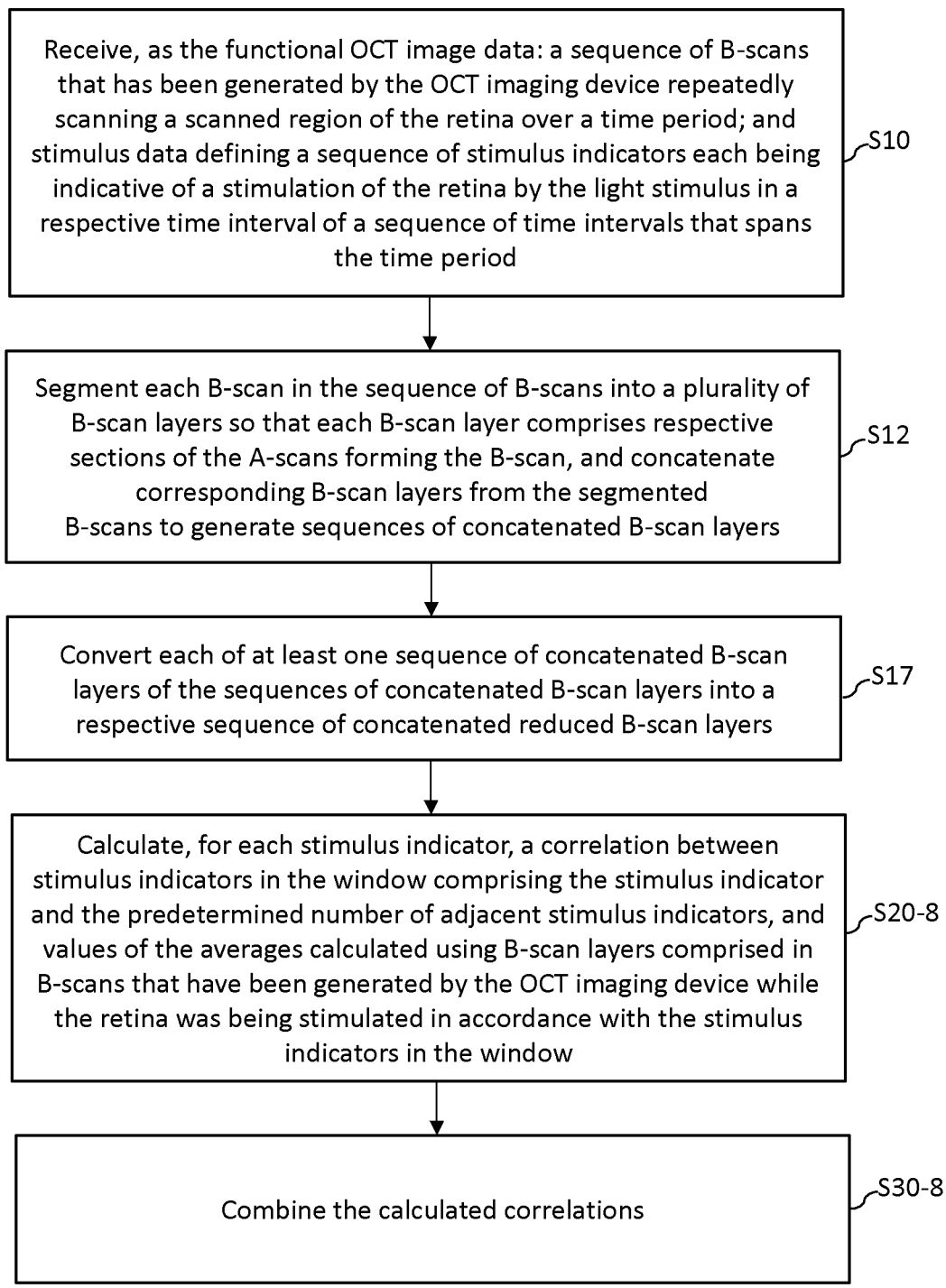
FIG. 29 is a flow diagram illustrating a method of processing functional OCT image data, which has been acquired by an OCT imaging device scanning the subject's retina while the retina is being repeatedly stimulated by the light stimulus, to generate an indication of a response of a layer of the retina to the light stimulus in the eighth example embodiment herein.

FIG. 29 is a flow diagram illustrating a method by which the apparatus 100-8 of the eighth example embodiment processes functional OCT data to generate an indication of a response of the retina 10 to the light stimulus.

In step S10 of FIG. 29, the receiver module 110 receives the functional OCT image data from the OCT imaging device 200. Step S10 in FIG. 29 is the same as step S10 in FIG. 3, for example, and will therefore not be described in further detail here.

In step S12 of FIG. 29, the B-scan processing module 118 identically segments each B-scan 400 in the sequence of B-scans 500 into a plurality of B-scan layers, so that each B-scan layer comprises respective sections of the A-scans forming the B-scan 400. Step S12 in FIG. 29 is the same as step S12 in FIG. 15, for example, and will therefore not be described in further detail here. Each of the sequences of concatenated B-scan layers forms a three-dimensional array of A-scan elements, which corresponds to a respective later of the retina 10.

In step S17 of FIG. 29, the B-scan processing module 118 converts each of at least one of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans. For example, in the illustrative example of FIG. 16, the B-scan processing module 118 converts the three-dimensional array formed by the first sequence of concatenated B-scan layers, 450a, into a two-dimensional array, by replacing the first column of B-scan layer (or segment) 400-1a, comprising A-scan elements a1 and a2, with a single value that is an average of a1 and a2, with the remaining columns of B-scan segment 400-1a, and the other B-scan segments 400-1b, 400-1c, etc. of the first sequence of concatenated B-scan layers 450a being processed in the same way. The B-scan processing module 118 may likewise process the second sequence of concatenated B-scan layers 450b and/or the third sequence of concatenated B-scan layers 450c in addition to, or alternatively to, the first sequence of concatenated B-scan layers 450a. Thus, the B-scan processing module 118 can convert each of one or more of the three-dimensional arrays of OCT measurement values shown in the example of FIG. 16, each of which is $a/3 \times b_{lag} \times d$ pixels in size, into a respective two-dimensional array of values, which is $a/3 \times b_{lag}$ pixels in size.

In step S20-8 of FIG. 29, the correlation calculator module 120-8 calculates, for each of at least one sequence of concatenated reduced B-scan layers of the sequences of concatenated reduced B-scan layers generated in step S17 of FIG. 29, a respective rolling window correlation between reduced B-scan layers in the sequence of concatenated reduced B-scan layers and stimulus indicators ($s_1$, $s_2$, $s_3$) in the sequence S of stimulus indicators, specifically by calculating, for each stimulus indicator in the sequence S of stimulus indicators, a correlation between stimulus indicators in the window comprising the stimulus indicator and the predetermined number of adjacent stimulus indicators, and values of the averages calculated using B-scan layers comprised in B-scans that have been generated by the OCT imaging device 200 while the retina 10 was being stimulated in accordance with the stimulus indicators in the window.

In step S30-8 of FIG. 29, the response generator module 125-8 generates, for each of the at least one sequence of concatenated reduced B-scan layers, an indication of a response of a layer of the retina 10 corresponding to the sequence of concatenated reduced B-scan layers to the light stimulus, by combining the calculated correlations to generate a two-dimensional array of correlation values indicating the response of the layer of the retina 10 to the light stimulus as a function of location in the scanned region R of the retina 10 and time.

Each resulting two-dimensional array of correlation values may further be processed by the response generator module 125-8 in the same way as the two-dimensional array(s) of correlation values is/are processed by the response generator module 125-7 in the seventh example embodiment described above.

Thus, the image data generator module 130 may use at least one of the two-dimensional arrays of correlation values to generate image data defining an image which indicates the response, to the light stimulus, of a respective layer of the retina 10 corresponding to each of the at least one of the two-dimensional arrays as a function of location in the scanned region R of the retina 10 and time. However, it may be preferable to pre-process at least some of the two-dimensional arrays of correlation values prior to image data generation (or prior to the alternative further processing operation described below), in order to accentuate the time-dependent variability of the signal, i.e. the variation of the retinal layer response to light stimulation over time. Such pre-processing may be desirable in cases where the response variability in the A-scan direction is greater than in the time lag direction.

The response generator module 125-8 may pre-process one or more of the two-dimensional arrays of correlation values, each comprising a sequence of $b_{lag}$ one-dimensional arrays, each array indicating the response of the corresponding layer of the retina 10 to the light stimulus as a function of location in the scanned region R of the retina 10, to generate a normalised two-dimensional array of correlation values. The response generator module 125-8 may generate a normalised two-dimensional array of correlation values (indicating the response of the corresponding layer of the retina 10 to the light stimulus as a function of location in the scanned region R of the retina 10 and time) using one of the processes described in the third example embodiment, for example. The image data generator module 130 may use each normalised two-dimensional array of correlation values to generate image data defining an image that indicates the response of the corresponding layer of the retina 10 to the light stimulus as a function of location in the scanned region R of the retina 10 and time.

To allow the response of one or more layers of the retina to the light stimulus to be illustrated in a form that may be more useful for a healthcare practitioner such as an ophthalmologist, the response generator module 125-8 may convert the two-dimensional array of correlation values (or the normalised two-dimensional array of correlation values, as the case may be) corresponding to each of one or more of the retinal layers to a sequence of correlation values by replacing each of the one-dimensional arrays of correlation values in the two-dimensional array (each of the one-dimensional arrays indicating the response of the corresponding layer of the retina 10 to the light stimulus as a function of location in the scanned region R of the retina 10) with a single respective value that is an average of the correlation values in the one-dimensional array, each sequence of correlation values indicating a response of the respective layer of the retina 10 in the scanned region to the light stimulus as a function of time.

The image data generator module 130 may use one or more of the sequences of correlation values to generate image data defining an image that indicates the response of the respective one or more layers of the retina 10 in the scanned region R of the retina 10 to the light stimulus.

Similar to the third example embodiment described above, the image data generator module 130 may use one or more sequences of correlation values to generate an image which indicates at least one of: the response of the respective one or more layers of the retina 10 in the scanned region R to the light stimulus as a function of time; one or more properties of a respective one or more curves defining the response of the respective one or more layers of the retina 10 in the scanned region R to the light stimulus as a function of time; and a spatial variation, in the scanned region R of the retina 10, of one or more properties of the respective one or more curves defining the response of the respective one or more layers of the retina 10 in the scanned region R to the light stimulus as a function of time, the spatial variation being overlaid on an en-face representation of at least a portion the retina 10 which includes the scanned region R.

The example aspects described herein avoid limitations, specifically rooted in computer technology, relating to conventional OCT measurement systems and methods that require large amounts of tomographic data to be acquired during retina light stimulation evaluations, and which require correlation of tomographic data with timing information of applied light stimuli. Such conventional methods and systems are complex and unduly demanding on computer resources. By virtue of the example aspects described herein, on the other hand, retina light stimulation evaluations can be performed in a much less complex manner, and in a manner that may require relatively less computer processing and memory resources than those required by the conventional systems/methods, thereby enabling the evaluations to be performed in a more highly computationally- and resource-efficient manner relative to the conventional systems/methods. Also, by virtue of the foregoing capabilities of the example aspects described herein, which are rooted in computer technology, the example aspects described herein improve computers and computer processing/functionality, and also improve the field(s) of at least image processing, optical coherence tomography (OCT) and data processing, and the processing of functional OCT image data.

Some of the embodiments described above are summarised in the following examples E1 to E41:

E1. An apparatus (100-1; 100-2) configured to process functional OCT image data, which has been acquired by an OCT imaging device (200) scanning a retina of a subject while the retina is being repeatedly stimulated by a light stimulus, to generate an indication (700) of a response of the retina to the light stimulus, the apparatus (100-1; 100-2) comprising:
a receiver module (110) configured to receive, as the functional OCT image data:
OCT image data that has been generated by the OCT imaging device (200) repeatedly scanning a scanned region (R) of the retina over a time period (T); and
stimulus data defining a sequence (S) of stimulus indicators ($s_1$, $s_2$, $s_3$) each being indicative of a stimulation of the retina by the light stimulus in a respective time interval of a sequence of time intervals that spans the time period (T); and
a correlation calculator module (120-1) configured to calculate a rolling window correlation between a sequence of B-scans (500) that is based on the OCT image data and stimulus indicators ($s_1$, $s_2$, $s_3$) in the sequence (S) of stimulus indicators by:
calculating, for each stimulus indicator ($s_1$; $s_2$; $s_3$), a product of the stimulus indicator ($s_1$; $s_2$; $s_3$) and a respective windowed portion of the sequence of B-scans (500) comprising a B-scan (400) which is based on a portion of the OCT image data generated while the retina was being stimulated in accordance with the stimulus indicator; and
combining the calculated products to generate the indication (700) of the response of the retina to the light stimulus.

E2. The apparatus (100-1) according to E1, wherein:
the receiver module (110) is configured to receive a sequence of B-scans (500), which has been generated by the OCT imaging device (200) repeatedly scanning the scanned region (R) of the retina (10) over the time period (T), as the OCT image data; and the correlation calculator module (120-1) is configured to calculate the rolling window correlation between B-scans in the sequence of B-scans (500) and stimulus indicators ($s_1$, $s_2$, $s_3$) in the sequence (S) of stimulus indicators by calculating, for each stimulus indicator ($s_1$; $s_2$; $s_3$), a product of the stimulus indicator ($s_1$; $s_2$; $s_3$) and a respective windowed portion of the sequence of B-scans (500) comprising a B-scan (400) which has been generated by the OCT imaging device (200) while the retina was being stimulated in accordance with the stimulus indicator ($s_1$; $s_2$; $s_3$).

E3. The apparatus (100-1) according to E2, wherein the correlation calculator module (120-1) is configured to:
combine the calculated products to generate a three-dimensional array (700) of correlation values, the three-dimensional array (700) of correlation values comprising one-dimensional arrays of correlation values that have each been calculated using A-scans that are identically located in respective B-scans (400) of the sequence of B-scans (500); and
convert the three-dimensional array (700) of correlation values to a two-dimensional array (800) of correlation values by replacing each of the one-dimensional arrays of correlation values with a respective single value that is an average of the correlation values in the one-dimensional array, the two-dimensional array (800) of correlation values indicating the response of the retina to the light stimulus as a function of location along the scanned region (R) of the retina (10) and time.

E4. The apparatus (100-2) according to E1, wherein:
the receiver module (110) is configured to receive a sequence of B-scans (500), which has been generated by the OCT imaging device (200) repeatedly scanning the scanned region (R) of the retina (10) over the time period (T), as the OCT image data, each of the B-scans (400) being formed by a sequence of A-scans;
the apparatus (100-2) further comprises a B-scan processing module (115) configured to convert the sequence of B-scans (500) into a sequence of reduced B-scans (550), by replacing each A-scan in the sequence of A-scans forming each B-scan with a respective average value of A-scan elements of the A-scan; and
the correlation calculator module (120-2) is configured to:
calculate the rolling window correlation between reduced B-scans in the sequence of reduced B-scans (550) and stimulus indicators ($s_1$, $s_2$, $s_3$) in the sequence (S) of stimulus indicators by calculating, for each stimulus indicator ($s_1$; $s_2$; $s_3$), a product of the stimulus indicator ($s_1$; $s_2$; $s_3$) and a respective windowed portion of the sequence of reduced B-scans (550) comprising a reduced B-scan which is based on a B-scan of the sequence of B-scans (500) which has been generated by the OCT imaging device (200) while the retina (10) was being stimulated in accordance with the stimulus indicator ($s_1$; $s_2$; $s_3$); and
combine the calculated products to generate, as the indication of the response of the retina (10) to the light stimulus, a two-dimensional array (800) of correlation values indicating the response of the retina (10) to the light stimulus as a function of location in the scanned region (R) of the retina (10) and time.

E5. The apparatus (100-1; 100-2) according to E3 or E4, wherein
the two-dimensional array (800) of correlation values comprises an array of one-dimensional arrays of correlation values each indicating the response of the retina (10) to the light stimulus as a function of location in the scanned region (R) of the retina (10), and
the correlation calculator module (120-1; 120-2) is further configured to convert the two-dimensional array (800) of correlation values to a sequence of correlation values by replacing each of the one-dimensional arrays of correlation values in the two-dimensional array (800) with a single respective value that is an average of the correlation values in the one-dimensional array, the sequence of correlation values indicating a response of the scanned region (R) of the retina (10) to the light stimulus as a function of time.

E6. The apparatus (100-1; 100-2) according to E3 or E4, wherein
the two-dimensional array (800) of correlation values comprises a sequence of one-dimensional arrays each indicating the response of the retina (10) to the light stimulus as a function of location in the scanned region (R) of the retina (10), and
the correlation calculator module (120-1; 120-2) is further configured to generate a normalised two-dimensional array (900-1) of correlation values by subtracting the first one-dimensional array ($A_1$) in the sequence of one-dimensional arrays from each remaining one-dimensional array in the sequence of one-dimensional arrays, the normalised two-dimensional array (900-1) of correlation values indicating the response of the retina to the light stimulus as a function of location in the scanned region of the retina and time.

E7. The apparatus (100-1; 100-2) according to E3 or E4, wherein
the two-dimensional array (800) of correlation values comprises an array of one-dimensional arrays each indicating the response of the retina (10) to the light stimulus as a function of location in the scanned region (R) of the retina, and
the correlation calculator module (120-1; 120-2) is further configured to generate a normalised two-dimensional array (900-2) of correlation values by calculating an array of averaged correlation values such that each averaged correlation value in the array of averaged correlation values is an average of the correlation values that are correspondingly located in the one-dimensional arrays, and subtracting the calculated array of averaged correlation values from each of the one-dimensional arrays in the array of one-dimensional arrays, the normalised two-dimensional array (900-2) of correlation values indicating the response of the retina (10) to the light stimulus as a function of location in the scanned region (R) of the retina (10) and time.

E8. The apparatus (100-1; 100-2) according to E6 or E7, wherein
the normalised two-dimensional array (900-1; 900-2) comprises one-dimensional arrays of correlation values, each one-dimensional array of correlation values being indicative of the response of the retina to the light stimulus as a function of location in the scanned region of the retina, and
the correlation calculator module (120-1; 120-2) is further configured to convert the normalised two-dimensional array (900-1; 900-2) of correlation values to a sequence of correlation values by replacing each of the one-dimensional arrays of correlation values in the normalised two-dimensional array (900-1; 900-2) with a respective single value that is an average of the correlation values in the one-dimensional array, the sequence of correlation values indicating a response of the scanned region (R) of the retina (10) to the light stimulus as a function of time.

E9. The apparatus (100-1; 100-2) according to E5 or E8, further comprising:
an image data generator module (130) configured to use the sequence of correlation values to generate image data defining an image which indicates the response of the scanned region of the retina to the light stimulus.

E10. The apparatus (100-1; 100-2) according to E9, wherein the image data generator module (130) is configured to use the sequence of correlation values to generate an image which indicates at least one of:
the response of the scanned region (R) of the retina (10) to the light stimulus as a function of time;
one or more properties of a curve defining the response of the scanned region (R) of the retina (10) to the light stimulus as a function of time; and
a spatial variation, in the scanned region (R) of the retina (10), of one or more properties of the curve defining the response of the scanned region (R) of the retina (10) to the light stimulus as a function of time, the spatial variation being overlaid on an en-face representation (1000) of at least a portion the retina (10) which includes the scanned region (R).

E11. The apparatus (100-3) according to E1, wherein:
the receiver module (110) is configured to receive a sequence of B-scans, which has been generated by the OCT imaging device (200) repeatedly scanning the scanned region of the retina over the time period, as the OCT image data;
the apparatus (100-3) further comprises a B-scan processing module (117) configured to segment each B-scan (400) in the sequence of B-scans (500) into a plurality of B-scan layers (400-1a, 400-1b, 400-1c) so that each B-scan layer comprises respective sections of the A-scans forming the B-scan (400), and concatenate corresponding B-scan layers from the segmented B-scans to generate sequences of concatenated B-scan layers (450a, 450b, 450c);
the correlation calculator module (120-3) is configured to calculate, for each of at least one sequence of concatenated B-scan layers of the sequences of concatenated B-scan layers (450a, 450b, 450c), a respective rolling window correlation between concatenated B-scan layers in the sequence of concatenated B-scan layers and stimulus indicators ($s_1$, $s_2$, $s_3$) in the sequence (S) of stimulus indicators by:
calculating, for each stimulus indicator ($s_1$; $s_2$; $s_3$), a product of the stimulus indicator ($s_1$; $s_2$; $s_3$) and a respective windowed portion of the sequence of concatenated B-scan layers comprising a B-scan layer of the B-scan layers which is based on a B-scan (400) which has been generated by the OCT imaging device (200) while the retina (10) was being stimulated in accordance with the stimulus indicator ($s_1$; $s_2$; $s_3$); and
combining the calculated products to generate an indication of a response of a layer of the retina (10) corresponding to the sequence of concatenated B-scan layers to the light stimulus.

E12. The apparatus (100-3) according to E11, wherein the correlation calculator module (120-3) is configured to:
calculate, as the rolling window correlation for each of the at least one sequence of concatenated B-scan layers, a respective three-dimensional array of correlation values, each three-dimensional array of correlation values comprising one-dimensional arrays of correlation values that have been calculated using sections of A-scans that are identically located in respective B-scans of the sequence of B-scans; and
convert each of at least one of the three-dimensional arrays of correlation values to a respective two-dimensional array of correlation values by replacing each of the one-dimensional arrays of correlation values in the three-dimensional array with a respective single value that is an average of the correlation values in the one-dimensional array, the two-dimensional array of correlation values indicating the response of the corresponding layer of the retina to the light stimulus as a function of location along the scanned region of the retina and time.

E13. The apparatus (100-4) according to E1, wherein:
the receiver module (110) is configured to receive a sequence of B-scans, which has been generated by the OCT imaging device repeatedly scanning the scanned region of the retina over the time period, as the OCT image data;
the apparatus further comprises a B-scan processing module (118) configured to:
segment each B-scan in the sequence of B-scans into a plurality of B-scan layers so that each B-scan layer comprises respective sections of the A-scans forming the B-scan, and concatenating corresponding B-scan layers from the segmented B-scans to generate sequences of concatenated B-scan layers; and
convert each of at least one sequence of concatenated B-scan layers of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans; and
the correlation calculator module (120-4) is configured to calculate, for each of the at least one sequence of concatenated reduced B-scan layers, a respective rolling window correlation between reduced B-scan layers in the sequence of concatenated reduced B-scan layers and stimulus indicators in the sequence of stimulus indicators by:
calculating, for each stimulus indicator, a product of the stimulus indicator and a respective windowed portion of the sequence of concatenated reduced B-scan layers comprising a reduced B-scan layer which is based on a B-scan that has been generated by the OCT imaging device while the retina was being stimulated in accordance with the stimulus indicator; and
combining the calculated products to generate a two-dimensional array of correlation values indicating the response of a layer of the retina corresponding to the sequence of concatenated reduced B-scan layers to the light stimulus as a function of location in the scanned region of the retina and time.

E14. The apparatus (100-3; 100-4) according to E12 or E13, wherein the correlation calculator module (120-3; 120-4) is further configured to convert each of at least one of two-dimensional arrays of correlation values to a respective sequence of correlation values by replacing each one-dimensional array of correlation values in the two-dimensional array, which one-dimensional array indicates the response of the layer of the retina (10) corresponding to the two-dimensional array to the light stimulus as a function of location in the scanned region (R) of the retina (10), with a single value that is an average of the correlation values in the one-dimensional array, the sequence of correlation values indicating a response of the layer of the retina (10) in the scanned region (R) to the light stimulus as a function of time.

E15. The apparatus (100-3; 100-4) according to E12 or E13, wherein
each two-dimensional array of correlation values comprises a sequence of one-dimensional arrays each indicating the response of the respective layer of the retina (10) to the light stimulus as a function of location in the scanned region (R) of the retina (10), and
the correlation calculator module (120-3; 120-4) is further configured to process each two-dimensional array of correlation values to generate a respective normalised two-dimensional array of correlation values by subtracting the first one-dimensional array in the sequence of one-dimensional arrays from each remaining one-dimensional array in the sequence of one-dimensional arrays, the normalised two-dimensional array of correlation values indicating the response of the corresponding layer of the retina (10) to the light stimulus as a function of location in the scanned region (R) of the retina (10) and time.

E16. The apparatus (100-3; 100-4) according to E12 or E13, wherein
each two-dimensional array of correlation values comprises an array of one-dimensional arrays each indicating the response of the respective layer of the retina (10) to the light stimulus as a function of location in the scanned region (R) of the retina (10), and
the correlation calculator module (120-3; 120-4) is further configured to process each two-dimensional array of correlation values to generate a respective normalised two-dimensional array of correlation values by calculating an array of averaged correlation values such that each averaged correlation value in the array of averaged correlation values is an average of the correlation values that are correspondingly located in the one-dimensional arrays, and subtracting the calculated array of averaged correlation values from each of the one-dimensional arrays in the array of one-dimensional arrays, the normalised two-dimensional array of correlation values indicating the response of the corresponding layer of the retina (10) to the light stimulus as a function of location in the scanned region (R) of the retina (10) and time.

E17. The apparatus (100-3; 100-4) according to E15 or E16, wherein the correlation calculator module (120-3; 120-4) is further configured to convert each normalised two-dimensional array of correlation values to a respective sequence of correlation values by replacing each one-dimensional array of correlation values in the normalised two-dimensional array, which one-dimensional array indicates the response of the layer of the retina corresponding to the normalised two-dimensional array of correlation values to the light stimulus as a function of location in the scanned region of the retina, with a single value that is an average of the correlation values in the one-dimensional array, the sequence of correlation values indicating a response of the layer of the retina (10) in the scanned region (R) to the light stimulus as a function of time.

E18. The apparatus (100-3; 100-4) according to E14 or E17, further comprising:

an image data generator module (130) configured to use one or more of the sequences of correlation values to generate image data defining an image that indicates the response of the respective one or more layers of the retina (10) in the scanned region (R) of the retina (10) to the light stimulus.

E19. The apparatus (100-3; 100-4) according to E18, wherein the image data generator module (130) is configured to use the one or more sequences of correlation values to generate an image which indicates at least one of:
the response of the respective one or more layers of the retina (10) in the scanned region (R) to the light stimulus as a function of time;
one or more properties of a respective one or more curves defining the response of the respective one or more layers of the retina (10) in the scanned region (R) to the light stimulus as a function of time; and
a spatial variation, in the scanned region of the retina (10), of one or more properties of the respective one or more curves defining the response of the respective one or more layers of the retina (10) in the scanned region (R) to the light stimulus as a function of time, the spatial variation being overlaid on an en-face representation of at least a portion the retina (10) which includes the scanned region (R).

E20. An apparatus (100-5) configured to process functional OCT image data, which has been acquired by an OCT imaging device (200) scanning a retina (10) of a subject while the retina (10) is being repeatedly stimulated by a light stimulus, to generate an indication of a response of the retina to the light stimulus, the apparatus (100-5) comprising:
a receiver module (110) configured to receive, as the functional OCT image data:
OCT image data that has been generated by the OCT imaging device (200) repeatedly scanning a scanned region (R) of the retina (10) over a time period (T); and
stimulus data defining a sequence (S) of stimulus indicators ($s_1$, $s_2$, $s_3$) each being indicative of a stimulation of the retina (10) by the light stimulus in a respective time interval of a sequence of time intervals that spans the time period (T);
a correlation calculator module (120-5) configured to calculate a rolling window correlation between a sequence of B-scans (500) that is based on the OCT image data and at least some of the stimulus indicators ($s_1$, $s_2$, $s_3$) in the sequence (S) of stimulus indicators by calculating, for each stimulus indicator, a correlation between
stimulus indicators in a window comprising the stimulus indicator and a predetermined number of adjacent stimulus indicators, and
B-scans of the sequence of B-scans (500) that are based on a portion of the OCT image data generated while the retina (10) was being stimulated in accordance with the stimulus indicators in the window; and
a response generator module (125) configured to generate the indication of the response of the retina (10) to the light stimulus by combining the calculated correlations.

E21. The apparatus (100-5) according to E20, wherein:
the receiver module (110) is configured to receive a sequence of B-scans, which has been generated by the OCT imaging device (200) repeatedly scanning the scanned region (R) of the retina (10) over the time period, as the OCT image data;

the correlation calculator module (120-5) is configured to calculate the rolling window correlation between the sequence of B-scans (500) and the sequence (S) of stimulus indicators by calculating, for each stimulus indicator ($s_1$, $s_2$, $s_3$) in the sequence (S) of stimulus indicators, a correlation between
- stimulus indicators in the window comprising the stimulus indicator and the predetermined number of adjacent stimulus indicators, and
- B-scans of the sequence of B-scans (500) that have been generated by the OCT imaging device (200) while the retina (10) was being stimulated in accordance with the stimulus indicators in the window.

E22. The apparatus (100-5) according to E21, wherein the response generator module (125) is configured to combine the calculated correlations to generate a three-dimensional array of combined correlation values, the three-dimensional array of combined correlation values comprising one-dimensional arrays of combined correlation values that have each been calculated using A-scans that are identically located in respective B-scans of the sequence of B-scans (500), the response generator module (125) being configured to generate the indication of the response of the retina (10) to the light stimulus by:
converting the three-dimensional array of combined correlation values to a two-dimensional array of combined correlation values by replacing each of the one-dimensional arrays of combined correlation values with a respective single value that is an average of the combined correlation values in the one-dimensional array, the two-dimensional array of combined correlation values indicating the response of the retina (10) to the light stimulus as a function of location along the scanned region (R) of the retina (10) and time.

E23. The apparatus (100-6) according to E20, wherein:
the receiver module (110) is configured to receive a sequence of B-scans, which has been generated by the OCT imaging device (200) repeatedly scanning the scanned region (R) of the retina (10) over the time period (T), as the OCT image data, each of the B-scans being formed by a sequence of A-scans;
the apparatus (100-6) further comprises a B-scan processing module (115) configured to convert the sequence of B-scans into a sequence of reduced B-scans, by replacing each A-scan in the sequence of A-scans forming each B-scan with a respective average value of A-scan elements of the A-scan;
the correlation calculator module (120-6) is configured to calculate the rolling window correlation between the sequence of reduced B-scans and the sequence of stimulus indicators by calculating, for each stimulus indicator ($s_1$, $s_2$, $s_3$) in the sequence (S) of stimulus indicators, a correlation between
- stimulus indicators in the window comprising the stimulus indicator and the predetermined number of adjacent stimulus indicators, and
- reduced B-scans of the sequence of reduced B-scans that are based on OCT image data generated while the retina (10) was being stimulated in accordance with the stimulus indicators in the window; and the indication of the response of the retina (10) to the light stimulus generated by the response generator module (125-6) comprises a two-dimensional array of combined correlation values indicating the response of the retina (10) to the light stimulus as a function of location in the scanned region (R) of the retina (10) and time.

E24. The apparatus (100-5; 100-6) according to E22 or E23, wherein
the two-dimensional array of combined correlation values comprises an array of one-dimensional arrays of combined correlation values each indicating the response of the retina (10) to the light stimulus as a function of location in the scanned region (R) of the retina (10), and
the response generator module (125-5; 125-6) is configured to generate the indication of the response of the retina (10) to the light stimulus by:
converting the two-dimensional array of combined correlation values to a sequence of combined correlation values by replacing each of the one-dimensional arrays of combined correlation values in the two-dimensional array with a single respective value that is an average of the combined correlation values in the one-dimensional array, the sequence of combined correlation values indicating a response of the scanned region (R) of the retina (10) to the light stimulus as a function of time.

E25. The apparatus (100-5; 100-6) according to E22 or E23, wherein the two-dimensional array of combined correlation values comprises a sequence of one-dimensional arrays each indicating the response of the retina (10) to the light stimulus as a function of location in the scanned region (R) of the retina (10), and wherein the response generator module (125-5; 125-6) is configured to generate the indication of the response of the retina (10) to the light stimulus further by:
generating a normalised two-dimensional array of combined correlation values by subtracting the first one-dimensional array in the sequence of one-dimensional arrays from each remaining one-dimensional array in the sequence of one-dimensional arrays, the normalised two-dimensional array of combined correlation values indicating the response of the retina (10) to the light stimulus as a function of location in the scanned region (R) of the retina (10) and time.

E26. The apparatus (100-5; 100-6) according to E22 or E23, wherein the two-dimensional array of combined correlation values comprises an array of one-dimensional arrays each indicating the response of the retina (10) to the light stimulus as a function of location in the scanned region (R) of the retina (10), and wherein the response generator module (125-5; 125-6) is configured to generate the indication of the response of the retina (10) to the light stimulus by:
generating a normalised two-dimensional array of combined correlation values by calculating an array of averaged combined correlation values such that each averaged combined correlation value in the array of averaged combined correlation values is an average of the combined correlation values that are correspondingly located in the one-dimensional arrays, and subtracting the calculated array of averaged combined correlation values from each of the one-dimensional arrays in the array of one-dimensional arrays, the normalised two-dimensional array of combined correlation values indicating the response of the retina (10) to the light stimulus as a function of location in the scanned region (R) of the retina (10) and time.

E27. The apparatus (100-5; 100-6) according to E25 or E26, wherein
the normalised two-dimensional array comprises one-dimensional arrays of combined correlation values, each one-dimensional array of combined correlation values being indicative of the response of the retina to the light stimulus as a function of location in the scanned region (R) of the retina (10), and the response generator module (125-5; 125-6) is configured to generate the indication of the response of the retina (10) to the light stimulus by:

converting the normalised two-dimensional array of combined correlation values to a sequence of combined correlation values by replacing each of the one-dimensional arrays of combined correlation values in the normalised two-dimensional array with a respective single value that is an average of the combined correlation values in the one-dimensional array, the sequence of combined correlation values indicating a response of the scanned region (R) of the retina (10) to the light stimulus as a function of time.

E28. The apparatus (100-5; 100-6) according to E24 or E27, further comprising:

an image data generator module (130) configured to use the sequence of combined correlation values to generate image data defining an image which indicates the response of the scanned region (R) of the retina (10) to the light stimulus as a function of time.

E29. The apparatus (100-5; 100-6) according to E28, wherein the image data generator module (130) is configured to use the sequence of correlation values to generate an image which indicates at least one of:

the response of the scanned region (R) of the retina (10) to the light stimulus as a function of time;

one or more properties of a curve defining the response of the scanned region (R) of the retina (10) to the light stimulus as a function of time; and a spatial variation, in the scanned region (R) of the retina (10), of one or more properties of the curve defining the response of the scanned region (R) of the retina (10) to the light stimulus as a function of time, the spatial variation being overlaid on an en-face representation (1000) of at least a portion the retina (10) which includes the scanned region (R).

E30. The apparatus (100-7) according to E20, wherein:

the receiver module (110) is configured to receive a sequence of B-scans, which has been generated by the OCT imaging device (200) repeatedly scanning the scanned region (R) of the retina (10) over the time period, as the OCT image data;

the apparatus further comprises a B-scan processing module (117) configured o segment each B-scan in the sequence of B-scans (500) into a plurality of B-scan layers so that each B-scan layer comprises respective sections of the A-scans forming the B-scan, and concatenate corresponding B-scan layers from the segmented B-scans to generate sequences of concatenated B-scan layers;

the correlation calculator module (120-7) is configured to calculate, for each of at least one sequence of concatenated B-scan layers of the sequences of concatenated B-scan layers, a respective rolling window correlation between the sequence of concatenated B-scan layers and the sequence of stimulus indicators by calculating, for each stimulus indicator in the sequence of stimulus indicators, a correlation between stimulus indicators in the window comprising the stimulus indicator and the predetermined number of adjacent stimulus indicators, and B-scan layers of the B-scan layers that are based on B-scans which have been generated by the OCT imaging device (200) while the retina (10) was being stimulated in accordance with the stimulus indicators in the window; and the response generator module (125-7) is configured to generate the indication of the response of the retina (10) to the light stimulus by generating, for each of the at least one sequence of concatenated B-scan layers, an indication of a response of a layer of the retina (10) corresponding to the sequence of concatenated B-scan layers to the light stimulus, by combining the calculated correlations.

E31. The apparatus (100-7) according to E30, wherein the correlation calculator module (120-7) is configured to calculate, as the rolling window correlation for each of the at least one sequence of concatenated B-scan layers, a respective three-dimensional array of combined correlation values, each three-dimensional array of combined correlation values comprising one-dimensional arrays that have been calculated using sections of A-scans that are identically located in respective B-scans of the sequence of B-scans, and the response generator module (125-7) is configured to generate the indication of the response to the light stimulus of a respective layer of the retina (10) corresponding to each of the at least one sequence of concatenated B-scan layers by:

converting the three-dimensional array of combined correlation values to a two-dimensional array of combined correlation values by replacing each of the one-dimensional arrays of combined correlation values in the three-dimensional array with a respective single value that is an average of the combined correlation values in the one-dimensional array, the two-dimensional array of combined correlation values indicating the response of the retina (10) to the light stimulus as a function of location along the scanned region (R) of the retina (10) and time.

E32. The apparatus (100-8) according to E20, wherein:

the receiver module (110) is configured to receive a sequence of B-scans, which has been generated by the OCT imaging device (200) repeatedly scanning the scanned region (R) of the retina (10) over the time period, as the OCT image data;

the apparatus (100-8) further comprises a B-scan processing module (118) configured to:

segment each B-scan in the sequence of B-scans (500) into a plurality of B-scan layers so that each B-scan layer comprises respective sections of the A-scans forming the B-scan, and concatenate corresponding B-scan layers from the segmented B-scans to generate sequences of concatenated B-scan layers; and convert each of at least one sequence of concatenated B-scan layers of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans;

the correlation calculator module (120-8) is configured to calculate, for each of the at least one sequence of concatenated reduced B-scan layers, a respective rolling window correlation between the sequence of concatenated reduced B-scan layers and the sequence of stimulus indicators by calculating, for each stimulus indicator in the sequence of stimulus indicators, a correlation between
stimulus indicators in the window comprising the stimulus indicator and the predetermined number of adjacent stimulus indicators, and
values of the averages calculated using B-scan layers comprised in B-scans that have been generated by the OCT imaging device (200) while the retina (10) was being stimulated in accordance with the stimulus indicators in the window; and
the response generator module (125-8) is configured to generate the indication of the response of the retina (10) to the light stimulus by generating, for each of the at least one sequence of concatenated reduced B-scan layers, an indication of a response of a layer of the retina corresponding to the sequence of concatenated reduced B-scan layers to the light stimulus, by combining the calculated correlations to generate a two-dimensional array of combined correlation values indicating the response of the layer of the retina (10) to the light stimulus as a function of location in the scanned region (R) of the retina (10) and time.

E33. The apparatus (100-7; 100-8) according to E31 or E32, wherein
the response generator module (125-7; 125-8) is configured to generate the indication of the response to the light stimulus of each layer of the retina (10) corresponding to the at least one sequence of concatenated reduced B-scan layers by:
converting the respective two-dimensional array of combined correlation values to a respective sequence of combined correlation values by replacing each one-dimensional array of combined correlation values in the two-dimensional array, which one-dimensional array indicates the response of the layer of the retina (10) to the light stimulus as a function of location in the scanned region (r) of the retina (10), with a single value that is an average of the combined correlation values in the one-dimensional array, the sequence of combined correlation values indicating a response of the layer of the retina (10) in the scanned region (R) to the light stimulus as a function of time.

E34. The apparatus (100-7; 100-8) according to E31 or E32, wherein each two-dimensional array of combined correlation values comprises a sequence of one-dimensional arrays each indicating the response of the respective layer of the retina (10) to the light stimulus as a function of location in the scanned region (R) of the retina (10), and wherein the response generator module (125-7; 125-8) is configured to generate the indication of the response to the light stimulus of each layer of the retina (10) corresponding to the respective one of the at least one sequence of concatenated B-scan layers by:
generating a normalised two-dimensional array of combined correlation values by subtracting the first one-dimensional array in the sequence of one-dimensional arrays from each remaining one-dimensional array in the sequence of one-dimensional arrays, the normalised two-dimensional array of combined correlation values indicating the response of the layer of the retina (10) to the light stimulus as a function of location in the scanned region (R) of the retina (10) and time.

E35. The apparatus (100-7; 100-8) according to E31 or E32, wherein each two-dimensional array of combined correlation values comprises an array of one-dimensional arrays each indicating the response of the respective layer of the retina (10) to the light stimulus as a function of location in the scanned region (R) of the retina (10), and wherein the response generator module (125-7; 125-8) is configured to generate the indication of the response to the light stimulus of each layer of the retina (10) corresponding to the respective one of the at least one sequence of concatenated B-scan layers by:
generating a normalised two-dimensional array of combined correlation values by calculating an array of averaged combined correlation values such that each averaged combined correlation value in the array of averaged combined correlation values is an average of the combined correlation values that are correspondingly located in the one-dimensional arrays, and subtracting the calculated array of averaged combined correlation values from each of the one-dimensional arrays in the array of one-dimensional arrays, the normalised two-dimensional array of combined correlation values indicating the response of the layer of the retina (10) to the light stimulus as a function of location in the scanned region (R) of the retina (10) and time.

E36. The apparatus (100-7; 100-8) according to E34 or E35, wherein the response generator module (125-7; 125-8) is configured to generate the indication of the response to the light stimulus of each layer of the retina (10) corresponding to the at least one sequence of concatenated reduced B-scan layers by:
converting the respective normalised two-dimensional array of combined correlation values to a respective sequence of combined correlation values by replacing each one-dimensional array of combined correlation values in the normalised two-dimensional array, which one-dimensional array indicates the response of the layer of the retina to the light stimulus as a function of location in the scanned region of the retina, with a single value that is an average of the combined correlation values in the one-dimensional array, the sequence of combined correlation values indicating a response of the layer of the retina (10) in the scanned region (R) to the light stimulus as a function of time.

E37. The apparatus (100-7; 100-8) according to E33 or E36, further comprising:
an image data generator module (130) configured to use the sequence of combined correlation values to generate image data defining an image that indicates the response of the layer of the retina (10) in the scanned region (R) of the retina (10) to the light stimulus as a function of time.

E38. The apparatus (100-7; 100-8) according to E37, wherein the image data generator module (130) is configured to use the one or more sequences of correlation values to generate an image which indicates at least one of:
the response of the respective one or more layers of the retina (10) in the scanned region (R) to the light stimulus as a function of time;
one or more properties of a respective one or more curves defining the response of the respective one or more layers of the retina (10) in the scanned region (R) to the light stimulus as a function of time; and
a spatial variation, in the scanned region (R) of the retina (10), of one or more properties of the respective one or more curves defining the response of the respective one or more layers of the retina (10) in the scanned region (R) to the light stimulus as a function of time, the spatial variation being overlaid on an en-face representation of at least a portion the retina (10) which includes the scanned region (R).

E39. The apparatus (100-1 to 100-8) according to any of E1 to E38, wherein the light stimulus comprises a light stimulus providing illumination over a whole visual field of the subject.

E40. The apparatus (100-1 to 100-8) according to any of E1 to E39, wherein the sequence of stimulus indicators indicates a random or pseudo-random stimulation of the retina (10) over time.

E41. The apparatus (100-1 to 100-8) according to any of E1 to E40, wherein each stimulus indicator in the sequence of stimulus indicators is indicative of whether or not the retina (10) was stimulated by the light stimulus, or a change in stimulation of the retina (10) by the light stimulus, in a respective time interval of the sequence of time intervals that spans the time period (T).

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g. program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects herein, as described above.

Included in the programming and/or software of the system are software modules for implementing the procedures described herein. In some example embodiments herein, a module includes software, although in other example embodiments herein, a module includes hardware, or a combination of hardware and software.

While various example embodiments have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that the procedures recited in the claims need not be performed in the order presented.

While this specification contains many specific embodiment details, these should not be construed as limiting, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatus and computer programs described herein may be embodied in other specific forms without departing from the characteristics thereof. The foregoing embodiments are illustrative rather than limiting of the described systems and methods. Scope of the apparatus and computer programs described herein is thus indicated by the appended claims, rather than the foregoing description, and changes that come within the meaning and range of equivalency of the claims are embraced therein.

The invention claimed is:

1. A non-transitory computer-readable storage medium storing computer program instructions which, when executed by a computer processor, cause the computer processor to perform a method of processing functional OCT image data, which has been acquired by an OCT imaging device scanning a retina of a subject while the retina is being repeatedly stimulated by a light stimulus, to generate an indication of a response of the retina to the light stimulus, the method comprising:
   receiving, as the functional OCT image data:
      OCT image data that has been generated by the OCT imaging device repeatedly scanning a scanned region of the retina over a time period, and
      stimulus data defining a sequence of stimulus indicators each being indicative of a stimulation of the retina by the light stimulus in a respective time interval of a sequence of time intervals that spans the time period; and
   calculating a rolling window correlation between a sequence of B-scans that is based on the OCT image data and stimulus indicators in the sequence of stimulus indicators by:
      calculating, for each stimulus indicator, a product of the stimulus indicator and a respective windowed portion of the sequence of B-scans comprising a B-scan which is based on a portion of the OCT image data generated while the retina was being stimulated in accordance with the stimulus indicator, and
      combining the calculated products to generate the indication of the response of the retina to the light stimulus.

2. The non-transitory computer-readable storage medium according to claim 1, wherein:
   a sequence of B-scans which has been generated by the OCT imaging device repeatedly scanning the scanned region of the retina over the time period is received as the OCT image data; and
   the rolling window correlation is calculated between B-scans in the sequence of B-scans and stimulus indicators in the sequence of stimulus indicators by calculating, for each stimulus indicator, a product of the stimulus indicator and a respective windowed portion of the sequence of B-scans comprising a B-scan which has been generated by the OCT imaging device while the retina was being stimulated in accordance with the stimulus indicator.

3. The non-transitory computer-readable storage medium according to claim 2, wherein the calculated products are combined to generate a three-dimensional array of correlation values, the three-dimensional array of correlation values comprising one-dimensional arrays of correlation values that have each been calculated using A-scans that are identically located in respective B-scans of the sequence of B-scans, and the method further comprises:
   converting the three-dimensional array of correlation values to a two-dimensional array of correlation values by replacing each of the one-dimensional arrays of correlation values with a respective single value that is an average of the correlation values in the one-dimensional array, the two-dimensional array of correlation values indicating the response of the retina to the light stimulus as a function of location along the scanned region of the retina and time.

4. A non-transitory computer-readable storage medium storing computer program instructions which, when executed by a computer processor, cause the computer processor to perform a method of processing functional OCT image data, which has been acquired by an OCT imaging device scanning a retina of a subject while the retina is being repeatedly stimulated by a light stimulus, to generate an indication of a response of the retina to the light stimulus, the method comprising:
   receiving, as the functional OCT image data:
      OCT image data that has been generated by the OCT imaging device repeatedly scanning a scanned region of the retina over a time period; and
      stimulus data defining a sequence of stimulus indicators each being indicative of a stimulation of the retina by the light stimulus in a respective time interval of a sequence of time intervals that spans the time period; and
   calculating a rolling window correlation between a sequence of B-scans that is based on the OCT image data and at least some of the stimulus indicators in the sequence of stimulus indicators by calculating, for each stimulus indicator, a correlation between
      stimulus indicators in a window comprising the stimulus indicator and a predetermined number of adjacent stimulus indicators, and
      B-scans of the sequence of B-scans that are based on a portion of the OCT image data generated while the retina was being stimulated in accordance with the stimulus indicators in the window; and
   generating the indication of the response of the retina to the light stimulus by combining the calculated correlations.

5. The non-transitory computer-readable storage medium according to claim 4, wherein:
   a sequence of B-scans which has been generated by the OCT imaging device repeatedly scanning the scanned region of the retina over the time period is received as the OCT image data; and
   the rolling window correlation is calculated between the sequence of B-scans and the sequence of stimulus indicators by calculating, for each stimulus indicator in the sequence of stimulus indicators, a correlation between stimulus indicators in the window comprising the stimulus indicator and the predetermined number of adjacent stimulus indicators, and B-scans of the sequence of B-scans that have been generated by the OCT imaging device while the retina was being stimulated in accordance with the stimulus indicators in the window.

6. The non-transitory computer-readable storage medium according to claim 5, wherein the calculated correlations are combined to generate a three-dimensional array of correlation values, the three-dimensional array of correlation values comprising one-dimensional arrays of correlation values that have each been calculated using A-scans that are identically located in respective B-scans of the sequence of B-scans, and the method further comprises:

converting the three-dimensional array of correlation values to a two-dimensional array of correlation values by replacing each of the one-dimensional arrays of correlation values with a respective single value that is an average of the correlation values in the one-dimensional array, the two-dimensional array of correlation values indicating the response of the retina to the light stimulus as a function of location along the scanned region of the retina and time.

7. The non-transitory computer-readable storage medium according to claim 1, wherein:

a sequence of B-scans which has been generated by the OCT imaging device repeatedly scanning the scanned region of the retina over the time period is received as the OCT image data, each of the B-scans being formed by a sequence of A-scans;

the method further comprises converting the sequence of B-scans into a sequence of reduced B-scans, by replacing each A-scan in the sequence of A-scans forming each B-scan with a respective average value of A-scan elements of the A-scan;

the rolling window correlation is calculated between reduced B-scans in the sequence of reduced B-scans and stimulus indicators in the sequence of stimulus indicators by calculating, for each stimulus indicator, a product of the stimulus indicator and a respective windowed portion of the sequence of reduced B-scans comprising a reduced B-scan which is based on a B-scan of the sequence of B-scans which has been generated by the OCT imaging device while the retina was being stimulated in accordance with the stimulus indicator; and the indication of the response of the retina to the light stimulus generated by combining the calculated products comprises a two-dimensional array of correlation values indicating the response of the retina to the light stimulus as a function of location in the scanned region of the retina and time.

8. The non-transitory computer-readable storage medium according to claim 4, wherein:

a sequence of B-scans which has been generated by the OCT imaging device repeatedly scanning the scanned region of the retina over the time period is received as the OCT image data, each of the B-scans being formed by a sequence of A-scans;

the method further comprises converting the sequence of B-scans into a sequence of reduced B-scans, by replacing each A-scan in the sequence of A-scans forming each B-scan with a respective average value of A-scan elements of the A-scan;

the rolling window correlation is calculated between the sequence of reduced B-scans and the sequence of stimulus indicators by calculating, for each stimulus indicator in the sequence of stimulus indicators, a correlation between stimulus indicators in the window comprising the stimulus indicator and the predetermined number of adjacent stimulus indicators, and reduced B-scans of the sequence of reduced B-scans that are based on OCT image data generated while the retina was being stimulated in accordance with the stimulus indicators in the window; and the indication of the response of the retina to the light stimulus generated by combining the calculated correlations comprises a two-dimensional array of correlation values indicating the response of the retina to the light stimulus as a function of location in the scanned region of the retina and time.

9. The non-transitory computer-readable storage medium according to any one of claims 3, 6, 7 and 8, wherein:

the two-dimensional array of correlation values comprises a sequence of one-dimensional arrays each indicating the response of the retina to the light stimulus as a function of location in the scanned region of the retina, in which case the method further comprises generating a normalised two-dimensional array of correlation values by subtracting the first one-dimensional array in the sequence of one-dimensional arrays from each remaining one-dimensional array in the sequence of one-dimensional arrays, the normalised two-dimensional array of correlation values indicating the response of the retina to the light stimulus as a function of location in the scanned region of the retina and time; or the two-dimensional array of correlation values comprises an array of one-dimensional arrays each indicating the response of the retina to the light stimulus as a function of location in the scanned region of the retina, in which case the method further comprises generating a normalised two-dimensional array of correlation values by calculating an array of averaged correlation values such that each averaged correlation value in the array of averaged correlation values is an average of the correlation values that are correspondingly located in the one-dimensional arrays, and subtracting the calculated array of averaged correlation values from each of the one-dimensional arrays in the array of one-dimensional arrays, the normalised two-dimensional array of correlation values indicating the response of the retina to the light stimulus as a function of location in the scanned region of the retina and time; or the two-dimensional array of correlation values comprises an array of one-dimensional arrays each indicating the response of the retina to the light stimulus as a function of location in the scanned region of the retina, in which case the method further comprises converting the two-dimensional array of correlation values to a sequence of correlation values by replacing each of the one-dimensional arrays of correlation values in the two-dimensional array with a single respective value that is an average of the correlation values in the one-dimensional array, the sequence of correlation values indicating a response of the scanned region of the retina to the light stimulus as a function of time.

10. The non-transitory computer-readable storage medium according to claim 1, wherein:

a sequence of B-scans which has been generated by the OCT imaging device repeatedly scanning the scanned region of the retina over the time period is received as the OCT image data;

the method further comprises segmenting each B-scan in the sequence of B-scans into a plurality of B-scan layers so that each B-scan layer comprises respective sections of the A-scans forming the B-scan, and concatenating corresponding B-scan layers from the segmented B-scans to generate sequences of concatenated B-scan layers;

calculating the rolling window correlation comprises calculating, for each of at least one sequence of concatenated B-scan layers of the sequences of concatenated B-scan layers, a respective rolling window correlation between concatenated B-scan layers in the sequence of concatenated B-scan layers and stimulus indicators in the sequence of stimulus indicators by:

calculating, for each stimulus indicator, a product of the stimulus indicator and a respective windowed portion of the sequence of concatenated B-scan layers comprising a B-scan layer of the B-scan layers which is based on a B-scan which has been generated by the OCT imaging device while the retina was being stimulated in accordance with the stimulus indicator; and combining the calculated products to generate an indication of a response of a layer of the retina corresponding to the sequence of concatenated B-scan layers to the light stimulus.

11. The non-transitory computer-readable storage medium according to claim 10, wherein the rolling window correlation calculated for each of the at least one sequence of concatenated B-scan layers comprises a respective three-dimensional array of correlation values, each three-dimensional array of correlation values comprising one-dimensional arrays of correlation values that have been calculated using sections of A-scans that are identically located in respective B-scans of the sequence of B-scans, and the method comprises converting each of at least one of the three-dimensional arrays of correlation values to a respective two-dimensional array of correlation values by replacing each of the one-dimensional arrays of correlation values in the three-dimensional array with a respective single value that is an average of the correlation values in the one-dimensional array, the two-dimensional array of correlation values indicating the response of the corresponding layer of the retina to the light stimulus as a function of location along the scanned region of the retina and time.

12. The non-transitory computer-readable storage medium according to claim 4, wherein:

a sequence of B-scans which has been generated by the OCT imaging device repeatedly scanning the scanned region of the retina over the time period is received as the OCT image data;

the method further comprises segmenting each B-scan in the sequence of B-scans into a plurality of B-scan layers so that each B-scan layer comprises respective sections of the A-scans forming the B-scan, and concatenating corresponding B-scan layers from the segmented B-scans to generate sequences of concatenated B-scan layers;

calculating the rolling window correlation comprises calculating, for each of at least one sequence of concatenated B-scan layers of the sequences of concatenated B-scan layers, a respective rolling window correlation between the sequence of concatenated B-scan layers and the sequence of stimulus indicators by calculating, for each stimulus indicator in the sequence of stimulus indicators, a correlation between stimulus indicators in the window comprising the stimulus indicator and the predetermined number of adjacent stimulus indicators, and B-scan layers of the B-scan layers that are based on B-scans which have been generated by the OCT imaging device while the retina was being stimulated in accordance with the stimulus indicators in the window; and generating the indication of the response of the retina to the light stimulus comprises generating, for each of the at least one sequence of concatenated B-scan layers, an indication of a response of a layer of the retina corresponding to the sequence of concatenated B-scan layers to the light stimulus, by combining the calculated correlations.

13. The non-transitory computer-readable storage medium according to claim 12, wherein the rolling window correlation calculated for each of the at least one sequence of concatenated B-scan layers comprises a respective three-dimensional array of correlation values, each three-dimensional array of correlation values comprising one-dimensional arrays that have been calculated using sections of A-scans that are identically located in respective B-scans of the sequence of B-scans, and generating the indication of the response to the light stimulus of a respective layer of the retina corresponding to each of the at least one sequence of concatenated B-scan layers comprises:

converting the three-dimensional array of correlation values to a two-dimensional array of correlation values by replacing each of the one-dimensional arrays of correlation values in the three-dimensional array with a respective single value that is an average of the correlation values in the one-dimensional array, the two-dimensional array of correlation values indicating the response of the retina to the light stimulus as a function of location along the scanned region of the retina and time.

14. The non-transitory computer-readable storage medium according to claim 1, wherein:

a sequence of B-scans which has been generated by the OCT imaging device repeatedly scanning the scanned region of the retina over the time period is received as the OCT image data;

the method further comprises:

segmenting each B-scan in the sequence of B-scans into a plurality of B-scan layers so that each B-scan layer comprises respective sections of the A-scans forming the B-scan, and concatenating corresponding B-scan layers from the segmented B-scans to generate sequences of concatenated B-scan layers;

converting each of at least one sequence of concatenated B-scan layers of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans;

calculating the rolling window correlation comprises calculating, for each of the at least one sequence of concatenated reduced B-scan layers, a respective rolling window correlation between reduced B-scan layers in the sequence of concatenated reduced B-scan layers and stimulus indicators in the sequence of stimulus indicators by:
  calculating, for each stimulus indicator, a product of the stimulus indicator and a respective windowed portion of the sequence of concatenated reduced B-scan layers comprising a reduced B-scan layer which is based on a B-scan that has been generated by the OCT imaging device while the retina was being stimulated in accordance with the stimulus indicator; and
  combining the calculated products to generate a two-dimensional array of correlation values indicating the response of a layer of the retina corresponding to the sequence of concatenated reduced B-scan layers to the light stimulus as a function of location in the scanned region of the retina and time.

15. The non-transitory computer-readable storage medium according to claim 4, wherein:
  a sequence of B-scans which has been generated by the OCT imaging device repeatedly scanning the scanned region of the retina over the time period is received as the OCT image data;
  the method further comprises:
    segmenting each B-scan in the sequence of B-scans into a plurality of B-scan layers so that each B-scan layer comprises respective sections of the A-scans forming the B-scan, and concatenating corresponding B-scan layers from the segmented B-scans to generate sequences of concatenated B-scan layers; and
    converting each of at least one sequence of concatenated B-scan layers of the sequences of concatenated B-scan layers into a respective sequence of concatenated reduced B-scan layers, by replacing, for each B-scan layer in each of the at least one sequence of concatenated B-scan layers, the sections of the A-scans forming the B-scan layer with corresponding values of an average of A-scan elements in the sections of the A-scans;
  calculating the rolling window correlation comprises calculating, for each of the at least one sequence of concatenated reduced B-scan layers, a respective rolling window correlation between the sequence of concatenated reduced B-scan layers and the sequence of stimulus indicators by calculating, for each stimulus indicator in the sequence of stimulus indicators, a correlation between
    stimulus indicators in the window comprising the stimulus indicator and the predetermined number of adjacent stimulus indicators, and
    values of the averages calculated using B-scan layers comprised in B-scans that have been generated by the OCT imaging device while the retina was being stimulated in accordance with the stimulus indicators in the window; and
  generating the indication of the response of the retina to the light stimulus comprises generating, for each of the at least one sequence of concatenated reduced B-scan layers, an indication of a response of a layer of the retina corresponding to the sequence of concatenated reduced B-scan layers to the light stimulus, by combining the calculated correlations to generate a two-dimensional array of correlation values indicating the response of the layer of the retina to the light stimulus as a function of location in the scanned region of the retina and time.

16. The non-transitory computer-readable storage medium according to any of claims 11, 13, 14 and 15, further comprising one of:
  converting each of at least one of two-dimensional arrays of correlation values to a respective sequence of correlation values by replacing each one-dimensional array of correlation values in the two-dimensional array, which one-dimensional array indicates the response of the layer of the retina corresponding to the two-dimensional array to the light stimulus as a function of location in the scanned region of the retina, with a single value that is an average of the correlation values in the one-dimensional array, the sequence of correlation values indicating a response of the layer of the retina in the scanned region to the light stimulus as a function of time;
  in a case where the each two-dimensional array of correlation values comprises a sequence of one-dimensional arrays, each of the one-dimensional arrays indicating the response of the respective layer of the retina to the light stimulus as a function of location in the scanned region of the retina, processing each two-dimensional array of correlation values to generate a respective normalised two-dimensional array of correlation values by subtracting the first one-dimensional array in the sequence of one-dimensional arrays from each remaining one-dimensional array in the sequence of one-dimensional arrays, the normalised two-dimensional array of correlation values indicating the response of the corresponding layer of the retina to the light stimulus as a function of location in the scanned region of the retina and time; or
  in a case where each two-dimensional array of correlation values comprises an array of one-dimensional arrays, each of the one-dimensional arrays indicating the response of the respective layer of the retina to the light stimulus as a function of location in the scanned region of the retina, processing each two-dimensional array of correlation values to generate a respective normalised two-dimensional array of correlation values by calculating an array of averaged correlation values such that each averaged correlation value in the array of averaged correlation values is an average of the correlation values that are correspondingly located in the one-dimensional arrays, and subtracting the calculated array of averaged correlation values from each of the one-dimensional arrays in the array of one-dimensional arrays, the normalised two-dimensional array of correlation values indicating the response of the corresponding layer of the retina to the light stimulus as a function of location in the scanned region of the retina and time.

17. A non-transitory computer-readable storage medium storing computer program instructions which, when executed by a computer processor, cause the computer processor to perform a method of processing functional OCT image data, which has been acquired by an OCT imaging device scanning a retina of a subject while the retina is being repeatedly stimulated by a light stimulus, to generate image data defining an image that provides an indication of a response of the retina to the light stimulus, the method comprising:
  receiving, as the functional OCT image data:
    OCT image data that has been generated by the OCT imaging device repeatedly scanning a scanned region of the retina over a time period; and
    stimulus data defining a sequence of stimulus indicators each being indicative of a stimulation of the retina by the light stimulus in a respective time interval of a sequence of time intervals that spans the time period;

calculating a rolling window correlation between a sequence of B-scans that is based on the OCT image data and stimulus indicators in the sequence of stimulus indicators; and using the calculated correlation to generate image data defining an image which indicates at least one of:
- the response of the scanned region of the retina to the light stimulus as a function of time;
- one or more properties of a curve defining the response of the scanned region of the retina to the light stimulus as a function of time; and
- a spatial variation, in the scanned region of the retina, of one or more properties of the curve defining the response of the scanned region of the retina to the light stimulus as a function of time, the spatial variation being overlaid on an en-face representation of at least a portion the retina which includes the scanned region.

18. The non-transitory computer-readable storage medium according to claim 17, wherein calculating the rolling window correlation between the sequence of B-scans and the stimulus indicators in the sequence of stimulus indicators comprises one of:
- calculating, for each of a plurality of windowed portions of the sequence of B-scans, a respective product of a stimulus indicator in accordance which the retina was stimulated while OCT image data, on which at least one of the B-scans in the windowed portion of the sequence of B-scans is based, was being generated by the OCT imaging device, and at least a portion of each B-scan in the windowed portion of the sequence of B-scans; or
- calculating, for each stimulus indicator, a correlation between stimulus indicators in a window comprising the stimulus indicator and a predetermined number of adjacent stimulus indicators, and B-scans of the sequence of B-scans that are based on a portion of the OCT image data generated while the retina was being stimulated in accordance with the stimulus indicators in the window.

* * * * *